United States Patent
Matsui et al.

(10) Patent No.: US 11,427,811 B2
(45) Date of Patent: *Aug. 30, 2022

(54) POLYPEPTIDES HAVING PULLULANASE ACTIVITY SUITABLE FOR USE IN LIQUEFACTION

(71) Applicant: NOVOZYMES A/S, Bagsvaerd (DK)

(72) Inventors: Tomoko Matsui, Chiba (JP); Suzanne Clark, Youngsville, NC (US); Aki Tomiki, Chiba (JP)

(73) Assignee: Novozymes A/S, Bagsvaerd (DK)

( * ) Notice: Subject to any disclaimer, the term of this patent is extended or adjusted under 35 U.S.C. 154(b) by 153 days.

This patent is subject to a terminal disclaimer.

(21) Appl. No.: 15/746,162

(22) PCT Filed: Jul. 11, 2016

(86) PCT No.: PCT/US2016/041737
§ 371 (c)(1),
(2) Date: Jan. 19, 2018

(87) PCT Pub. No.: WO2017/014974
PCT Pub. Date: Jan. 26, 2017

(65) Prior Publication Data
US 2018/0208917 A1     Jul. 26, 2018

Related U.S. Application Data

(60) Provisional application No. 62/194,982, filed on Jul. 21, 2015.

(51) Int. Cl.
| C12N 9/44 | (2006.01) |
| C12P 7/06 | (2006.01) |
| C12P 19/02 | (2006.01) |
| C12P 19/14 | (2006.01) |
| C12C 5/00 | (2006.01) |
| C12C 7/04 | (2006.01) |
| C12N 9/34 | (2006.01) |
| C13K 1/06 | (2006.01) |

(52) U.S. Cl.
CPC .............. *C12N 9/2457* (2013.01); *C12C 5/00* (2013.01); *C12C 5/004* (2013.01); *C12C 7/04* (2013.01); *C12N 9/2428* (2013.01); *C12P 7/06* (2013.01); *C12P 19/02* (2013.01); *C12P 19/14* (2013.01); *C12Y 302/01001* (2013.01); *C12Y 302/01003* (2013.01); *C12Y 302/01041* (2013.01); *C13K 1/06* (2013.01); *C07K 2319/00* (2013.01); *Y02E 50/10* (2013.01)

(58) Field of Classification Search
CPC ................ C12N 9/2457; C12N 9/2428; C12Y 302/01003; C12Y 302/01001; C12Y 302/01041; C12C 5/00; C12C 5/004; C12C 7/04; C12P 7/06; C12P 19/02; C12P 19/14; C13K 1/06; C07K 2319/00; Y02E 50/17

See application file for complete search history.

(56) References Cited

U.S. PATENT DOCUMENTS

| 5,817,498 A | 10/1998 | Deweer et al. |
| 6,074,854 A | 6/2000 | Deweer et al. |
| 2012/0252086 A1 | 10/2012 | Borchert |

FOREIGN PATENT DOCUMENTS

| WO | 01/51620 A2 | 7/2001 |
| WO | 2009/075682 A1 | 6/2009 |
| WO | 2015/007639 A1 | 1/2015 |
| WO | 2015.110473 A2 | 7/2015 |

OTHER PUBLICATIONS

Witkowski et al., Biochemistry 38:11643-11650, 1999.*
Tang et al., Phil Trans R Soc B 368:Mar. 18, 2012, 1-10, 2013.*
Seffernick et al., J. Bacteriol. 183(8):2405-2410, 2001.*
Branden et al., Introduction to Protein Structure, Garland Publishing Inc., New York, p. 247, 1991.*
Sadowski et al. Current Opinion in Structural Biology 19:357-362, 2009.*
Guo et al., PNAS 101(25):9205-9210, 2004.*
Tian et al. J. Mol. Biol. (2003) 333, 863-882.
Addou et al. J. Mol. Biol. (2009) 387, 416-430.
Devos et al., Proteins: Structure, Function and Genetics (2000), 41: 98-107.

\* cited by examiner

*Primary Examiner* — Delia M Ramirez
(74) *Attorney, Agent, or Firm* — David A. Fazzolare

(57) ABSTRACT

The present invention relates to a variant pullulanase, wherein the pullulanase comprises at least the following combination of substitutions: N368G+N393A+Q431E+L432F+A492A,S+N610R+G624S+T631S+S632C, and optionally further comprises N222P+Q252A+Q256R; wherein the variant has pullulanase activity, and wherein the variants have at least 85%, at least 90%, at least 95%, at least 96%, at least 97%, at least 98%, or at least 99%, but less than 100% sequence identity to the polypeptide of SEQ ID NO: 3. Further aspect the present invention relates to a process for liquefying starch-containing material at a temperature above the initial gelatinization temperature using an alpha-amylase and a thermo-stable pullulanase of the invention.

13 Claims, 5 Drawing Sheets

Specification includes a Sequence Listing.

SEQUENCE LISTING

```
<160> NUMBER OF SEQ ID NOS: 22

<210> SEQ ID NO 1
<211> LENGTH: 829
<212> TYPE: PRT
<213> ORGANISM: Bacillus sp-17840

<400> SEQUENCE: 1

Asp Ser Thr Ser Thr Glu Val Ile Val His Tyr His Arg Phe Asp Ser
1               5                   10                  15

Asn Tyr Ala Asn Trp Asp Leu Trp Met Trp Pro Tyr Gln Pro Val Asn
            20                  25                  30

Gly Asn Gly Ala Ala Tyr Glu Phe Ser Gly Lys Asp Asp Phe Gly Val
        35                  40                  45

Lys Ala Asp Val Gln Val Pro Gly Asp Asp Thr Gln Val Gly Leu Ile
    50                  55                  60

Val Arg Thr Asn Asp Trp Ser Gln Lys Asn Thr Ser Asp Asp Leu His
65                  70                  75                  80

Ile Asp Leu Thr Lys Gly His Glu Ile Trp Ile Val Gln Gly Asp Pro
                85                  90                  95

Asn Ile Tyr Tyr Asn Leu Ser Asp Ala Gln Ala Ala Ala Thr Pro Lys
            100                 105                 110

Val Ser Asn Ala Tyr Leu Asp Asn Glu Lys Thr Val Leu Ala Lys Leu
        115                 120                 125

Thr Asn Pro Met Thr Leu Ser Asp Gly Ser Ser Gly Phe Thr Val Thr
    130                 135                 140

Asp Lys Thr Thr Gly Glu Gln Ile Pro Val Thr Ala Ala Thr Asn Ala
145                 150                 155                 160

Asn Ser Ala Ser Ser Ser Glu Gln Thr Asp Leu Val Gln Leu Thr Leu
                165                 170                 175

Ala Ser Ala Pro Asp Val Ser His Thr Ile Gln Val Gly Ala Ala Gly
            180                 185                 190
```

```
Tyr Glu Ala Val Asn Leu Ile Pro Arg Asn Val Leu Asn Leu Pro Arg
        195                 200                 205

Tyr Tyr Tyr Ser Gly Asn Asp Leu Gly Asn Val Tyr Ser Asn Lys Ala
        210                 215                 220

Thr Ala Phe Arg Val Trp Ala Pro Thr Ala Ser Asp Val Gln Leu Leu
225                 230                 235                 240

Leu Tyr Asn Ser Glu Thr Gly Pro Val Thr Lys Gln Leu Glu Met Gln
            245                 250                 255

Lys Ser Asp Asn Gly Thr Trp Lys Leu Lys Val Pro Gly Asn Leu Lys
            260                 265                 270

Asn Trp Tyr Tyr Leu Tyr Gln Val Thr Val Asn Gly Lys Thr Gln Thr
        275                 280                 285

Ala Val Asp Pro Tyr Val Arg Ala Ile Ser Val Asn Ala Thr Arg Gly
        290                 295                 300

Met Ile Val Asp Leu Glu Asp Thr Asn Pro Pro Gly Trp Lys Glu Asp
305                 310                 315                 320

His Gln Gln Thr Pro Ala Asn Pro Val Asp Glu Val Ile Tyr Glu Val
                325                 330                 335

His Val Arg Asp Phe Ser Ile Asp Ala Asn Ser Gly Met Lys Asn Lys
            340                 345                 350

Gly Lys Tyr Leu Ala Phe Thr Glu His Gly Thr Lys Gly Pro Asp Asn
        355                 360                 365

Val Lys Thr Gly Ile Asp Ser Leu Lys Glu Leu Gly Ile Asn Ala Val
        370                 375                 380

Gln Leu Gln Pro Ile Glu Phe Asn Ser Ile Asp Glu Thr Gln Pro
385                 390                 395                 400

Asn Met Tyr Asn Trp Gly Tyr Asp Pro Arg Asn Tyr Asn Val Pro Glu
                405                 410                 415

Gly Ala Tyr Ala Thr Thr Pro Glu Gly Thr Ala Arg Ile Thr Gln Leu
            420                 425                 430

Lys Gln Leu Ile Gln Ser Ile His Lys Asp Arg Ile Ala Ile Asn Met
        435                 440                 445

Asp Val Val Tyr Asn His Thr Phe Asn Val Gly Val Ser Asp Phe Asp
        450                 455                 460

Lys Ile Val Pro Gln Tyr Tyr Arg Thr Asp Ser Ala Gly Asn Tyr
465                 470                 475                 480

Thr Asn Gly Ser Gly Val Gly Asn Glu Ile Ala Thr Glu Arg Pro Met
            485                 490                 495

Val Gln Lys Phe Val Leu Asp Ser Val Lys Tyr Trp Val Lys Glu Tyr
        500                 505                 510

His Ile Asp Gly Phe Arg Phe Asp Leu Met Ala Leu Leu Gly Lys Asp
        515                 520                 525

Thr Met Ala Lys Ile Ser Lys Glu Leu His Ala Ile Asn Pro Gly Ile
530                 535                 540

Val Leu Tyr Gly Glu Pro Trp Thr Gly Gly Thr Ser Gly Leu Ser Ser
545                 550                 555                 560

Asp Gln Leu Val Thr Lys Gly Gln Gln Lys Gly Leu Gly Ile Gly Val
            565                 570                 575

Phe Asn Asp Asn Ile Arg Asn Gly Leu Asp Gly Asn Val Phe Asp Lys
                580                 585                 590

Ser Ala Gln Gly Phe Ala Thr Gly Asp Pro Asn Gln Val Asn Val Ile
        595                 600                 605
```

```
Lys Asn Gly Val Met Gly Ser Ile Ser Asp Phe Thr Ser Ala Pro Ser
            610                 615                 620

Glu Thr Ile Asn Tyr Val Thr Ser His Asp Asn Met Thr Leu Trp Asp
625                 630                 635                 640

Lys Ile Ser Ala Ser Asn Pro Asn Asp Thr Gln Ala Asp Arg Ile Lys
                645                 650                 655

Met Asp Glu Leu Ala Gln Ala Val Val Phe Thr Ser Gln Gly Val Pro
            660                 665                 670

Phe Met Gln Gly Gly Glu Glu Met Leu Arg Thr Lys Gly Gly Asn Asp
                675                 680                 685

Asn Ser Tyr Asn Ala Gly Asp Ser Val Asn Gln Phe Asp Trp Ser Arg
690                 695                 700

Lys Ala Gln Phe Glu Asn Val Phe Asp Tyr Tyr Ser Trp Leu Ile His
705                 710                 715                 720

Leu Arg Asp Asn His Pro Ala Phe Arg Met Thr Thr Ala Asp Gln Ile
                725                 730                 735

Lys Gln Asn Leu Thr Phe Leu Asp Ser Pro Thr Asn Thr Val Ala Phe
            740                 745                 750

Glu Leu Lys Asn His Ala Asn His Asp Lys Trp Lys Asn Ile Ile Val
            755                 760                 765

Met Tyr Asn Pro Asn Lys Thr Ala Gln Thr Leu Thr Leu Pro Ser Gly
770                 775                 780

Asn Trp Thr Ile Val Gly Leu Gly Asn Gln Val Gly Glu Lys Ser Leu
785                 790                 795                 800

Gly His Val Asn Gly Thr Val Glu Val Pro Ala Leu Ser Thr Ile Ile
                805                 810                 815

Leu His Gln Gly Thr Ser Glu Asp Val Ile Asp Gln Asn
            820                 825

<210> SEQ ID NO 2
<211> LENGTH: 928
<212> TYPE: PRT
<213> ORGANISM: Bacillus deramificans

<400> SEQUENCE: 2

Asp Gly Asn Thr Thr Ile Ile Val His Tyr Phe Arg Pro Ala Gly
1               5                   10                  15

Asp Tyr Gln Pro Trp Ser Leu Trp Met Trp Pro Glu Gly Gly Ser Gly
                20                  25                  30

Ala Glu Tyr Asp Phe Asn Gly Thr Asp Ser Tyr Gly Glu Val Ala Asn
            35                  40                  45

Val Ser Ile Pro Gly Asn Pro Ser Gln Val Gly Ile Val Arg Thr
50                  55                  60

Gln Asp Trp Thr Lys Asp Val Ser Ala Asp Arg Tyr Ile Asp Leu Ser
65                  70                  75                  80

Lys Gly His Glu Val Trp Leu Val Gln Gly Asn Ser Gln Ile Phe Tyr
                85                  90                  95

Asn Glu Lys Asp Ala Glu Asp Ala Ala Lys Pro Ala Val Ser Asn Ala
            100                 105                 110

Tyr Leu Asp Ala Ser Asn Gln Val Leu Val Lys Leu Ser Gln Pro Phe
            115                 120                 125

Thr Leu Gly Glu Gly Ala Ser Gly Phe Thr Val His Asp Asp Thr Val
            130                 135                 140

Asn Lys Asp Ile Pro Val Thr Ser Val Thr Asp Ala Ser Leu Gly Gln
145                 150                 155                 160
```

-continued

Asn Val Thr Ala Val Leu Ala Gly Thr Phe Gln His Ile Phe Gly Gly
                165                 170                 175

Ser Asp Trp Ala Pro Asp Asn His Ser Thr Leu Leu Lys Lys Val Asn
            180                 185                 190

Asn Asn Leu Tyr Gln Phe Ser Gly Asp Leu Pro Glu Gly Asn Tyr Gln
        195                 200                 205

Tyr Lys Val Ala Leu Asn Asp Ser Trp Asn Asn Pro Ser Tyr Pro Ser
    210                 215                 220

Asn Asn Ile Asp Leu Thr Val Pro Thr Gly Gly Ala His Val Thr Phe
225                 230                 235                 240

Ser Tyr Val Pro Ser Thr His Ala Val Tyr Asp Ser Ile Asn Asn Pro
                245                 250                 255

Gly Ala Asp Leu Pro Val Asn Gly Ser Gly Val Lys Thr Asp Leu Val
            260                 265                 270

Thr Val Thr Leu Gly Glu Asp Pro Asp Val Ser His Thr Leu Ser Ile
        275                 280                 285

Gln Thr Asp Gly Tyr Gln Ala Lys Gln Val Ile Ser Arg Asn Val Leu
    290                 295                 300

Asp Ser Ser Gln Tyr Tyr Tyr Ser Gly Asp Leu Gly Asn Thr Tyr
305                 310                 315                 320

Thr His Lys Ala Thr Thr Phe Lys Val Trp Ala Pro Thr Ser Thr Gln
                325                 330                 335

Val Asn Val Leu Leu Tyr Asn Ser Ala Thr Gly Ser Val Thr Lys Thr
            340                 345                 350

Val Pro Met Thr Ala Ser Gly His Gly Val Trp Glu Ala Thr Val Asn
        355                 360                 365

Gln Asn Leu Glu Asn Trp Tyr Tyr Met Tyr Glu Val Thr Gly Gln Gly
    370                 375                 380

Ser Thr Arg Thr Ala Val Asp Pro Tyr Ala Thr Ala Ile Ala Pro Asn
385                 390                 395                 400

Gly Thr Arg Gly Met Ile Val Asp Leu Ala Lys Thr Asp Pro Ala Gly
                405                 410                 415

Trp Asn Ser Asp Lys His Ile Thr Pro Lys Asn Ile Glu Asp Glu Val
            420                 425                 430

Ile Tyr Glu Met Asp Val Arg Asp Phe Ser Ile Asp Pro Asn Ser Gly
        435                 440                 445

Met Lys Asn Lys Gly Lys Tyr Leu Ala Leu Thr Glu Lys Gly Thr Lys
    450                 455                 460

Gly Pro Asp Asn Val Lys Thr Gly Ile Asp Ser Leu Lys Gln Leu Gly
465                 470                 475                 480

Ile Thr His Val Gln Leu Met Pro Val Phe Ala Phe Asn Ser Val Asp
                485                 490                 495

Glu Thr Asp Pro Thr Gln Asp Asn Trp Gly Tyr Asp Pro Arg Asn Tyr
            500                 505                 510

Asp Val Pro Glu Gly Gln Tyr Ala Thr Asn Ala Asn Gly Thr Ala Arg
        515                 520                 525

Ile Lys Glu Phe Lys Glu Met Val Leu Ser Leu His Arg Glu His Ile
    530                 535                 540

Gly Val Asn Met Asp Val Val Tyr Asn His Thr Phe Ala Thr Gln Ile
545                 550                 555                 560

Ser Asp Phe Asp Lys Ile Val Pro Glu Tyr Tyr Tyr Arg Thr Asp Asp
                565                 570                 575

```
Ala Gly Asn Tyr Thr Asn Gly Ser Gly Thr Asn Glu Ile Ala Ala
            580                 585                 590

Glu Arg Pro Met Val Gln Lys Phe Ile Ile Asp Ser Leu Lys Tyr Trp
    595                 600                 605

Val Asn Glu Tyr His Ile Asp Gly Phe Arg Phe Asp Leu Met Ala Leu
610                 615                 620

Leu Gly Lys Asp Thr Met Ser Lys Ala Ala Ser Glu Leu His Ala Ile
625                 630                 635                 640

Asn Pro Gly Ile Ala Leu Tyr Gly Glu Pro Trp Thr Gly Gly Thr Ser
                645                 650                 655

Ala Leu Pro Glu Asp Gln Leu Leu Thr Lys Gly Ala Gln Lys Gly Met
            660                 665                 670

Gly Val Ala Val Phe Asn Asp Asn Leu Arg Asn Ala Leu Asp Gly Asn
        675                 680                 685

Val Phe Asp Ser Ser Ala Gln Gly Phe Ala Thr Gly Ala Thr Gly Leu
    690                 695                 700

Thr Asp Ala Ile Lys Asn Gly Val Glu Gly Ser Ile Asn Asp Phe Thr
705                 710                 715                 720

Ser Ser Pro Gly Glu Thr Ile Asn Tyr Val Thr Ser His Asp Asn Tyr
                725                 730                 735

Thr Leu Trp Asp Lys Ile Ala Leu Ser Asn Pro Asn Asp Ser Glu Ala
            740                 745                 750

Asp Arg Ile Lys Met Asp Glu Leu Ala Gln Ala Val Val Met Thr Ser
        755                 760                 765

Gln Gly Val Pro Phe Met Gln Gly Gly Glu Glu Met Leu Arg Thr Lys
    770                 775                 780

Gly Gly Asn Asp Asn Ser Tyr Asn Ala Gly Asp Thr Val Asn Glu Phe
785                 790                 795                 800

Asp Trp Ser Arg Lys Ala Gln Tyr Pro Asp Val Phe Asn Tyr Tyr Ser
                805                 810                 815

Gly Leu Ile His Leu Arg Leu Asp His Pro Ala Phe Arg Met Thr Thr
            820                 825                 830

Ala Asn Glu Ile Asn Ser His Leu Gln Phe Leu Asn Ser Pro Glu Asn
        835                 840                 845

Thr Val Ala Tyr Glu Leu Thr Asp His Val Asn Lys Asp Lys Trp Gly
    850                 855                 860

Asn Ile Ile Val Val Tyr Asn Pro Asn Lys Thr Ala Ala Thr Ile Asn
865                 870                 875                 880

Leu Pro Ser Gly Lys Trp Ala Ile Asn Ala Thr Ser Gly Lys Val Gly
                885                 890                 895

Glu Ser Thr Leu Gly Gln Ala Glu Gly Ser Val Gln Val Pro Gly Ile
            900                 905                 910

Ser Met Met Ile Leu His Gln Glu Val Ser Pro Asp His Gly Lys Lys
        915                 920                 925

<210> SEQ ID NO 3
<211> LENGTH: 828
<212> TYPE: PRT
<213> ORGANISM: Artificial
<220> FEATURE:
<223> OTHER INFORMATION: Hybrid pullulanase

<400> SEQUENCE: 3

Asp Ser Thr Ser Thr Glu Val Ile Val His Tyr His Arg Phe Asp Ser
1               5                   10                  15
```

```
Asn Tyr Ala Asn Trp Asp Leu Trp Met Trp Pro Tyr Gln Pro Val Asn
             20                  25                  30

Gly Asn Gly Ala Ala Tyr Glu Phe Ser Gly Lys Asp Asp Phe Gly Val
         35                  40                  45

Lys Ala Asp Val Gln Val Pro Gly Asp Asp Thr Gln Val Gly Leu Ile
 50                  55                  60

Val Arg Thr Asn Asp Trp Ser Gln Lys Asn Thr Ser Asp Asp Leu His
 65                  70                  75                  80

Ile Asp Leu Thr Lys Gly His Glu Ile Trp Ile Val Gln Gly Asp Pro
                 85                  90                  95

Asn Ile Tyr Tyr Asn Leu Ser Asp Ala Gln Ala Ala Thr Pro Lys
             100                 105                 110

Val Ser Asn Ala Tyr Leu Asp Asn Glu Lys Thr Val Leu Ala Lys Leu
         115                 120                 125

Thr Asn Pro Met Thr Leu Ser Asp Gly Ser Ser Gly Phe Thr Val Thr
 130                 135                 140

Asp Lys Thr Thr Gly Glu Gln Ile Pro Val Thr Ala Ala Thr Asn Ala
 145                 150                 155                 160

Asn Ser Ala Ser Ser Glu Gln Thr Asp Leu Val Gln Leu Thr Leu
             165                 170                 175

Ala Ser Ala Pro Asp Val Ser His Thr Ile Gln Val Gly Ala Ala Gly
                 180                 185                 190

Tyr Glu Ala Val Asn Leu Ile Pro Arg Asn Val Leu Asn Leu Pro Arg
             195                 200                 205

Tyr Tyr Tyr Ser Gly Asn Asp Leu Gly Asn Val Tyr Ser Asn Lys Ala
 210                 215                 220

Thr Ala Phe Arg Val Trp Ala Pro Thr Ala Ser Asp Val Gln Leu Leu
 225                 230                 235                 240

Leu Tyr Asn Ser Glu Thr Gly Pro Val Thr Lys Gln Leu Glu Met Gln
             245                 250                 255

Lys Ser Asp Asn Gly Thr Trp Lys Leu Lys Val Pro Gly Asn Leu Lys
             260                 265                 270

Asn Trp Tyr Tyr Leu Tyr Gln Val Thr Val Asn Gly Lys Thr Gln Thr
             275                 280                 285

Ala Val Asp Pro Tyr Val Arg Ala Ile Ser Val Asn Ala Thr Arg Gly
 290                 295                 300

Met Ile Val Asp Leu Glu Asp Thr Asn Pro Pro Gly Trp Lys Glu Asp
 305                 310                 315                 320

His Gln Gln Thr Pro Ala Asn Pro Val Asp Glu Val Ile Tyr Glu Val
             325                 330                 335

His Val Arg Asp Phe Ser Ile Asp Ala Asn Ser Gly Met Lys Asn Lys
             340                 345                 350

Gly Lys Tyr Leu Ala Phe Thr Glu His Gly Thr Lys Gly Pro Asp Asn
             355                 360                 365

Val Lys Thr Gly Ile Asp Ser Leu Lys Glu Leu Gly Ile Asn Ala Val
 370                 375                 380

Gln Leu Gln Pro Ile Glu Glu Phe Asn Ser Ile Asp Glu Thr Gln Pro
 385                 390                 395                 400

Asn Met Tyr Asn Trp Gly Tyr Asp Pro Arg Asn Tyr Asn Val Pro Glu
             405                 410                 415

Gly Ala Tyr Ala Thr Thr Pro Glu Gly Thr Ala Arg Ile Thr Gln Leu
             420                 425                 430

Lys Gln Leu Ile Gln Ser Ile His Lys Asp Arg Ile Ala Ile Asn Met
```

```
            435                 440                 445
Asp Val Val Tyr Asn His Thr Phe Ala Thr Gln Ile Ser Asp Phe Asp
        450                 455                 460

Lys Ile Val Pro Glu Tyr Tyr Arg Thr Asp Asp Ala Gly Asn Tyr
465                 470                 475                 480

Thr Asn Gly Ser Gly Thr Gly Asn Glu Ile Ala Ala Glu Arg Pro Met
                    485                 490                 495

Val Gln Lys Phe Ile Ile Asp Ser Leu Lys Tyr Trp Val Asn Glu Tyr
                500                 505                 510

His Ile Asp Gly Phe Arg Phe Asp Leu Met Ala Leu Leu Gly Lys Asp
                515                 520                 525

Thr Met Ser Lys Ala Ala Ser Glu Leu His Ala Ile Asn Pro Gly Ile
        530                 535                 540

Ala Leu Tyr Gly Glu Pro Trp Thr Gly Gly Thr Ser Ala Leu Pro Glu
545                 550                 555                 560

Asp Gln Leu Leu Thr Lys Gly Ala Gln Lys Gly Met Gly Val Ala Val
                    565                 570                 575

Phe Asn Asp Asn Leu Arg Asn Ala Leu Asp Gly Asn Val Phe Asp Ser
                580                 585                 590

Ser Ala Gln Gly Phe Ala Thr Gly Ala Thr Gly Leu Thr Asp Ala Ile
                595                 600                 605

Lys Asn Gly Val Glu Gly Ser Ile Asn Asp Phe Thr Ser Ser Pro Gly
                610                 615                 620

Glu Thr Ile Asn Tyr Val Thr Ser His Asp Asn Tyr Thr Leu Trp Asp
625                 630                 635                 640

Lys Ile Ala Leu Ser Asn Pro Asn Asp Ser Glu Ala Asp Arg Ile Lys
                    645                 650                 655

Met Asp Glu Leu Ala Gln Ala Val Val Met Thr Ser Gln Gly Val Pro
                660                 665                 670

Phe Met Gln Gly Gly Glu Glu Met Leu Arg Thr Lys Gly Gly Asn Asp
                675                 680                 685

Asn Ser Tyr Asn Ala Gly Asp Thr Val Asn Glu Phe Asp Trp Ser Arg
        690                 695                 700

Lys Ala Gln Tyr Pro Asp Val Phe Asn Tyr Tyr Ser Gly Leu Ile His
705                 710                 715                 720

Leu Arg Leu Asp His Pro Ala Phe Arg Met Thr Thr Ala Asn Glu Ile
                    725                 730                 735

Asn Ser His Leu Gln Phe Leu Asn Ser Pro Glu Asn Thr Val Ala Tyr
                740                 745                 750

Glu Leu Thr Asp His Val Asn Lys Asp Lys Trp Gly Asn Ile Ile Val
                755                 760                 765

Val Tyr Asn Pro Asn Lys Thr Ala Ala Thr Ile Asn Leu Pro Ser Gly
        770                 775                 780

Lys Trp Ala Ile Asn Ala Thr Ser Gly Lys Val Gly Glu Ser Thr Leu
785                 790                 795                 800

Gly Gln Ala Glu Gly Ser Val Gln Val Pro Gly Ile Ser Met Met Ile
                    805                 810                 815

Leu His Gln Glu Val Ser Pro Asp His Gly Lys Lys
                820                 825

<210> SEQ ID NO 4
<211> LENGTH: 2586
<212> TYPE: DNA
<213> ORGANISM: Artificial
```

<220> FEATURE:
<223> OTHER INFORMATION: Hybrid pullulanase CDS

<400> SEQUENCE: 4

| | | | | | |
|---|---|---|---|---|---|
| atgtccctaa | tacgttctag | gtataatcat | tttgtcattc | tttttactgt | cgccataatg | 60 |
| tttctaacag | tttgtttccc | cgcttataaa | gctttagcag | attctacctc | gacagaagtc | 120 |
| attgtgcatt | atcatcgttt | tgattctaac | tatgcaaatt | gggatctatg | gatgtggcca | 180 |
| tatcaaccag | ttaatggtaa | tggagcagca | tacgagtttt | ctggaaagga | tgattttggc | 240 |
| gttaaagcag | atgttcaagt | gcctggggat | gatacacagg | taggtctgat | tgtccgtaca | 300 |
| aatgattgga | gccaaaaaaa | tacatcagac | gatctcccata | ttgatctgac | aaagggcat | 360 |
| gaaatatgga | ttgttcaggg | ggatcccaat | atttattaca | atctgagtga | tgcgcaggct | 420 |
| gcagcgactc | caaaggtttc | gaatgcgtat | ttggataatg | aaaaaacagt | attggcaaag | 480 |
| ctaactaatc | caatgacatt | atcagatgga | tcaagcggct | ttacggttac | agataaaaca | 540 |
| acaggggaac | aaattccagt | taccgctgca | acaaatgcga | actcagcctc | ctcgtctgag | 600 |
| cagacagact | tggttcaatt | gacgttagcc | agtgcaccgg | atgtttccca | tacaatacaa | 660 |
| gtaggagcag | ccggttatga | agcagtcaat | ctcataccac | gaaatgtatt | aaatttgcct | 720 |
| cgttattatt | acagcggaaa | tgatttaggt | aacgtttatt | caaataaggc | aacggccttc | 780 |
| cgtgtatggg | ctccaactgc | ttcggatgtc | caattacttt | tatacaatag | tgaaacagga | 840 |
| cctgtaacca | aacagcttga | aatgcaaaag | agtgataacg | gtacatggaa | actgaaggtc | 900 |
| cctggtaatc | tgaaaaattg | gtattatctc | tatcaggtaa | cggtgaatgg | gaagacacaa | 960 |
| acagccgttg | acccttatgt | gcgtgctatt | tcagtcaatg | caacacgtgg | tatgatagtc | 1020 |
| gatttagaag | atacgaatcc | tcctggatgg | aaagaagatc | atcaacagac | acctgcgaac | 1080 |
| ccagtggatg | aagtaatcta | cgaagtgcat | gtgcgtgatt | tttcgattga | tgctaattca | 1140 |
| ggcatgaaaa | ataaagggaa | atatcttgcc | tttacagaac | atggcacaaa | aggccctgat | 1200 |
| aacgtgaaaa | cgggtattga | tagtttgaag | gaattaggaa | tcaatgctgt | tcaattacag | 1260 |
| ccgattgaag | aatttaacag | cattgatgaa | acccaaccaa | atatgtataa | ctggggctat | 1320 |
| gacccaagaa | actacaacgt | ccctgaagga | gcgtatgcaa | ctacaccaga | aggaacggct | 1380 |
| cgcattaccc | agttaaagca | actgattcaa | agcattcata | agatcggat | tgctatcaat | 1440 |
| atggatgtgg | tctataatca | tacctttgcc | acgcaaatct | ctgacttcga | taaaattgta | 1500 |
| ccagaatatt | attaccgtac | ggatgatgca | ggtaattata | ccaacggatc | aggtactgga | 1560 |
| aatgaaatcg | cagccgaaag | gccaatggtt | caaaaattta | ttattgattc | ccttaagtat | 1620 |
| tgggtcaatg | agtatcatat | tgacggcttc | cgttttgact | taatggcgct | gcttggaaaa | 1680 |
| gacacgatgt | cgaaagctgc | ctcggagctt | catgctatta | atccaggaat | tgcacttttac | 1740 |
| ggtgagccat | ggacgggtgg | aacctctgca | ctgccagaag | atcagcttct | gacaaaagga | 1800 |
| gctcaaaaag | gcatgggagt | agcggtgttt | aatgacaatt | tacgaaacgc | gttgacggc | 1860 |
| aatgtctttg | attcttccgc | tcaaggtttt | gcgacaggtg | caacaggctt | aactgatgca | 1920 |
| attaagaatg | gcgttgaggg | gagtattaat | gactttacct | cttcaccagg | tgagacaatt | 1980 |
| aactatgtca | caagtcatga | taactacacc | ctttgggaca | aaatagccct | aagcaaccct | 2040 |
| aatgattccg | aagcggatcg | gattaaaatg | gatgaactcg | cacaagcagt | tgttatgacc | 2100 |
| tcacaaggtg | ttccattcat | gcaaggcggg | gaagaaatgc | ttcgtacaaa | aggcggcaac | 2160 |
| gacaatagtt | ataatgcagg | cgatacggtc | aatgagtttg | attggagcag | gaaagctcaa | 2220 |

```
tatccagatg ttttcaacta ttatagcggg ctaatccacc ttcgtcttga tcacccagcc    2280
ttccgcatga cgacagctaa tgaaatcaat agccacctcc aattcctaaa tagtccagag    2340
aacacagtgg cctatgaatt aactgatcat gttaataaag acaaatgggg aaatatcatt    2400
gttgtttata acccaaataa aactgcagca accattaatt tgccgagcgg gaaatgggca    2460
atcaatgcta cgagcggtaa ggtaggagaa tccaccttg gtcaagcaga gggaagtgtc    2520
caagtaccag gtatatctat gatgatcctt catcaagagg taagcccaga ccacggtaaa    2580
aagtaa                                                              2586
```

<210> SEQ ID NO 5
<211> LENGTH: 515
<212> TYPE: PRT
<213> ORGANISM: Bacillus stearothermophilus

<400> SEQUENCE: 5

```
Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300
```

```
Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
            325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
            355                 360                 365

Tyr Tyr Gly Ile Pro Gln Tyr Asn Ile Pro Ser Leu Lys Ser Lys Ile
        370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
            405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
            485                 490                 495

Arg Pro Trp Thr Gly Glu Phe Val Arg Trp Thr Glu Pro Arg Leu Val
            500                 505                 510

Ala Trp Pro
        515

<210> SEQ ID NO 6
<211> LENGTH: 177
<212> TYPE: PRT
<213> ORGANISM: Thermoascus aurantiacus

<400> SEQUENCE: 6

Thr Arg Ile Ser Ser Cys Ser Gly Ser Arg Gln Ser Ala Leu Thr Thr
1               5                   10                  15

Ala Leu Arg Asn Ala Ala Ser Leu Ala Asn Ala Ala Asp Ala Ala
            20                  25                  30

Gln Ser Gly Ser Ala Ser Lys Phe Ser Glu Tyr Phe Lys Thr Thr Ser
            35                  40                  45

Ser Ser Thr Arg Gln Thr Val Ala Ala Arg Leu Arg Ala Val Ala Arg
        50                  55                  60

Glu Ala Ser Ser Ser Ser Gly Ala Thr Thr Tyr Tyr Cys Asp Asp
65                  70                  75                  80

Pro Tyr Gly Tyr Cys Ser Ser Asn Val Leu Ala Tyr Thr Leu Pro Ser
            85                  90                  95

Tyr Asn Ile Ile Ala Asn Cys Asp Ile Phe Tyr Thr Tyr Leu Pro Ala
            100                 105                 110

Leu Thr Thr Cys His Ala Gln Asp Gln Ala Thr Ala Leu His
            115                 120                 125

Glu Phe Thr His Ala Pro Gly Val Tyr Ser Pro Gly Thr Asp Asp Leu
        130                 135                 140

Ala Tyr Gly Tyr Gln Ala Ala Met Gly Leu Ser Ser Ser Gln Ala Val
145                 150                 155                 160
```

```
Met Asn Ala Asp Thr Tyr Ala Leu Tyr Ala Asn Ala Ile Tyr Leu Gly
            165                 170                 175

Cys

<210> SEQ ID NO 7
<211> LENGTH: 412
<212> TYPE: PRT
<213> ORGANISM: Pyrococcus furiosus

<400> SEQUENCE: 7

Ala Glu Leu Glu Gly Leu Asp Glu Ser Ala Gln Val Met Ala Thr
1               5                   10                  15

Tyr Val Trp Asn Leu Gly Tyr Asp Gly Ser Gly Ile Thr Ile Gly Ile
            20                  25                  30

Ile Asp Thr Gly Ile Asp Ala Ser His Pro Asp Leu Gln Gly Lys Val
            35                  40                  45

Ile Gly Trp Val Asp Phe Val Asn Gly Arg Ser Tyr Pro Tyr Asp Asp
        50                  55                  60

His Gly His Gly Thr His Val Ala Ser Ile Ala Ala Gly Thr Gly Ala
65                  70                  75                  80

Ala Ser Asn Gly Lys Tyr Lys Gly Met Ala Pro Gly Ala Lys Leu Ala
                85                  90                  95

Gly Ile Lys Val Leu Gly Ala Asp Gly Ser Gly Ser Ile Ser Thr Ile
            100                 105                 110

Ile Lys Gly Val Glu Trp Ala Val Asp Asn Lys Asp Lys Tyr Gly Ile
        115                 120                 125

Lys Val Ile Asn Leu Ser Leu Gly Ser Ser Gln Ser Ser Asp Gly Thr
130                 135                 140

Asp Ala Leu Ser Gln Ala Val Asn Ala Ala Trp Asp Ala Gly Leu Val
145                 150                 155                 160

Val Val Val Ala Ala Gly Asn Ser Gly Pro Asn Lys Tyr Thr Ile Gly
                165                 170                 175

Ser Pro Ala Ala Ala Ser Lys Val Ile Thr Val Gly Ala Val Asp Lys
            180                 185                 190

Tyr Asp Val Ile Thr Ser Phe Ser Ser Arg Gly Pro Thr Ala Asp Gly
        195                 200                 205

Arg Leu Lys Pro Glu Val Val Ala Pro Gly Asn Trp Ile Ile Ala Ala
210                 215                 220

Arg Ala Ser Gly Thr Ser Met Gly Gln Pro Ile Asn Asp Tyr Tyr Thr
225                 230                 235                 240

Ala Ala Pro Gly Thr Ser Met Ala Thr Pro His Val Ala Gly Ile Ala
                245                 250                 255

Ala Leu Leu Leu Gln Ala His Pro Ser Trp Thr Pro Asp Lys Val Lys
            260                 265                 270

Thr Ala Leu Ile Glu Thr Ala Asp Ile Val Lys Pro Asp Glu Ile Ala
        275                 280                 285

Asp Ile Ala Tyr Gly Ala Gly Arg Val Asn Ala Tyr Lys Ala Ile Asn
290                 295                 300

Tyr Asp Asn Tyr Ala Lys Leu Val Phe Thr Gly Tyr Val Ala Asn Lys
305                 310                 315                 320

Gly Ser Gln Thr His Gln Phe Val Ile Ser Gly Ala Ser Phe Val Thr
                325                 330                 335

Ala Thr Leu Tyr Trp Asp Asn Ala Asn Ser Asp Leu Asp Leu Tyr Leu
            340                 345                 350
```

```
Tyr Asp Pro Asn Gly Asn Gln Val Asp Tyr Ser Tyr Thr Ala Tyr Tyr
            355                 360                 365

Asp Phe Glu Lys Val Gly Tyr Tyr Asn Pro Thr Asp Gly Thr Trp Thr
    370                 375                 380

Ile Lys Val Val Ser Tyr Ser Gly Ser Ala Asn Tyr Gln Val Asp Val
385                 390                 395                 400

Val Ser Asp Gly Ser Leu Ser Gln Pro Gly Ser Ser
                405                 410

<210> SEQ ID NO 8
<211> LENGTH: 425
<212> TYPE: PRT
<213> ORGANISM: Thermococcus sp. PK

<400> SEQUENCE: 8

Met Glu Phe Asn Lys Val Phe Ser Leu Leu Val Phe Val Val Leu
1               5                   10                  15

Gly Ala Thr Ala Gly Ile Val Gly Ala Ala Pro Ala Glu Lys Ala Arg
                20                  25                  30

Val Ile Ile Thr Ile Asp Lys Asp Phe Asn Glu Asn Ser Val Phe Ala
                35                  40                  45

Leu Gly Gly Asn Val Val Ala Arg Gly Lys Val Phe Pro Ile Val Ile
    50                  55                  60

Ala Glu Leu Pro Pro Arg Ala Ile Glu Arg Leu Lys Asn Ala Lys Gly
65                  70                  75                  80

Val Val Arg Val Glu Tyr Asp Ala Glu Ala His Ile Leu Lys Gly Lys
                85                  90                  95

Pro Pro Gly Thr Gly Lys Pro Lys Pro Ser Gln Pro Ala Gln Thr Ile
                100                 105                 110

Pro Trp Gly Ile Glu Arg Ile Lys Ala Pro Asp Ala Trp Ser Ile Thr
            115                 120                 125

Asp Gly Ser Ser Gly Gly Val Ile Glu Val Ala Ile Leu Asp Thr Gly
            130                 135                 140

Ile Asp Tyr Asp His Pro Asp Leu Ala Ala Asn Leu Ala Trp Gly Val
145                 150                 155                 160

Ser Val Leu Arg Gly Lys Val Ser Thr Asn Pro Lys Asp Tyr Lys Asp
                165                 170                 175

Gln Asn Gly His Gly Thr His Val Ala Gly Thr Val Ala Ala Leu Asn
            180                 185                 190

Asn Asp Ile Gly Val Val Gly Val Ala Ser Ala Val Glu Ile Tyr Ala
            195                 200                 205

Val Arg Val Leu Asp Ala Ser Gly Arg Gly Ser Tyr Ser Asp Ile Ile
            210                 215                 220

Leu Gly Ile Glu Gln Ala Leu Leu Gly Pro Asp Gly Val Leu Asp Ser
225                 230                 235                 240

Asp Asn Asp Gly Val Ile Val Gly Asp Pro Asp Asp Ala Ala Glu
                245                 250                 255

Val Ile Ser Met Ser Leu Gly Gly Ser Ser Asp Val Gln Ala Phe His
                260                 265                 270

Asp Ala Ile Ile Glu Ala Tyr Asn Tyr Gly Val Val Ile Ala Ala
            275                 280                 285

Ser Gly Asn Asp Gly Ala Ser Ser Pro Ser Tyr Pro Ala Ala Tyr Pro
            290                 295                 300

Glu Val Ile Ala Val Gly Ala Thr Asp Ser Asp Asp Gln Val Pro Trp
```

```
                305                 310                 315                 320
Trp Ser Asn Arg Gly Val Glu Val Ser Ala Pro Gly Val Asp Ile Leu
                325                 330                 335

Ser Thr Tyr Pro Asp Asp Thr Tyr Glu Thr Leu Ser Gly Thr Ser Met
                340                 345                 350

Ala Thr Pro His Val Ser Gly Val Val Ala Leu Ile Gln Ala Ala Tyr
                355                 360                 365

Tyr Asn Lys Tyr Gly Tyr Val Leu Pro Val Gly Thr Phe Gly Asp Leu
                370                 375                 380

Thr Thr Ser Thr Val Arg Gly Ile Leu His Val Thr Ala Asp Asp Leu
385                 390                 395                 400

Gly Ser Ser Gly Trp Asp Ala Asp Tyr Gly Tyr Gly Ile Val Arg Ala
                405                 410                 415

Asp Leu Ala Val Gln Ala Ala Ile Ser
                420                 425

<210> SEQ ID NO 9
<211> LENGTH: 591
<212> TYPE: PRT
<213> ORGANISM: Talaromyces emersonii

<400> SEQUENCE: 9

Ala Thr Gly Ser Leu Asp Ser Phe Leu Ala Thr Glu Thr Pro Ile Ala
1               5                   10                  15

Leu Gln Gly Val Leu Asn Asn Ile Gly Pro Asn Gly Ala Asp Val Ala
                20                  25                  30

Gly Ala Ser Ala Gly Ile Val Ala Ser Pro Ser Arg Ser Asp Pro
                35                  40                  45

Asn Tyr Phe Tyr Ser Trp Thr Arg Asp Ala Ala Leu Thr Ala Lys Tyr
50                  55                  60

Leu Val Asp Ala Phe Ile Ala Gly Asn Lys Asp Leu Glu Gln Thr Ile
65                  70                  75                  80

Gln Gln Tyr Ile Ser Ala Gln Ala Lys Val Gln Thr Ile Ser Asn Pro
                85                  90                  95

Ser Gly Asp Leu Ser Thr Gly Gly Leu Gly Glu Pro Lys Phe Asn Val
                100                 105                 110

Asn Glu Thr Ala Phe Thr Gly Pro Trp Gly Arg Pro Gln Arg Asp Gly
                115                 120                 125

Pro Ala Leu Arg Ala Thr Ala Leu Ile Ala Tyr Ala Asn Tyr Leu Ile
                130                 135                 140

Asp Asn Gly Glu Ala Ser Thr Ala Asp Glu Ile Ile Trp Pro Ile Val
145                 150                 155                 160

Gln Asn Asp Leu Ser Tyr Ile Thr Gln Tyr Trp Asn Ser Ser Thr Phe
                165                 170                 175

Asp Leu Trp Glu Glu Val Glu Gly Ser Ser Phe Phe Thr Thr Ala Val
                180                 185                 190

Gln His Arg Ala Leu Val Glu Gly Asn Ala Leu Ala Thr Arg Leu Asn
                195                 200                 205

His Thr Cys Ser Asn Cys Val Ser Gln Ala Pro Gln Val Leu Cys Phe
                210                 215                 220

Leu Gln Ser Tyr Trp Thr Gly Ser Tyr Val Leu Ala Asn Phe Gly Gly
225                 230                 235                 240

Ser Gly Arg Ser Gly Lys Asp Val Asn Ser Ile Leu Gly Ser Ile His
                245                 250                 255
```

```
Thr Phe Asp Pro Ala Gly Gly Cys Asp Asp Ser Thr Phe Gln Pro Cys
            260                 265                 270

Ser Ala Arg Ala Leu Ala Asn His Lys Val Val Thr Asp Ser Phe Arg
            275                 280                 285

Ser Ile Tyr Ala Ile Asn Ser Gly Ile Ala Glu Gly Ser Ala Val Ala
            290                 295                 300

Val Gly Arg Tyr Pro Glu Asp Val Tyr Gln Gly Gly Asn Pro Trp Tyr
305                 310                 315                 320

Leu Ala Thr Ala Ala Ala Glu Gln Leu Tyr Asp Ala Ile Tyr Gln
            325                 330                 335

Trp Lys Lys Ile Gly Ser Ile Ser Ile Thr Asp Val Ser Leu Pro Phe
            340                 345                 350

Phe Gln Asp Ile Tyr Pro Ser Ala Ala Val Gly Thr Tyr Asn Ser Gly
            355                 360                 365

Ser Thr Thr Phe Asn Asp Ile Ile Ser Ala Val Gln Thr Tyr Gly Asp
            370                 375                 380

Gly Tyr Leu Ser Ile Val Glu Lys Tyr Thr Pro Ser Asp Gly Ser Leu
385                 390                 395                 400

Thr Glu Gln Phe Ser Arg Thr Asp Gly Thr Pro Leu Ser Ala Ser Ala
            405                 410                 415

Leu Thr Trp Ser Tyr Ala Ser Leu Leu Thr Ala Ser Ala Arg Arg Gln
            420                 425                 430

Ser Val Val Pro Ala Ser Trp Gly Glu Ser Ser Ala Ser Ser Val Pro
            435                 440                 445

Ala Val Cys Ser Ala Thr Ser Ala Thr Gly Pro Tyr Ser Thr Ala Thr
            450                 455                 460

Asn Thr Val Trp Pro Ser Gly Ser Gly Ser Ser Thr Thr Thr Ser
465                 470                 475                 480

Ser Ala Pro Cys Thr Thr Pro Thr Ser Val Ala Val Thr Phe Asp Glu
            485                 490                 495

Ile Val Ser Thr Ser Tyr Gly Glu Thr Ile Tyr Leu Ala Gly Ser Ile
            500                 505                 510

Pro Glu Leu Gly Asn Trp Ser Thr Ala Ser Ala Ile Pro Leu Arg Ala
            515                 520                 525

Asp Ala Tyr Thr Asn Ser Asn Pro Leu Trp Tyr Val Thr Val Asn Leu
            530                 535                 540

Pro Pro Gly Thr Ser Phe Glu Tyr Lys Phe Phe Lys Asn Gln Thr Asp
545                 550                 555                 560

Gly Thr Ile Val Trp Glu Asp Pro Asn Arg Ser Tyr Thr Val Pro
            565                 570                 575

Ala Tyr Cys Gly Gln Thr Thr Ala Ile Leu Asp Asp Ser Trp Gln
            580                 585                 590

<210> SEQ ID NO 10
<211> LENGTH: 555
<212> TYPE: PRT
<213> ORGANISM: Pycnoporus sanguineus

<400> SEQUENCE: 10

Gln Ser Ser Ala Val Asp Ala Tyr Val Ala Ser Glu Ser Pro Ile Ala
1               5                   10                  15

Lys Gln Gly Val Leu Asn Asn Ile Gly Pro Asn Gly Ser Lys Ala His
            20                  25                  30

Gly Ala Lys Ala Gly Ile Val Val Ala Ser Pro Ser Thr Glu Asn Pro
            35                  40                  45
```

-continued

```
Asp Tyr Leu Tyr Thr Trp Thr Arg Asp Ser Ser Leu Val Phe Lys Leu
 50                  55                  60
Leu Ile Asp Gln Phe Thr Ser Gly Asp Thr Ser Leu Arg Gly Leu
 65                  70                  75                  80
Ile Asp Asp Phe Thr Ser Ala Glu Ala Ile Leu Gln Gln Val Ser Asn
                     85                  90                  95
Pro Ser Gly Thr Val Ser Thr Gly Gly Leu Gly Glu Pro Lys Phe Asn
                100                 105                 110
Ile Asp Glu Thr Ala Phe Thr Gly Ala Trp Gly Arg Pro Gln Arg Asp
                115                 120                 125
Gly Pro Ala Leu Arg Ala Thr Ser Ile Ile Arg Tyr Ala Asn Trp Leu
130                 135                 140
Leu Asp Asn Gly Asn Thr Thr Tyr Val Ser Asn Thr Leu Trp Pro Val
145                 150                 155                 160
Ile Gln Leu Asp Leu Asp Tyr Val Ala Asp Asn Trp Asn Gln Ser Thr
                165                 170                 175
Phe Asp Leu Trp Glu Glu Val Asp Ser Ser Phe Phe Thr Thr Ala
                180                 185                 190
Val Gln His Arg Ala Leu Arg Glu Gly Ala Thr Phe Ala Ser Arg Ile
                195                 200                 205
Gly Gln Ser Ser Val Val Ser Gly Tyr Thr Thr Gln Ala Asp Asn Leu
210                 215                 220
Leu Cys Phe Leu Gln Ser Tyr Trp Asn Pro Ser Gly Gly Tyr Val Thr
225                 230                 235                 240
Ala Asn Thr Gly Gly Arg Ser Gly Lys Asp Ser Asn Thr Val Leu
                245                 250                 255
Thr Ser Ile His Thr Phe Asp Pro Ala Ala Gly Cys Asp Ala Ala Thr
                260                 265                 270
Phe Gln Pro Cys Ser Asp Lys Ala Leu Ser Asn Leu Lys Val Tyr Val
                275                 280                 285
Asp Ala Phe Arg Ser Ile Tyr Thr Ile Asn Asn Gly Ile Ala Ser Asn
                290                 295                 300
Ala Ala Val Ala Thr Gly Arg Tyr Pro Glu Asp Ser Tyr Met Gly Gly
305                 310                 315                 320
Asn Pro Trp Tyr Leu Thr Thr Ser Ala Val Ala Glu Gln Leu Tyr Asp
                325                 330                 335
Ala Leu Tyr Val Trp Asp Gln Leu Gly Gly Leu Asn Val Thr Ser Thr
                340                 345                 350
Ser Leu Ala Phe Phe Gln Gln Phe Ala Ser Gly Leu Ser Thr Gly Thr
                355                 360                 365
Tyr Ser Ala Ser Ser Thr Tyr Ala Thr Leu Thr Ser Ala Ile Arg
                370                 375                 380
Ser Phe Ala Asp Gly Phe Leu Ala Ile Asn Ala Lys Tyr Thr Pro Ala
385                 390                 395                 400
Asp Gly Gly Leu Ala Glu Gln Tyr Ser Arg Asn Asp Gly Thr Pro Leu
                405                 410                 415
Ser Ala Val Asp Leu Thr Trp Ser Tyr Ala Ala Leu Thr Ala Phe
                420                 425                 430
Ala Ala Arg Glu Gly Lys Thr Tyr Gly Ser Trp Gly Ala Ala Gly Leu
                435                 440                 445
Thr Val Pro Ala Ser Cys Ser Gly Gly Gly Ala Thr Val Ala Val
450                 455                 460
```

```
Thr Phe Asn Val Gln Ala Thr Thr Val Phe Gly Glu Asn Ile Tyr Ile
465                 470                 475                 480

Thr Gly Ser Val Ala Ala Leu Gln Asn Trp Ser Pro Asp Asn Ala Leu
            485                 490                 495

Ile Leu Ser Ala Ala Asn Tyr Pro Thr Trp Ser Ile Thr Val Asn Leu
        500                 505                 510

Pro Ala Asn Thr Val Val Gln Tyr Lys Tyr Ile Arg Lys Phe Asn Gly
        515                 520                 525

Gln Val Thr Trp Glu Ser Asp Pro Asn Asn Gln Ile Thr Thr Pro Ser
    530                 535                 540

Gly Gly Ser Phe Thr Gln Asn Asp Val Trp Arg
545                 550                 555

<210> SEQ ID NO 11
<211> LENGTH: 556
<212> TYPE: PRT
<213> ORGANISM: Gloeophyllum sepiarum

<400> SEQUENCE: 11

Gln Ser Val Asp Ser Tyr Val Ser Ser Glu Gly Pro Ile Ala Lys Ala
1               5                   10                  15

Gly Val Leu Ala Asn Ile Gly Pro Asn Gly Ser Lys Ala Ser Gly Ala
            20                  25                  30

Ser Ala Gly Val Val Val Ala Ser Pro Ser Thr Ser Asp Pro Asp Tyr
        35                  40                  45

Trp Tyr Thr Trp Thr Arg Asp Ser Ser Leu Val Phe Lys Ser Leu Ile
    50                  55                  60

Asp Gln Tyr Thr Thr Gly Ile Asp Ser Thr Ser Ser Leu Arg Thr Leu
65                  70                  75                  80

Ile Asp Asp Phe Val Thr Ala Glu Ala Asn Leu Gln Gln Val Ser Asn
                85                  90                  95

Pro Ser Gly Thr Leu Thr Thr Gly Gly Leu Gly Glu Pro Lys Phe Asn
            100                 105                 110

Val Asp Glu Thr Ala Phe Thr Gly Ala Trp Gly Arg Pro Gln Arg Asp
        115                 120                 125

Gly Pro Ala Leu Arg Ser Thr Ala Leu Ile Thr Tyr Gly Asn Trp Leu
    130                 135                 140

Leu Ser Asn Gly Asn Thr Ser Tyr Val Thr Ser Asn Leu Trp Pro Ile
145                 150                 155                 160

Ile Gln Asn Asp Leu Gly Tyr Val Val Ser Tyr Trp Asn Gln Ser Thr
                165                 170                 175

Tyr Asp Leu Trp Glu Glu Val Asp Ser Ser Phe Phe Thr Thr Ala
            180                 185                 190

Val Gln His Arg Ala Leu Arg Glu Gly Ala Ala Phe Ala Thr Ala Ile
        195                 200                 205

Gly Gln Thr Ser Gln Val Ser Ser Tyr Thr Thr Gln Ala Asp Asn Leu
    210                 215                 220

Leu Cys Phe Leu Gln Ser Tyr Trp Asn Pro Ser Gly Gly Tyr Ile Thr
225                 230                 235                 240

Ala Asn Thr Gly Gly Gly Arg Ser Gly Lys Asp Ala Asn Thr Leu Leu
                245                 250                 255

Ala Ser Ile His Thr Tyr Asp Pro Ser Ala Gly Cys Asp Ala Ala Thr
            260                 265                 270

Phe Gln Pro Cys Ser Asp Lys Ala Leu Ser Asn Leu Lys Val Tyr Val
        275                 280                 285
```

-continued

Asp Ser Phe Arg Ser Val Tyr Ser Ile Asn Ser Gly Val Ala Ser Asn
        290                 295                 300

Ala Ala Val Ala Thr Gly Arg Tyr Pro Glu Asp Ser Tyr Gln Gly Gly
305                 310                 315                 320

Asn Pro Trp Tyr Leu Thr Thr Phe Ala Val Ala Glu Gln Leu Tyr Asp
                325                 330                 335

Ala Leu Asn Val Trp Glu Ser Gln Gly Ser Leu Glu Val Thr Ser Thr
            340                 345                 350

Ser Leu Ala Phe Phe Gln Gln Phe Ser Ser Gly Val Thr Ala Gly Thr
        355                 360                 365

Tyr Ser Ser Ser Ser Thr Tyr Ser Thr Leu Thr Ser Ala Ile Lys
    370                 375                 380

Asn Phe Ala Asp Gly Phe Val Ala Ile Asn Ala Lys Tyr Thr Pro Ser
385                 390                 395                 400

Asn Gly Gly Leu Ala Glu Gln Tyr Ser Lys Ser Asp Gly Ser Pro Leu
                405                 410                 415

Ser Ala Val Asp Leu Thr Trp Ser Tyr Ala Ser Ala Leu Thr Ala Phe
            420                 425                 430

Glu Ala Arg Asn Asn Thr Gln Phe Ala Gly Trp Gly Ala Ala Gly Leu
        435                 440                 445

Thr Val Pro Ser Ser Cys Ser Gly Asn Ser Gly Gly Pro Thr Val Ala
450                 455                 460

Val Thr Phe Asn Val Asn Ala Glu Thr Val Trp Gly Glu Asn Ile Tyr
465                 470                 475                 480

Leu Thr Gly Ser Val Asp Ala Leu Glu Asn Trp Ser Ala Asp Asn Ala
                485                 490                 495

Leu Leu Leu Ser Ser Ala Asn Tyr Pro Thr Trp Ser Ile Thr Val Asn
            500                 505                 510

Leu Pro Ala Ser Thr Ala Ile Glu Tyr Lys Tyr Ile Arg Lys Asn Asn
        515                 520                 525

Gly Ala Val Thr Trp Glu Ser Asp Pro Asn Asn Ser Ile Thr Thr Pro
530                 535                 540

Ala Ser Gly Ser Thr Thr Glu Asn Asp Thr Trp Arg
545                 550                 555

<210> SEQ ID NO 12
<211> LENGTH: 559
<212> TYPE: PRT
<213> ORGANISM: Gloeophyllum trabeum

<400> SEQUENCE: 12

Gln Ser Val Asp Ser Tyr Val Gly Ser Glu Gly Pro Ile Ala Lys Ala
1               5                   10                  15

Gly Val Leu Ala Asn Ile Gly Pro Asn Gly Ser Lys Ala Ser Gly Ala
            20                  25                  30

Ala Ala Gly Val Val Val Ala Ser Pro Ser Lys Ser Asp Pro Asp Tyr
        35                  40                  45

Trp Tyr Thr Trp Thr Arg Asp Ser Ser Leu Val Phe Lys Ser Leu Ile
50                  55                  60

Asp Gln Tyr Thr Thr Gly Ile Asp Ser Ser Ser Leu Arg Ser Leu
65                  70                  75                  80

Ile Asp Ser Phe Val Ile Ala Glu Ala Asn Ile Gln Gln Val Ser Asn
                85                  90                  95

Pro Ser Gly Thr Leu Thr Thr Gly Gly Leu Gly Glu Pro Lys Phe Asn

```
                100                 105                 110
        Val Asp Glu Thr Ala Phe Thr Gly Ala Trp Gly Arg Pro Gln Arg Asp
                    115                 120                 125
        Gly Pro Ala Leu Arg Ala Thr Ala Leu Ile Thr Tyr Gly Asn Trp Leu
                    130                 135                 140
        Leu Ser Asn Gly Asn Thr Thr Trp Val Thr Ser Thr Leu Trp Pro Ile
        145                 150                 155                 160
        Ile Gln Asn Asp Leu Asn Tyr Val Val Gln Tyr Trp Asn Gln Thr Thr
                            165                 170                 175
        Phe Asp Leu Trp Glu Glu Val Asn Ser Ser Phe Phe Thr Thr Ala
                        180                 185                 190
        Val Gln His Arg Ala Leu Arg Glu Gly Ala Ala Phe Ala Thr Lys Ile
                    195                 200                 205
        Gly Gln Thr Ser Ser Val Ser Ser Tyr Thr Thr Gln Ala Ala Asn Leu
                    210                 215                 220
        Leu Cys Phe Leu Gln Ser Tyr Trp Asn Pro Thr Ser Gly Tyr Ile Thr
        225                 230                 235                 240
        Ala Asn Thr Gly Gly Gly Arg Ser Gly Lys Asp Ala Asn Thr Leu Leu
                            245                 250                 255
        Ala Ser Ile His Thr Tyr Asp Pro Ser Ala Gly Cys Asp Ala Thr Thr
                        260                 265                 270
        Phe Gln Pro Cys Ser Asp Lys Ala Leu Ser Asn Leu Lys Val Tyr Val
                    275                 280                 285
        Asp Ser Phe Arg Ser Val Tyr Ser Ile Asn Ser Gly Ile Ala Ser Asn
                    290                 295                 300
        Ala Ala Val Ala Thr Gly Arg Tyr Pro Glu Asp Ser Tyr Gln Gly Gly
        305                 310                 315                 320
        Asn Pro Trp Tyr Leu Thr Thr Phe Ala Val Ala Glu Gln Leu Tyr Asp
                            325                 330                 335
        Ala Leu Asn Val Trp Ala Ala Gln Gly Ser Leu Asn Val Thr Ser Ile
                        340                 345                 350
        Ser Leu Pro Phe Phe Gln Gln Phe Ser Ser Ser Val Thr Ala Gly Thr
                    355                 360                 365
        Tyr Ala Ser Ser Ser Thr Thr Tyr Thr Thr Leu Thr Ser Ala Ile Lys
                    370                 375                 380
        Ser Phe Ala Asp Gly Phe Val Ala Ile Asn Ala Gln Tyr Thr Pro Ser
        385                 390                 395                 400
        Asn Gly Gly Leu Ala Glu Gln Phe Ser Arg Ser Asn Gly Ala Pro Val
                            405                 410                 415
        Ser Ala Val Asp Leu Thr Trp Ser Tyr Ala Ser Ala Leu Thr Ala Phe
                        420                 425                 430
        Glu Ala Arg Asn Asn Thr Gln Phe Ala Gly Trp Gly Ala Val Gly Leu
                    435                 440                 445
        Thr Val Pro Thr Ser Cys Ser Ser Asn Ser Gly Gly Gly Gly Gly Ser
        450                 455                 460
        Thr Val Ala Val Thr Phe Asn Val Asn Ala Gln Thr Val Trp Gly Glu
        465                 470                 475                 480
        Asn Ile Tyr Ile Thr Gly Ser Val Asp Ala Leu Ser Asn Trp Ser Pro
                            485                 490                 495
        Asp Asn Ala Leu Leu Leu Ser Ala Asn Tyr Pro Thr Trp Ser Ile
                        500                 505                 510
        Thr Val Asn Leu Pro Ala Ser Thr Ala Ile Gln Tyr Lys Tyr Ile Arg
                    515                 520                 525
```

Lys Asn Asn Gly Ala Val Thr Trp Glu Ser Asp Pro Asn Asn Ser Ile
    530                 535                 540

Thr Thr Pro Ala Ser Gly Ser Val Thr Glu Asn Asp Thr Trp Arg
545                 550                 555

<210> SEQ ID NO 13
<211> LENGTH: 556
<212> TYPE: PRT
<213> ORGANISM: Trametes cingulata

<400> SEQUENCE: 13

Gln Ser Ser Ala Ala Asp Ala Tyr Val Ala Ser Glu Ser Pro Ile Ala
1               5                   10                  15

Lys Ala Gly Val Leu Ala Asn Ile Gly Pro Ser Gly Ser Lys Ser Asn
            20                  25                  30

Gly Ala Lys Ala Gly Ile Val Ile Ala Ser Pro Ser Thr Ser Asn Pro
        35                  40                  45

Asn Tyr Leu Tyr Thr Trp Thr Arg Asp Ser Ser Leu Val Phe Lys Ala
    50                  55                  60

Leu Ile Asp Gln Phe Thr Thr Gly Glu Asp Thr Ser Leu Arg Thr Leu
65                  70                  75                  80

Ile Asp Glu Phe Thr Ser Ala Glu Ala Ile Leu Gln Gln Val Pro Asn
                85                  90                  95

Pro Ser Gly Thr Val Ser Thr Gly Gly Leu Gly Glu Pro Lys Phe Asn
            100                 105                 110

Ile Asp Glu Thr Ala Phe Thr Asp Ala Trp Gly Arg Pro Gln Arg Asp
        115                 120                 125

Gly Pro Ala Leu Arg Ala Thr Ala Ile Ile Thr Tyr Ala Asn Trp Leu
    130                 135                 140

Leu Asp Asn Lys Asn Thr Thr Tyr Val Thr Asn Thr Leu Trp Pro Ile
145                 150                 155                 160

Ile Lys Leu Asp Leu Asp Tyr Val Ala Ser Asn Trp Asn Gln Ser Thr
                165                 170                 175

Phe Asp Leu Trp Glu Glu Ile Asn Ser Ser Ser Phe Phe Thr Thr Ala
            180                 185                 190

Val Gln His Arg Ala Leu Arg Glu Gly Ala Thr Phe Ala Asn Arg Ile
        195                 200                 205

Gly Gln Thr Ser Val Val Ser Gly Tyr Thr Thr Gln Ala Asn Asn Leu
    210                 215                 220

Leu Cys Phe Leu Gln Ser Tyr Trp Asn Pro Thr Gly Gly Tyr Ile Thr
225                 230                 235                 240

Ala Asn Thr Gly Gly Gly Arg Ser Gly Lys Asp Ala Asn Thr Val Leu
                245                 250                 255

Thr Ser Ile His Thr Phe Asp Pro Ala Ala Gly Cys Asp Ala Val Thr
            260                 265                 270

Phe Gln Pro Cys Ser Asp Lys Ala Leu Ser Asn Leu Lys Val Tyr Val
        275                 280                 285

Asp Ala Phe Arg Ser Ile Tyr Ser Ile Asn Ser Gly Ile Ala Ser Asn
    290                 295                 300

Ala Ala Val Ala Thr Gly Arg Tyr Pro Glu Asp Ser Tyr Met Gly Gly
305                 310                 315                 320

Asn Pro Trp Tyr Leu Thr Thr Ser Ala Val Ala Glu Gln Leu Tyr Asp
                325                 330                 335

Ala Leu Ile Val Trp Asn Lys Leu Gly Ala Leu Asn Val Thr Ser Thr

```
                340             345             350
Ser Leu Pro Phe Phe Gln Gln Phe Ser Ser Gly Val Thr Val Gly Thr
            355                 360                 365

Tyr Ala Ser Ser Ser Thr Phe Lys Thr Leu Thr Ser Ala Ile Lys
    370                 375                 380

Thr Phe Ala Asp Gly Phe Leu Ala Val Asn Ala Lys Tyr Thr Pro Ser
385                 390                 395                 400

Asn Gly Gly Leu Ala Glu Gln Tyr Ser Arg Ser Asn Gly Ser Pro Val
                405                 410                 415

Ser Ala Val Asp Leu Thr Trp Ser Tyr Ala Ala Leu Thr Ser Phe
            420                 425                 430

Ala Ala Arg Ser Gly Lys Thr Tyr Ala Ser Trp Gly Ala Ala Gly Leu
            435                 440                 445

Thr Val Pro Thr Thr Cys Ser Gly Ser Gly Ala Gly Thr Val Ala
            450                 455                 460

Val Thr Phe Asn Val Gln Ala Thr Thr Val Phe Gly Glu Asn Ile Tyr
465                 470                 475                 480

Ile Thr Gly Ser Val Pro Ala Leu Gln Asn Trp Ser Pro Asp Asn Ala
                485                 490                 495

Leu Ile Leu Ser Ala Ala Asn Tyr Pro Thr Trp Ser Ile Thr Val Asn
                500                 505                 510

Leu Pro Ala Ser Thr Thr Ile Glu Tyr Lys Tyr Ile Arg Lys Phe Asn
            515                 520                 525

Gly Ala Val Thr Trp Glu Ser Asp Pro Asn Asn Ser Ile Thr Thr Pro
            530                 535                 540

Ala Ser Gly Thr Phe Thr Gln Asn Asp Thr Trp Arg
545                 550                 555

<210> SEQ ID NO 14
<211> LENGTH: 583
<212> TYPE: PRT
<213> ORGANISM: Artificial
<220> FEATURE:
<223> OTHER INFORMATION: Hybrid alpha-amylase

<400> SEQUENCE: 14

Ala Thr Ser Asp Asp Trp Lys Gly Lys Ala Ile Tyr Gln Leu Leu Thr
1               5                   10                  15

Asp Arg Phe Gly Arg Ala Asp Asp Ser Thr Ser Asn Cys Ser Asn Leu
            20                  25                  30

Ser Asn Tyr Cys Gly Gly Thr Tyr Glu Gly Ile Thr Lys His Leu Asp
        35                  40                  45

Tyr Ile Ser Gly Met Gly Phe Asp Ala Ile Trp Ile Ser Pro Ile Pro
    50                  55                  60

Lys Asn Ser Asp Gly Gly Tyr His Gly Tyr Trp Ala Thr Asp Phe Tyr
65                  70                  75                  80

Gln Leu Asn Ser Asn Phe Gly Asp Glu Ser Gln Leu Lys Ala Leu Ile
                85                  90                  95

Gln Ala Ala His Glu Arg Asp Met Tyr Val Met Leu Asp Val Val Ala
            100                 105                 110

Asn His Ala Gly Pro Thr Ser Asn Gly Tyr Ser Gly Tyr Thr Phe Gly
        115                 120                 125

Asp Ala Ser Leu Tyr His Pro Lys Cys Thr Ile Asp Tyr Asn Asp Gln
    130                 135                 140

Thr Ser Ile Glu Gln Cys Trp Val Ala Asp Glu Leu Pro Asp Ile Asp
```

```
                  145                 150                 155                 160
            Thr Glu Asn Ser Asp Asn Val Ala Ile Leu Asn Asp Ile Val Ser Gly
                            165                 170                 175

Trp Val Gly Asn Tyr Ser Phe Asp Gly Ile Arg Ile Asp Thr Val Lys
                            180                 185                 190

His Ile Arg Lys Asp Phe Trp Thr Gly Tyr Ala Glu Ala Ala Gly Val
                            195                 200                 205

Phe Ala Thr Gly Glu Val Phe Asn Gly Asp Pro Ala Tyr Val Gly Pro
                            210                 215                 220

Tyr Gln Lys Tyr Leu Pro Ser Leu Ile Asn Tyr Pro Met Tyr Tyr Ala
            225                 230                 235                 240

Leu Asn Asp Val Phe Val Ser Lys Ser Lys Gly Phe Ser Arg Ile Ser
                            245                 250                 255

Glu Met Leu Gly Ser Asn Arg Asn Ala Phe Glu Asp Thr Ser Val Leu
                            260                 265                 270

Thr Thr Phe Val Asp Asn His Asp Asn Pro Arg Phe Leu Asn Ser Gln
                            275                 280                 285

Ser Asp Lys Ala Leu Phe Lys Asn Ala Leu Thr Tyr Val Leu Leu Gly
                            290                 295                 300

Glu Gly Ile Pro Ile Val Tyr Tyr Gly Ser Glu Gln Gly Phe Ser Gly
            305                 310                 315                 320

Gly Ala Asp Pro Ala Asn Arg Glu Val Leu Trp Thr Thr Asn Tyr Asp
                            325                 330                 335

Thr Ser Ser Asp Leu Tyr Gln Phe Ile Lys Thr Val Asn Ser Val Arg
                            340                 345                 350

Met Lys Ser Asn Lys Ala Val Tyr Met Asp Ile Tyr Val Gly Asp Asn
                            355                 360                 365

Ala Tyr Ala Phe Lys His Gly Asp Ala Leu Val Val Leu Asn Asn Tyr
                            370                 375                 380

Gly Ser Gly Ser Thr Asn Gln Val Ser Phe Ser Val Ser Gly Lys Phe
            385                 390                 395                 400

Asp Ser Gly Ala Ser Leu Met Asp Ile Val Ser Asn Ile Thr Thr Thr
                            405                 410                 415

Val Ser Ser Asp Gly Thr Val Thr Phe Asn Leu Lys Asp Gly Leu Pro
                            420                 425                 430

Ala Ile Phe Thr Ser Ala Thr Gly Gly Thr Thr Thr Thr Ala Thr Pro
                            435                 440                 445

Thr Gly Ser Gly Ser Val Thr Ser Thr Ser Lys Thr Thr Ala Thr Ala
                            450                 455                 460

Ser Lys Thr Ser Thr Ser Thr Ser Ser Thr Ser Cys Thr Thr Pro Thr
            465                 470                 475                 480

Ala Val Ala Val Thr Phe Asp Leu Thr Ala Thr Thr Thr Tyr Gly Glu
                            485                 490                 495

Asn Ile Tyr Leu Val Gly Ser Ile Ser Gln Leu Gly Asp Trp Glu Thr
                            500                 505                 510

Ser Asp Gly Ile Ala Leu Ser Ala Asp Lys Tyr Thr Ser Ser Asp Pro
                            515                 520                 525

Leu Trp Tyr Val Thr Val Thr Leu Pro Ala Gly Glu Ser Phe Glu Tyr
                            530                 535                 540

Lys Phe Ile Arg Ile Glu Ser Asp Asp Ser Val Glu Trp Glu Ser Asp
            545                 550                 555                 560

Pro Asn Arg Glu Tyr Thr Val Pro Gln Ala Cys Gly Thr Ser Thr Ala
                            565                 570                 575
```

```
Thr Val Thr Asp Thr Trp Arg
            580

<210> SEQ ID NO 15
<211> LENGTH: 828
<212> TYPE: PRT
<213> ORGANISM: Artificial
<220> FEATURE:
<223> OTHER INFORMATION: Hybrid variant pullulanase

<400> SEQUENCE: 15

Asp Ser Thr Ser Thr Glu Val Ile Val His Tyr His Arg Phe Asp Ser
1               5                   10                  15

Asn Tyr Ala Asn Trp Asp Leu Trp Met Trp Pro Tyr Gln Pro Val Asn
            20                  25                  30

Gly Asn Gly Ala Ala Tyr Glu Phe Ser Gly Lys Asp Asp Phe Gly Val
        35                  40                  45

Lys Ala Asp Val Gln Val Pro Gly Asp Thr Gln Val Gly Leu Ile
    50                  55                  60

Val Arg Thr Asn Asp Trp Ser Gln Lys Asn Thr Ser Asp Asp Leu His
65              70                  75                  80

Ile Asp Leu Thr Lys Gly His Glu Ile Trp Ile Val Gln Gly Asp Pro
                85                  90                  95

Asn Ile Tyr Tyr Asn Leu Ser Asp Ala Gln Ala Ala Thr Pro Lys
            100                 105                 110

Val Ser Asn Ala Tyr Leu Asp Asn Glu Lys Thr Val Leu Ala Lys Leu
        115                 120                 125

Thr Asn Pro Met Thr Leu Ser Asp Gly Ser Ser Gly Phe Thr Val Thr
    130                 135                 140

Asp Lys Thr Thr Gly Glu Gln Ile Pro Val Thr Ala Ala Thr Asn Ala
145                 150                 155                 160

Asn Ser Ala Ser Ser Glu Gln Thr Asp Leu Val Gln Leu Thr Leu
                165                 170                 175

Ala Ser Ala Pro Asp Val Ser His Thr Ile Gln Val Gly Ala Ala Gly
            180                 185                 190

Tyr Glu Ala Val Asn Leu Ile Pro Arg Asn Val Leu Asn Leu Pro Arg
        195                 200                 205

Tyr Tyr Tyr Ser Gly Asn Asp Leu Gly Asn Val Tyr Ser Pro Lys Ala
    210                 215                 220

Thr Ala Phe Arg Val Trp Ala Pro Thr Ala Ser Asp Val Gln Leu Leu
225                 230                 235                 240

Leu Tyr Asn Ser Glu Thr Gly Pro Val Thr Lys Ala Leu Glu Met Arg
                245                 250                 255

Lys Ser Asp Asn Gly Thr Trp Lys Leu Lys Val Pro Gly Asn Leu Lys
            260                 265                 270

Asn Trp Tyr Tyr Leu Tyr Gln Val Thr Val Asn Gly Lys Thr Gln Thr
        275                 280                 285

Ala Val Asp Pro Tyr Val Arg Ala Ile Ser Val Asn Ala Thr Arg Gly
    290                 295                 300

Met Ile Val Asp Leu Glu Asp Thr Asn Pro Pro Gly Trp Lys Glu Asp
305                 310                 315                 320

His Gln Gln Thr Pro Ala Asn Pro Val Asp Glu Val Ile Tyr Glu Val
                325                 330                 335

His Val Arg Asp Phe Ser Ile Asp Ala Asn Ser Gly Met Lys Asn Lys
            340                 345                 350
```

```
Gly Lys Tyr Leu Ala Phe Thr Glu His Gly Thr Lys Gly Pro Asp Gly
        355                 360                 365

Val Lys Thr Gly Ile Asp Ser Leu Lys Glu Leu Gly Ile Asn Ala Val
    370                 375                 380

Gln Leu Gln Pro Ile Glu Glu Phe Ala Ser Ile Asp Glu Thr Gln Pro
385                 390                 395                 400

Asn Met Tyr Asn Trp Gly Tyr Asp Pro Arg Asn Tyr Asn Val Pro Glu
                405                 410                 415

Gly Ala Tyr Ala Thr Thr Pro Glu Gly Thr Ala Arg Ile Thr Glu Phe
                420                 425                 430

Lys Gln Leu Ile Gln Ser Ile His Lys Asp Arg Ile Ala Ile Asn Met
        435                 440                 445

Asp Val Val Tyr Asn His Thr Phe Ala Thr Gln Ile Ser Asp Phe Asp
    450                 455                 460

Lys Ile Val Pro Glu Tyr Tyr Arg Thr Asp Ala Gly Asn Tyr
465                 470                 475                 480

Thr Asn Gly Ser Gly Thr Gly Asn Glu Ile Ala Ala Glu Arg Pro Met
                485                 490                 495

Val Gln Lys Phe Ile Ile Asp Ser Leu Lys Tyr Trp Val Asn Glu Tyr
        500                 505                 510

His Ile Asp Gly Phe Arg Phe Asp Leu Met Ala Leu Leu Gly Lys Asp
    515                 520                 525

Thr Met Ser Lys Ala Ala Ser Glu Leu His Ala Ile Asn Pro Gly Ile
    530                 535                 540

Ala Leu Tyr Gly Glu Pro Trp Thr Gly Gly Thr Ser Ala Leu Pro Glu
545                 550                 555                 560

Asp Gln Leu Leu Thr Lys Gly Ala Gln Lys Gly Met Gly Val Ala Val
                565                 570                 575

Phe Asn Asp Asn Leu Arg Asn Ala Leu Asp Gly Asn Val Phe Asp Ser
                580                 585                 590

Ser Ala Gln Gly Phe Ala Thr Gly Ala Thr Gly Leu Thr Asp Ala Ile
        595                 600                 605

Lys Arg Gly Val Glu Gly Ser Ile Asn Asp Phe Thr Ser Ser Pro Ser
    610                 615                 620

Glu Thr Ile Asn Tyr Val Ser Cys His Asp Asn Tyr Thr Leu Trp Asp
625                 630                 635                 640

Lys Ile Ala Leu Ser Asn Pro Asn Asp Ser Glu Ala Asp Arg Ile Lys
                645                 650                 655

Met Asp Glu Leu Ala Gln Ala Val Val Met Thr Ser Gln Gly Val Pro
                660                 665                 670

Phe Met Gln Gly Gly Glu Glu Met Leu Arg Thr Lys Gly Gly Asn Asp
        675                 680                 685

Asn Ser Tyr Asn Ala Gly Asp Thr Val Asn Glu Phe Asp Trp Ser Arg
    690                 695                 700

Lys Ala Gln Tyr Pro Asp Val Phe Asn Tyr Tyr Ser Gly Leu Ile His
705                 710                 715                 720

Leu Arg Leu Asp His Pro Ala Phe Arg Met Thr Thr Ala Asn Glu Ile
                725                 730                 735

Asn Ser His Leu Gln Phe Leu Asn Ser Pro Glu Asn Thr Val Ala Tyr
                740                 745                 750

Glu Leu Thr Asp His Val Asn Lys Asp Lys Trp Gly Asn Ile Ile Val
        755                 760                 765
```

| Val | Tyr | Asn | Pro | Asn | Lys | Thr | Ala | Ala | Thr | Ile | Asn | Leu | Pro | Ser | Gly |
|---|---|---|---|---|---|---|---|---|---|---|---|---|---|---|---|
| | 770 | | | | 775 | | | | 780 | | | | | | |

| Lys | Trp | Ala | Ile | Asn | Ala | Thr | Ser | Gly | Lys | Val | Gly | Glu | Ser | Thr | Leu |
|---|---|---|---|---|---|---|---|---|---|---|---|---|---|---|---|
| 785 | | | | | 790 | | | | | 795 | | | | | 800 |

| Gly | Gln | Ala | Glu | Gly | Ser | Val | Gln | Val | Pro | Gly | Ile | Ser | Met | Met | Ile |
|---|---|---|---|---|---|---|---|---|---|---|---|---|---|---|---|
| | | | | 805 | | | | | 810 | | | | | 815 | |

| Leu | His | Gln | Glu | Val | Ser | Pro | Asp | His | Gly | Lys | Lys |
|---|---|---|---|---|---|---|---|---|---|---|---|
| | | 820 | | | | | 825 | | | | |

<210> SEQ ID NO 16
<211> LENGTH: 2586
<212> TYPE: DNA
<213> ORGANISM: Artificial
<220> FEATURE:
<223> OTHER INFORMATION: CDS for P380-2

<400> SEQUENCE: 16

```
atgtccctaa tacgttctag gtataatcat tttgtcattc tttttactgt cgccataatg      60
tttctaacag tttgtttccc cgcttataaa gctttagcag attctacctc gacagaagtc     120
attgtgcatt atcatcgttt tgattctaac tatgcaaatt gggatctatg gatgtggcca     180
tatcaaccag ttaatggtaa tggagcagca tacgagtttt ctggaaagga tgattttggc     240
gttaaagcag atgttcaagt gcctggggat gatacacagg taggtctgat tgtccgtaca     300
aatgattgga gccaaaaaaa tacatcgagc gatctccata ttgatctgac aaaggggcat     360
gaaatatgga ttgttcaggg ggatcccaat atttattaca atctgagtga tgcgcaggct     420
gcagcgactc caaggtttc gaatgcgtat ttggataatg aaaaaacagt attggcaaag     480
ctaactaatc caatgacatt atcagatgga tcaagcggct ttacggttac agataaaaca     540
acaggggaac aaattccagt taccgctgca acaaatgcga actcagcctc ctcgtctgag     600
cagacagact tggttcaatt gacgttagcc agtgcaccgg atgtttccca tacaatacaa     660
gtaggagcag ccggttatga agcagtcaat ctcataccac gaaatgtatt aaatttgcct     720
cgttattatt acagcggaaa tgatttaggt aacgtttatt caccgaaggc aacggccttc     780
cgtgtatggg ctccaactgc ttcggatgtc caattacttt tatacaatag tgaaacagga     840
cctgtaacca aagcacttga aatgcgcaag agtgataacg gtacatggaa actgaaggtc     900
cctggtaatc tgaaaaattg gtattatctc tatcaggtaa cggtgaatgg gaagacacaa     960
acagccgttg accttatgt gcgtgctatt tcagtcaatg caacacgtgg tatgatagtc    1020
gatttagaag atacgaatcc tcctggatgg aaagaagatc atcaacagac acctgcgaac    1080
ccagtggatg aagtaatcta cgaagtgcat gtgcgtgatt tttcgattga tgctaattca    1140
ggcatgaaaa ataaagggaa atatcttgcc tttacagaac atggcacaaa aggccctgat    1200
ggcgtgaaaa cgggtattga tagtttgaag gaattaggaa tcaatgctgt tcaattacag    1260
ccgattgaag aatttgccag cattgatgaa acccaaccaa atatgtataa ctggggctat    1320
gacccaagaa actacaacgt ccctgaagga gcgtatgcaa ctacaccaga aggaacggct    1380
cgcattacgg agtttaagca actgattcaa agcattcata agatcggat tgctatcaat    1440
atggatgtgg tctataatca tacctttgcc acgcaaatct ctgacttcga taaaattgta    1500
ccagaatatt attaccgtac ggatgatgca ggtaattata ccaacggatc aggtactgga    1560
aatgaaatcg cagccgaaag gccaatggtt caaaaattta ttattgattc ccttaagtat    1620
tgggtcaatg agtatcatat tgacggcttc cgttttgact taatggcgct gcttggaaaa    1680
gacacgatgt cgaaagctgc ctcggagctt catgctatta atccaggaat tgcactttac    1740
```

```
ggtgagccat ggacgggtgg aacctctgca ctgccagaag atcagcttct gacaaaagga   1800
gctcaaaaag gcatgggagt agcggtgttt aatgacaatt tacgaaacgc gttggacggc   1860
aatgtctttg attcttccgc tcaaggtttt gcgacaggtg caacaggctt aactgatgca   1920
attaagcgcg gcgttgaggg gagtattaat gactttacct cttcaccaag cgagacaatt   1980
aactatgtct catgtcatga taactacacc ctttgggaca aaatagccct aagcaaccct   2040
aatgattccg aagcggatcg gattaaaatg gatgaactcg cacaagcagt tgttatgacc   2100
tcacaaggtg ttccattcat gcaaggcggg gaagaaatgc ttcgtacaaa aggcggcaac   2160
gacaatagtt ataatgcagg cgatacggtc aatgagtttg attggagcag gaaagctcaa   2220
tatccagatg ttttcaacta ttatagcggg ctaatccacc ttcgtcttga tcacccagcc   2280
ttccgcatga cgacagctaa tgaaatcaat agccacctcc aattcctaaa tagtccagag   2340
aacacagtgg cctatgaatt aactgatcat gttaataaag acaaatgggg aaatatcatt   2400
gttgtttata acccaaataa aactgcagca accattaatt tgccgagcgg gaaatgggca   2460
atcaatgcta cgagcggtaa ggtaggagaa tccaccccttg gtcaagcaga gggaagtgtt   2520
caagtcccag gtatatctat gatgatcctt catcaagagg taagcccaga ccacggtaaa   2580
aagtaa                                                              2586

<210> SEQ ID NO 17
<211> LENGTH: 828
<212> TYPE: PRT
<213> ORGANISM: Artificial
<220> FEATURE:
<223> OTHER INFORMATION: Hybrid variant pullulanase

<400> SEQUENCE: 17

Asp Ser Thr Ser Thr Glu Val Ile Val His Tyr His Arg Phe Asp Ser
1               5                   10                  15

Asn Tyr Ala Gly Trp Asp Leu Trp Met Trp Pro Lys Gln Pro Val Asn
            20                  25                  30

Gly Asn Gly Ala Ala Tyr Glu Phe Ser Gly Lys Asp Asp Phe Gly Val
        35                  40                  45

Lys Ala Asp Val Gln Val Pro Gly Asp Thr Gln Val Gly Leu Ile
    50                  55                  60

Val Arg Thr Asn Asp Trp Ser Gln Lys Asn Thr Ser Asp Asp Leu Tyr
65                  70                  75                  80

Ile Asp Leu Thr Lys Gly His Glu Ile Trp Ile Val Gln Gly Asp Pro
                85                  90                  95

Asn Ile Tyr Tyr Asn Leu Ser Asp Ala Gln Ala Ala Thr Pro Lys
            100                 105                 110

Val Ser Asn Ala Tyr Leu Asp Asn Glu Lys Thr Val Leu Ala Lys Leu
        115                 120                 125

Thr Asn Pro Met Thr Leu Ser Asp Gly Ser Ser Gly Phe Thr Val Thr
    130                 135                 140

Asp Lys Thr Thr Gly Glu Gln Ile Pro Val Thr Ala Ala Thr Asn Ala
145                 150                 155                 160

Asn Ser Ala Ser Ser Glu Gln Thr Asp Leu Val Gln Leu Thr Leu
            165                 170                 175

Ala Ser Ala Pro Asp Val Ser His Thr Ile Arg Val Gly Ala Ala Gly
        180                 185                 190

Tyr Glu Ala Val Asn Leu Ile Pro Arg Asn Val Leu Asn Leu Pro Arg
    195                 200                 205
```

-continued

Tyr Tyr Tyr Ser Gly Asn Asp Leu Gly Asn Val Tyr Ser Pro Lys Ala
210                 215                 220

Thr Ala Phe Arg Val Trp Ala Pro Thr Ala Ser Asp Val Gln Leu Leu
225                 230                 235                 240

Leu Tyr Asn Ser Glu Thr Gly Pro Val Thr Lys Ala Leu Glu Met Arg
            245                 250                 255

Lys Ser Asp Asn Gly Thr Trp Lys Leu Lys Val Pro Gly Asn Leu Lys
            260                 265                 270

Asn Trp Tyr Tyr Leu Tyr Gln Val Thr Val Asn Gly Lys Thr Gln Thr
            275                 280                 285

Ala Val Asp Pro Tyr Val Arg Ala Ile Ser Val Asn Ala Thr Arg Gly
290                 295                 300

Met Ile Val Asp Leu Ala Lys Thr Asn Pro Pro Gly Trp Lys Glu Asp
305                 310                 315                 320

His Gln Gln Thr Pro Ala Asn Pro Val Asp Glu Val Ile Tyr Glu Val
            325                 330                 335

His Val Arg Asp Phe Ser Ile Asp Ala Asn Ser Gly Met Lys Asn Lys
            340                 345                 350

Gly Lys Tyr Leu Ala Phe Thr Glu His Gly Thr Lys Gly Pro Asp Gly
            355                 360                 365

Val Lys Thr Gly Ile Asp Ser Leu Lys Glu Leu Gly Ile Asn Ala Val
            370                 375                 380

Gln Leu Leu Pro Ile Glu Glu Phe Ala Ser Ile Asp Glu Thr Gln Pro
385                 390                 395                 400

Asn Met Tyr Asn Trp Gly Tyr Asp Pro Arg Asn Tyr Asn Val Pro Glu
            405                 410                 415

Gly Ala Tyr Ala Thr Thr Pro Glu Gly Thr Ala Arg Ile Thr Glu Phe
            420                 425                 430

Lys Gln Leu Ile Gln Ser Ile His Lys Asp Arg Ile Ala Ile Asn Met
            435                 440                 445

Asp Val Val Tyr Asn His Thr Phe Ala Thr Gly Ile Ser Asp Phe Asp
            450                 455                 460

Lys Ile Val Pro Glu Tyr Tyr Tyr Arg Thr Asp Asp Ala Gly Asn Tyr
465                 470                 475                 480

Thr Asn Gly Ser Gly Thr Gly Asn Glu Ile Ala Ala Glu Arg Pro Met
            485                 490                 495

Val Gln Lys Phe Ile Ile Asp Ser Leu Lys Tyr Trp Val Asn Glu Tyr
            500                 505                 510

His Ile Asp Gly Phe Arg Phe Asp Leu Met Ala Leu Leu Gly Lys Asp
            515                 520                 525

Thr Met Ser Lys Ala Ala Ser Glu Leu His Ala Ile Asn Pro Gly Ile
530                 535                 540

Ala Leu Tyr Gly Glu Pro Trp Thr Gly Gly Thr Ser Ala Leu Pro Glu
545                 550                 555                 560

Asp Gln Leu Leu Thr Lys Gly Ala Gln Lys Gly Met Gly Val Ala Val
            565                 570                 575

Phe Asn Asp Asn Leu Arg Asn Ala Leu Ser Gly Asn Val Phe Asp Ser
            580                 585                 590

Ser Ala Gln Gly Phe Ala Thr Gly Ala Thr Gly Leu Thr Asp Ala Ile
            595                 600                 605

Lys Arg Gly Val Glu Gly Ser Ile Asn Asp Phe Thr Ser Ser Pro Ser
610                 615                 620

```
Glu Thr Ile Asn Tyr Val Ser Cys His Asp Asn Tyr Thr Leu Trp Asp
625                 630                 635                 640

Lys Ile Ala Leu Ser Asn Pro Asn Asp Ser Glu Ala Asp Arg Ile Lys
            645                 650                 655

Met Asp Glu Leu Ala Gln Ala Val Val Met Thr Ser Gln Gly Val Pro
                660                 665                 670

Phe Met Gln Gly Gly Glu Glu Met Leu Arg Thr Lys Gly Gly Asn Asp
            675                 680                 685

Asn Ser Tyr Asn Ala Gly Asp Thr Val Asn Arg Phe Asp Trp Ser Arg
        690                 695                 700

Lys Ala Gln Tyr Pro Asp Val Phe Asn Tyr Tyr Ser Gly Leu Ile His
705                 710                 715                 720

Leu Arg Leu Asp His Pro Ala Phe Arg Met Thr Thr Ala Asn Glu Ile
                725                 730                 735

Asn Ser His Leu Gln Phe Leu Asn Ser Pro Glu Asn Thr Val Ala Tyr
            740                 745                 750

Glu Leu Thr Asp His Val Asn Lys Asp Lys Trp Gly Asn Ile Ile Val
        755                 760                 765

Val Tyr Asn Pro Asn Lys Thr Ala Ala Thr Ile Asn Leu Pro Ser Gly
770                 775                 780

Lys Trp Ala Ile Asn Ala Thr Ser Gly Lys Val Gly Glu Arg Thr Leu
785                 790                 795                 800

Gly Gln Ala Glu Gly Ser Val Gln Val Pro Gly Ile Ser Met Met Ile
                805                 810                 815

Leu His Gln Glu Val Ser Pro Asp His Gly Lys Lys
            820                 825

<210> SEQ ID NO 18
<211> LENGTH: 2586
<212> TYPE: DNA
<213> ORGANISM: Artificial
<220> FEATURE:
<223> OTHER INFORMATION: CDS for P507-2

<400> SEQUENCE: 18
atgtccctaa tacgttctag gtataatcat tttgtcattc tttttactgt cgccataatg      60
tttctaacag tttgtttccc cgcttataaa gctttagcag attctacctc gacagaagtc     120
attgtgcatt atcatcgttt tgattctaac tatgcaggct gggatctatg gatgtggcca     180
aaacaaccag ttaatggtaa tggagcagca tacgagtttt ctggaaagga tgattttggc     240
gttaaagcag atgttcaagt gcctggggat gatacacagg taggtctgat tgtccgtaca     300
aatgattgga gccaaaaaaa tacatcagac gatctctata ttgatctgac aaagggcat      360 gaaatatgga ttgttcaggg ggatcccaat atttattaca atctgagtga tgcgcaggct     420
gcagcgactc caaaggtttc gaatgcgtat ttggataatg aaaaaacagt attggcaaag     480
ctaactaatc caatgacatt atcagatgga tcaagcggct ttacggttac agataaaaca     540
acaggggaac aaattccagt taccgctgca acaaatgcga actcagcctc ctcgtctgag     600
cagacagact tggttcaatt gacgttagcc agtgcaccgg atgtttccca tacaataaga     660
gtaggagcag ccggttatga agcagtcaat ctcataccac gaaatgtatt aaatttgcct     720
cgttattatt acagcggaaa tgatttaggt aacgtttatt caccgaaggc aacggccttc     780
cgtgtatggg ctccaactgc ttcggatgtc caattacttt tatacaatag tgaaacagga     840
cctgtaacca aagcacttga aatgcgcaag agtgataacg gtacatggaa actgaaggtc     900
```

```
cctggtaatc tgaaaaattg gtattatctc tatcaggtaa cggtgaatgg gaagacacaa    960
acagccgttg acccttatgt gcgtgctatt tcagtcaatg caacacgtgg tatgatagtc   1020
gatttagcaa aaacgaatcc tcctggatgg aaagaagatc atcaacagac acctgcgaac   1080
ccagtggatg aagtaatcta cgaagtgcat gtgcgtgatt tttcgattga tgctaattca   1140
ggcatgaaaa ataaagggaa atatcttgcc tttacagaac atggcacaaa aggccctgat   1200
ggcgtgaaaa cggtattga tagtttgaag gaattaggaa tcaatgctgt tcaattactg    1260
ccgattgaag aatttgccag cattgatgaa acccaaccaa atatgtataa ctggggctat   1320
gacccaagaa actacaacgt ccctgaagga gcgtatgcaa ctacaccaga aggaacggct   1380
cgcattacgg agtttaagca actgattcaa agcattcata aagatcggat tgctatcaat   1440
atggatgtgg tctataatca tacctttgcc acgggaatct ctgacttcga taaaattgta   1500
ccagaatatt attaccgtac ggatgatgca ggtaattata ccaacggatc aggtactgga   1560
aatgaaatcg cagccgaaag gccaatggtt caaaaattta ttattgattc ccttaagtat   1620
tgggtcaatg agtatcatat tgacggcttc cgttttgact taatggcgct gcttggaaaa   1680
gacacgatgt cgaaagctgc ctcggagctt catgctatta atccaggaat tgcactttac   1740
ggtgagccat ggacgggtgg aacctctgca ctgccagaag atcagcttct gacaaaagga   1800
gctcaaaaag gcatgggagt agcggtgttt aatgacaatt tacgaaacgc gttgtcaggc   1860
aatgtctttg attcttccgc tcaaggtttt gcgacaggtg caacaggctt aactgatgca   1920
attaagcgcg gcgttgaggg gagtattaat gactttacct cttcaccaag cgagacaatt   1980
aactatgtct catgtcatga taactacacc ctttgggaca aaatagccct aagcaaccct   2040
aatgattccg aagcggatcg gattaaaatg gatgaactcg cacaagcagt tgttatgacc   2100
tcacaaggtg ttccattcat gcaaggcggg gaagaaatgc ttcgtacaaa aggcggcaac   2160
gacaatagtt ataatgcagg cgatacggtc aatcggtttg attggagcag gaaagctcaa   2220
tatccagatg ttttcaacta ttatagcggg ctaatccacc ttcgtcttga tcacccagcc   2280
ttccgcatga cgacagctaa tgaaatcaat agccacctcc aattcctaaa tagtccagag   2340
aacacagtgg cctatgaatt aactgatcat gttaataaag acaaatgggg aaatatcatt   2400
gttgtttata acccaaataa aactgcagca accattaatt tgccgagcgg gaaatgggca   2460
atcaatgcta cgagcggtaa ggtaggagaa agaacccttg gtcaagcaga gggaagtgtc   2520
caagtaccag gtatatctat gatgatcctt catcaagagg taagcccaga ccacggtaaa   2580
aagtaa                                                              2586

<210> SEQ ID NO 19
<211> LENGTH: 59
<212> TYPE: DNA
<213> ORGANISM: Artificial
<220> FEATURE:
<223> OTHER INFORMATION: PCR primer

<400> SEQUENCE: 19
atgtattatg gagctctata aaaatgagga gggaaccgaa tgtccctaat acgttctag    59

<210> SEQ ID NO 20
<211> LENGTH: 37
<212> TYPE: DNA
<213> ORGANISM: Artificial
<220> FEATURE:
<223> OTHER INFORMATION: PCR primer

<400> SEQUENCE: 20
```

```
ttattgatta acgcgtttaa ttttgatcaa tgacatc                              37

<210> SEQ ID NO 21
<211> LENGTH: 61
<212> TYPE: DNA
<213> ORGANISM: Artificial
<220> FEATURE:
<223> OTHER INFORMATION: PCR primer

<400> SEQUENCE: 21
atgtattatg gagctctata aaaatgagga gggaaccgaa tggctaaaaa actaatttat    60
g                                                                     61

<210> SEQ ID NO 22
<211> LENGTH: 36
<212> TYPE: DNA
<213> ORGANISM: Artificial
<220> FEATURE:
<223> OTHER INFORMATION: PCR primer

<400> SEQUENCE: 22
ttattgatta acgcgtttac tttttaccgt ggtctg                               36
```

POLYPEPTIDES HAVING PULLULANASE ACTIVITY SUITABLE FOR USE IN LIQUEFACTION

CROSS-REFERENCE TO RELATED APPLICATIONS

This application is a 35 U.S.C. 371 national application of PCT/US2016/041737 filed Jul. 11, 2016, which claims priority or the benefit under 35 U.S.C. 119 of U.S. application No. 62/194,982 filed Jul. 21, 2015, the contents of which are fully incorporated herein by reference.

REFERENCE TO A SEQUENCE LISTING

This application contains a Sequence Listing in computer readable form, which is incorporated herein by reference.

FIELD OF THE INVENTION

The present invention relates to use of thermo-stable pullulanase variants in a process for producing fermentation products from starch-containing material and to polypeptides having pullulanase activity.

BACKGROUND OF THE INVENTION

Starch usually consists of about 80% amylopectin and 20% amylose. Amylopectin is a branched polysaccharide in which linear chains alpha-1,4 D-glucose residues are joined by alpha-1,6 glucosidic linkages. Amylopectin is partially degraded by alpha-amylase, which hydrolyzes the 1,4-alpha-glucosidic linkages to produce branched and linear oligosaccharides. Prolonged degradation of amylopectin by alpha-amylase results in the formation of so-called alpha-limit dextrins that are not susceptible to further hydrolysis by the alpha-amylase. Branched oligosaccharides can be hydrolyzed into linear oligosaccharides by a debranching enzyme. The remaining branched oligosaccharides can be depolymerized to D-glucose by glucoamylase, which hydrolyzes linear oligosaccharides into D-glucose.

Debranching enzymes which can attack amylopectin are divided into two classes: isoamylases (E.C. 3.2.1.68) and pullulanases (E.C. 3.2.1.41), respectively. Isoamylase hydrolyses alpha-1,6-D-glucosidic branch linkages in amylopectin and beta-limit dextrins and can be distinguished from pullulanases by the inability of isoamylase to attack pullulan, and by their limited action on alpha-limit dextrins.

It is well-known in the art to add isoamylases or pullulanases in starch conversion processes. Pullulanase is a starch debranching enzyme having pullulan 6-glucano-hydrolase activity (EC3.2.1.41) that catalyzes the hydrolyses the α-1,6-glycosidic bonds in pullulan, releasing maltotriose with reducing carbohydrate ends. Usually pullulanase is used in combination with an alpha amylase and/or a glucoamylase.

Pullulanases are known in the art. U.S. Pat. Nos. 6,074, 854 and 5,817,498 disclose a pullulanase from *Bacillus deramificans*. WO2009/075682 discloses a pullulanase derived from *Bacillus acidopullulyticus*.

WO 2015/007639 discloses a hybrid pullulanase obtained by combining an N-terminal fragment of a pullulanase from *Bacillus acidopullulyticus* fused to a C-terminal fragment of a pullulanase from *Bacillus deramificans*. Prior art pullulanases derived from *Bacillus* sp. have so far not been sufficiently thermos-stable in order to be added during liquefaction in conventional starch conversion processes.

It is an object of the present invention to provide pullulanase variants having increased thermo-activity suitable for use in liquefaction of starch containing material.

SUMMARY OF THE INVENTION

The present invention relates to a variant pullulanase, wherein the pullulanase comprises at least the following combination of substitutions: N368G+N393A+Q431E+L432F+A492A,S+N610R+G624S+T631S+S632C, and optionally further comprises N222P+Q252A+Q256R; wherein the variant has pullulanase activity, and wherein the variants have at least 85%, at least 90%, at least 95%, at least 96%, at least 97%, at least 98%, or at least 99%, but less than 100% sequence identity to the polypeptide of SEQ ID NO: 3.

Further aspect the present invention relates to a process for liquefying starch-containing material at a temperature above the initial gelatinization temperature using an alpha-amylase and a thermo-stable pullulanase of the invention.

Thus in second aspect the invention relates to a process for producing a syrup from starch-containing material comprising the steps of:
a) liquefying the starch-containing material at a temperature above the initial gelatinization temperature using an alpha-amylase and a variant pullulanase of the invnetion;
b) saccharifying using a glucoamylase.

In a third aspect the present invention relates to a process for producing fermentation products from starch-containing material comprising the steps of:
a) liquefying the starch-containing material at a temperature above the initial gelatinization temperature using an alpha-amylase and a variant pullulanase of the invention;
b) saccharifying using a glucoamylase;
c) fermenting using a fermenting organism.

In a fourth aspect the present invention relates to compositions comprising the variant pullulanase of the invention and a stabilizer.

The present invention also relates to polynucleotides encoding the variants; nucleic acid constructs, vectors, and host cells comprising the polynucleotides; and methods of producing the variants.

Definitions

Figure 1:
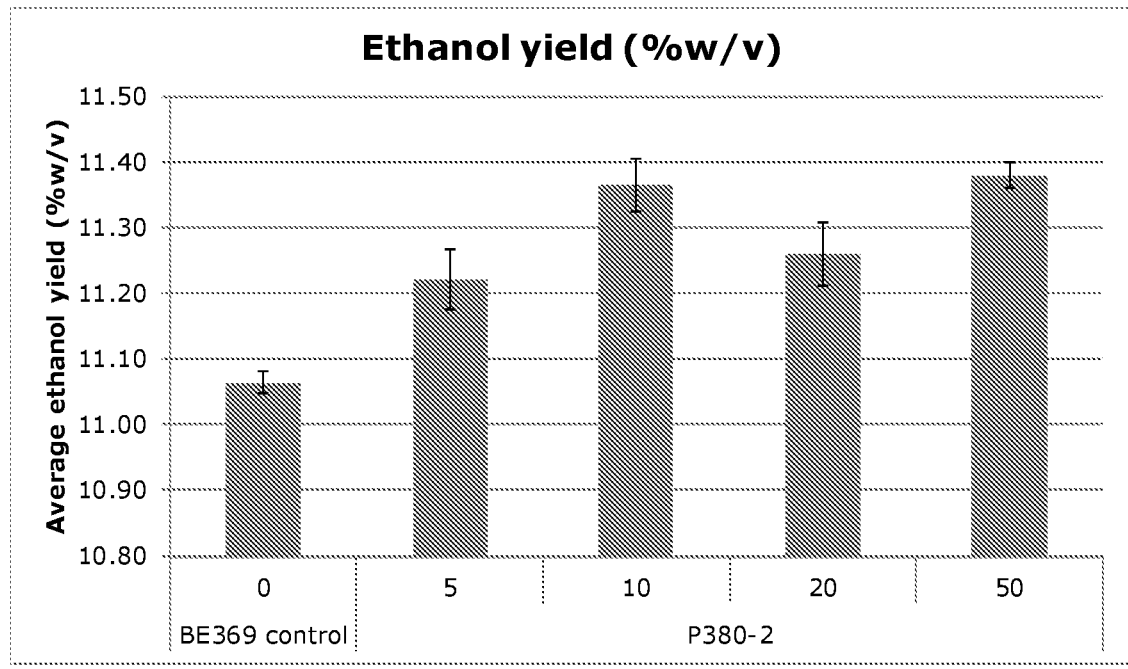
FIG. 1 shows average ethanol yields (in % w/v) for the BE369 amylase only control and four doses of the thermo-stable pullulanase, P380-2, in an 80° C. liquefaction and standard lab scale fermentation assays. All of the P380-2 doses produced statistically more ethanol than the BE369 control as determined by JMP software. The percent ethanol increase with the control set to 100% was 1.4-2.9% for the P380-2 treatments.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Catalytic domain: The term "catalytic domain" means the region of an enzyme containing the catalytic machinery of the enzyme.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide having one or more (e.g., several) amino acids absent from the amino and/or carboxyl terminus of a mature polypeptide or domain; wherein the fragment has pullulanas activity.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). An isolated substance may be present in a fermentation broth sample; e.g. a host cell may be genetically modified to express the polypeptide of the invention. The fermentation broth from that host cell will comprise the isolated polypeptide.

Mature polypeptide: The term "mature polypeptide" means a polypeptide in its final form following translation and any post-translational modifications, such as N-terminal processing, C-terminal truncation, glycosylation, phosphorylation, etc. It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having protease activity.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Pullulanase: The term "pullulanase" means a starch debranching enzyme having pullulan 6-glucano-hydrolase activity (EC 3.2.1.41) that catalyzes the hydrolysis the α-1,6-glycosidic bonds in pullulan, releasing maltotriose with reducing carbohydrate ends. For purposes of the present invention, pullulanase activity can be determined according to the procedure described in the Examples. In the context of the present invention the variant pullulanases have increased thermo-activity. Increased thermo-activity was determined as relative activity when measured at 76-81.5° C. relative to activity at 65° C. or 75° C. using the PHADEBAS assay as described in the examples.

In particular the pullulanase variants suitable for the process of the invention have at least 30% relative activity when measured at 76° C. relative to activity at 65° C., more particularly at least 40%, more particularly at least 50%, more particularly at least 60%, more particularly at least 70%, more particularly at least 80%, more particularly at least 90%, more particularly at least 95%. More particularly pullulanase variants suitable for the process of the invention have at least 50% relative activity when measured at 79° C. relative to activity at 75° C., more particularly at least 60%, more particularly at least 70%, more particularly at least 80%, more particularly at least 90%, more particularly at least 95%.

Wild-type Pullulanase: The term "wild-type" pullulanase means a pullulanase expressed by a naturally occurring microorganism, such as a bacterium, yeast, or filamentous fungus found in nature.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EDNAFULL62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Stringency conditions: The term "very low stringency conditions" means for probes of at least 100 nucleotides in length, prehybridization and hybridization at 42° C. in 5× SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2× SSC, 0.2% SDS at 45° C.

The term "low stringency conditions" means for probes of at least 100 nucleotides in length, prehybridization and hybridization at 42° C. in 5× SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2× SSC, 0.2% SDS at 50° C.

The term "medium stringency conditions" means for probes of at least 100 nucleotides in length, prehybridization and hybridization at 42° C. in 5× SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2× SSC, 0.2% SDS at 55° C.

The term "medium-high stringency conditions" means for probes of at least 100 nucleotides in length, prehybridization and hybridization at 42° C. in 5× SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2× SSC, 0.2% SDS at 60° C.

The term "high stringency conditions" means for probes of at least 100 nucleotides in length, prehybridization and hybridization at 42° C. in 5× SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2× SSC, 0.2% SDS at 65° C.

The term "very high stringency conditions" means for probes of at least 100 nucleotides in length, prehybridization and hybridization at 42° C. in 5× SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2× SSC, 0.2% SDS at 70° C.]

Subsequence: The term "subsequence" means a polynucleotide having one or more (e.g., several) nucleotides absent from the 5' and/or 3' end of a mature polypeptide coding sequence; wherein the subsequence encodes a fragment having pullulanase activity.

S8A Protease: The term "S8A protease" means an S8 protease belonging to subfamily *A. Subtilisins*, EC 3.4.21.62, are a subgroup in subfamily S8A, however, the present S8A protease from *Thermococcus* sp PK is a subtilisin-like protease, which has not yet been included in the IUBMB classification system. The S8A protease according to the invention hydrolyses the substrate Suc-Ala-Ala-Pro-Phe-pNA. The release of p-nitroaniline (pNA) results in an increase of absorbance at 405 nm and is proportional to the enzyme activity. pH optimum=pH 8, and Temperature optimum=60° C.

Variant: The term "variant" means a polypeptide having pullulanase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. In describing variants, the nomenclature described below is adapted for ease of reference. The accepted IUPAC single letter or three letter amino acid abbreviations are employed.

In the context of the present invention the variant pullulanases has increased thermo-activity. Increased thermo-activity was determined as relative activity when measured at 76-79° C. relative to activity at 65° C. using the PHADEBAS assay as described in the examples, or measured at 78-81.5° C. relative to activity at 75° C. using the PHADEBAS assay as described in the examples.

In particular the pullulanase variants suitable for the process of the invention have at least 30% relative activity when measured at 76° C. relative to activity at 65° C., more particularly at least 40%, more particularly at least 50%, more particularly at least 60%, more particularly at least 70%, more particularly at least 80%, more particularly at least 90%, more particularly at least 95%. More particularly pullulanase variants suitable for the process of the invention have at least 50% relative activity when measured at 79° C. relative to activity at 75° C., more particularly at least 60%, more particularly at least 70%, more particularly at least 80%, more particularly at least 90%, more particularly at least 95%.

Conventions for Designation of Variants

For purposes of the present invention, the mature hybrid pullulanase polypeptide disclosed as SEQ ID NO: 3 is used to determine the corresponding amino acid residue in another pullulanase. The amino acid sequence of another pullulanase is aligned with the mature polypeptide disclosed as SEQ ID NO: 3, and based on the alignment, the amino acid position number corresponding to any amino acid residue in the mature polypeptide disclosed as SEQ ID NO: 3 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another pullulanase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When the other enzyme has diverged from the polypeptide of SEQ ID NO: 3 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviations are employed.

Substitutions. For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195 | 195 195a 195b |
| G | G - K - A |

Multiple alterations. Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different alterations. Where different alterations can be introduced at a position, the different alterations are separated by a comma, e.g., "Arg170Tyr,Glu" represents a substitution of arginine at position 170 with tyrosine and glutamic acid. Thus, "Tyr167Gly,Ala+Arg170Gly,Ala" designates the following variants:
"Tyr167Gly+Arg170Gly", "Tyr167Gly+Arg170Ala", "Tyr167Ala+Arg170Gly", and "Tyr167Ala+Arg170Ala".

Throughout the present description in some embodiments the variants of the invention have been described by giving the amino acid present at the specified position in SEQ ID NO: 3 as well as the amino acid present after substitution. This does not mean that the starting amino acid in the specified position cannot be a different one. The starting amino acid in a specific position of course depends on the choice of the parent pullulanase. The essential feature of the present invention is the resulting amino acid present after the substitution. In case the parent pullulanase already has the desired amino acid in a specific position this means that it should be maintained. E.g., the parent pullulanase disclosed as SEQ ID NO: 3 has alanine in position 492. Therefore according to the invention position 492 should also have 492A in the variants according to the invention.

DETAILED DESCRIPTION OF THE INVENTION

The present invention relates to variant pullulanases derived from a hybrid parent pullulanase. The hybrid parent pullulanase was constructed by fusing the N-terminal amino acids 1-451 from a wild type pullulanase (SEQ ID NO: 1) isolated from *Bacillus acidopullulyticus* with the C-terminal amino acids 452-828 from another wild type pullulanase (SEQ ID NO: 2) isolated from *Bacillus deramificans*. The resulting hybrid pullulanase, disclosed as SEQ ID NO: 3 herein, was used as the parent pullulanase. The polynucleotide sequence encoding the parent pullulanase is included herein as SEQ ID NO: 4, wherein nucleotides 1-99 encode a signal peptide, and nucleotides 100-2583 encode the mature polypeptide disclosed in SEQ ID NO: 3.

The variants according to the present invention have improved properties compared to the parent. The improved properties are in one embodiment increased thermo-activity. The positions to be substituted in order to obtain increased thermo-activity will be described in detail below. The increase in thermo-activity may be determined as relative activity measured in the range of 65-81.5° C., pH 5.0 by the PHADEBAS assay described herein in the pullulanase assay section. In a particular embodiment the variants according to the invention have at least 30% relative activity when measured at 76° C. relative to activity at 65° C. In another embodiment the variants have at least 50% relative activity when measured at 78° C. relative to activity at 65° C. In another embodiment the variants have at least 70% relative activity when measured at 78° C. relative to activity at 75° C. In another embodiment the variants have at least 70% relative activity when measured at 79° C. relative to activity at 75° C.

In one aspect the present invention therefore relates to a pullulanase variant, wherein the variant comprises at least one of the following combinations of substitutions:
368G+393A+431E+432F+492A,S+610R+624S+631S+632C; 368G+393A+431E+432F+492A,S+610R+624S+631S+632C+20G+28K+80Y+187R+310A+311K+387L+459G+586S+699R+798R; 222P+252A+256R+368G+393A+431E+432F+492A,S+610R+624S+631S+632C; 222P+252A+256R+368G+393A+431E+432F+492A,S+610R+624S+631S+632C+20G+28K+80Y+187R+310A+311K+387L+459G+586S+699R+798R;
wherein the variant has pullulanase activity, and wherein the variants have at least 85%, at least 90%, at least 95%, at least 96%, at least 97%, at least 98%, or at least 99%, but less than 100% sequence identity to the polypeptide of SEQ ID NO: 3.

In another aspect the present invention relates to a pullulanase variant, wherein the variant comprises at least one of the following combinations of substitutions:
N368G+N393A+Q431E+L432F+A492A,S+N610R+G624S+T631S+S632C; N368G+N393A+Q431E+L432F+A492A,S+N610R+G624S+T631S+S632C+N20G+Y28K+H80Y+Q187R+E310A+D311K+Q387L+Q459G+D586S+E699R+S798R; N222P+Q252A+Q256R+N368G+N393A+Q431E+L432F+A492A,S+N610R+G624S+T631S+S632C; N222P+Q252A+Q256R+N368G+N393A+Q431E+L432F+A492A, S+N610R+G624S+T631S+S632C+N20G+Y28K+H80Y+Q187R+E310A+D311K+Q387L+Q459G+D586S+E699R+S798R;
wherein the variant has pullulanase activity, and wherein the variants have at least 85%, at least 90%, at least 95%, at least 96%, at least 97%, at least 98%, or at least 99%, but less than 100% sequence identity to the polypeptide of SEQ ID NO: 3.

The variants according to the invention have at least 30% relative pullulanase activity when measured at 76° C. relative to activity at 65° C.

In one embodiment the invention therefore relates to a pullulanase variant, wherein the variant comprises the following combination of substitutions:
N368G+N393A+Q431E+L432F+A492A,S+N610R+G624S+T631S+S632C; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein the variant has at least 30% relative pullulanase activity when measured at 76° C. relative to activity at 65° C.

In another embodiment the invention therefore relates to a pullulanase variant, wherein the variant comprises the following combination of substitutions:

N368G+N393A+Q431E+L432 F+A492A,S+N610R+G624S+T631S+S632C+N20G+Y28K+H80Y+Q187R+E310A+D311K+Q387L+Q459G+D586S+E699R+S798R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3 and wherein the variant has at least 50% relative activity when measured at 78° C. relative to activity at 65° C.

In another embodiment the invention therefore relates to a pullulanase variant, wherein the variant comprises the following combination of substitutions:

N222P+Q252A+Q256R+N368G+N393A+Q431E+
  L432F+A492A, S+N610R+G624S+T631S+S632C; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein the variant has at least 30% relative pullulanase activity when measured at 76° C. relative to activity at 65° C.

In another embodiment the invention therefore relates to a pullulanase variant, wherein the variant comprises the following combination of substitutions:

N222P+Q252A+Q256R+N368G+N393A+Q431E+
  L432F+A492A, S+N610R+G624S+T631S+S632C+
  N20G+Y28K+H80Y+Q187R+E310A+D311K+
  Q387L+Q459G+D586S+E699R+S798R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein the variant has at least 50% relative activity when measured at 78° C. relative to activity at 65° C.

Starting from one of the above variants, thermo-activity has been further increased. In a still further embodiment the present invention therefore relates to a pullulanase variant, wherein the variant comprises the following combination of substitutions:

N222P+Q252A+Q256R+N368G+N393A+Q431E+
  L432F+A492A,S+N610R+G624S+T631S+S632C+
  N20G+Y28K+H80Y+Q187R+E310A+D311K+
  Q387L+Q459G+D586S+E699R+S798R;

and further the variant comprises at least one of the following combinations of deletions and substitutions:
P30*+V31*+N32*;
P30*+V31*+N32*+D57N+D58P;
Q29G+P30*+V31*+N32*+D57N+D58P;
P30*+V31*+N32*+D57N+D58P+A195G;
P30*+V31*+N32*+D57N+D58P+N197T;
P30*+V31*+N32*+D57N+D58P+N202K;
P30*+V31*+N32*+D57N+D58P+A345P;
P30*+V31*+N32*+D57N+D58P+M402S;
P30*+V31*+N32*+D57N+D58P+F456W;
P30*+V31*+N32*+D57N+D58P+I460V;
P30*+V31*+N32*+D57N+D58P+N479H;
P30*+V31*+N32*+D57N+D58P+I514V;
P30*+V31*+N32*+D57N+D58P+E560R;
P30*+V31*+N32*+D57N+D58P+D615E;
P30*+V31*+N32*+D57N+D58P+A345P+E560R;
P30*+V31*+N32*+D57N+D58P+A345P+I514V;
P30*+V31*+N32*+D57N+D58P+A345P+I460V+I514V;
P30*+V31*+N32*+D57N+D58P+A195G+A345P+
  I460V+I514V;
P30*+V31*+N32*+D57N+D58P+N202K+A345P+E560R;
P30*+V31*+N32*+D57N+D58P+A345P+M402S+E560R;
P30*+V31*+N32*+D57N+D58P+N202K+A345P+
  M402S+E560R;
P30*+V31*+N32*+D57N+D58P+A195G+N202K+
  A345P+M402S+I460V+I514V;
P30*+V31*+N32*+D57N+D58P+F456W;
Q29G+P30*+V31*+N32*+D57N+D58P+A195G+A345P+
  I460V+I514V;
Q29G+P30*+V31*+N32*+D57N+D58P+A195G+N202K+
  A345P+M402S+I460V+I514V;
Q29G+P30*+V31*+N32*+D57N+D58P+A195G+N202K+
  A345P+M402S+I460V+I514V+E560R;
Q29G+P30*+V31*+N32*+D57N+D58P+A195G+N202K+
  A345P+M402S+I460V+I514V+E560R+D615E;
P30*+V31*+N32*+D57N+D58P+A195G+A345P+
  M402S+I460V+I514V+E560R;
P30*+V31*+N32*+D57N+D58P+A195G+A345P+
  M402S+I514V;
P30*+V31*+N32*+D57N+D58P+A195G+A345P;
P30*+V31*+N32*+D57N+D58P+A195G+A345P+
  F456W;
Q29G+P30*+V31*+N32*+D57N+D58P+A195G+A345P+
  M402S+F456W+I460V+I514V;
P30*+V31*+N32*+D57N+D58P+N479H;
P30*+V31*+N32*+D57N+D58P+A195G+A345P+
  M402S+F456W+I460V+I514V+E560R;
P30*+V31*+N32*+D57N+D58P+A195G+A345P+
  M402S+I460V+N479H+I514V+E560R;
P30*+V31*+N32*+D57N+D58P+N197T+A345P+
  M402S+I460V+I514V+E560R;
Q29G+P30*+V31*+N32*+D57N+D58P+A195G+A252I+
  N202K+A345P+M402S+I460V+I514V+E560R;
Q29G+P30*+V31*+N32*+D57N+D58P+A195G+N197T+
  N202K+A345P+M402S+I460V+I514V+E560R;
Q29G+P30*+V31*+N32*+D57N+D58P+A195G+N202K+
  A345P+M402S+F456W+I460V+I514V+E560R;
Q29G+P30*+V31*+N32*+D57N+D58P+A195G+N197T+
  A345P+M402S+F456W+I460V+I514V+E560R;
Q29G+P30*+V31*+N32*+D57N+D58P+A195G+A345P+
  M402S+F456W+I460V+N479H+I514V+E560R;
Q29G+P30*+V31*+N32*+D57N+D58P+A195G+N197T+
  N202K+A345P+M402S+F456W+I460V+I514V+
  E560R
Q29G+P30*+V31*+N32*+D57N+D58P+A195G+N202K+
  A345P+M402S+F456W+I460V+N479H+I514V+
  E560R
Q29G+P30*+V31*+N32*+D57N+D58P+A195G+N197T+
  N202K+A345P+M402S+F456W+I460V+N479H+
  I514V+E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 50%, particularly at least 60%, more particularly at least 70%, even more particularly at least 80% relative activity when measured at 78° C. relative to activity at 65° C.

In more particular embodiments the present invention relates to pullulanase variants, wherein the variants comprise the following combination of substitutions:

N222P+Q252A+Q256R+N368G+N393A+Q431E+
  L432F+A492A,S+N610R+G624S+T631S+S632C+
  N20G+Y28K+H80Y+Q187R+E310A+D311K+
  Q387L+Q459G+D586S+E699R+S798R;

and further the variant comprises at least one of the following combinations of substitutions:

Q29G+P30*+V31*+N32*+D57N+D58P+A195G+N202K+
A345P+M402S+I460V+I514V+E560R;
Q29G+P30*+V31*+N32*+D57N+D58P+A195G+N202K+
A345P+M402S+F456W+I460V+I514V+E560R;
Q29G+P30*+V31*+N32*+D57N+D58P+A195G+N197T+
A345P+M402S+F456W+I460V+I514V+E560R;
Q29G+P30*+V31*+N32*+D57N+D58P+A195G+A345P+
M402S+F456W+I460V+N479H+I514V+E560R; Q29G+
P30*+V31*+N32*+D57N+D58P+A195G+N197T+
N202K+A345P+M402S+F456W+I460V+I514V+
E560R;
Q29G+P30*+V31*+N32*+D57N+D58P+A195G+N202K+
A345P+M402S+F456W+I460V+N479H+I514V+
E560R;
Q29G+P30*+V31*+N32*+D57N+D58P+A195G+N
197T+N202K+A345P+M402S+F456W+I460V+
N479H+I514V+E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 78° C. relative to activity at 75° C.

In one particular embodiment the present invention relates to pullulanase variants, wherein the variants comprise the following combination of substitutions:
N222P+Q252A+Q256R+N368G+N393A+Q431E+
L432F+A492A, S+N610R+G624S+T631S+S632C+
N20G+Y28K+H80Y+Q187R+E310A+D311K+
Q387L+Q459G+D586S+E699R+S798R;
and further the variant comprises the following combinations of substitutions:
Q29G+P30*+V31*+N32*+D57N+D58P+A195G+N202K+
A345P+M402S+I460V+I514V+E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 78° C. relative to activity at 75° C.

In one particular embodiment the present invention relates to pullulanase variants, wherein the variants comprise the following combination of substitutions:
N222P+Q252A+Q256R+N368G+N393A+Q431E+
L432F+A492A, S+N610R+G624S+T631S+S632C+
N20G+Y28K+H80Y+Q187R+E310A+D311K+
Q387L+Q459G+D586S+E699R+S798R;
and further the variant comprises the following combinations of substitutions:
Q29G+P30*+V31*+N32*+D57N+D58P+A195G+N202K+
A345P+M402S+F456W+I460V+I514V+E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 78° C. relative to activity at 75° C.

In one particular embodiment the present invention relates to pullulanase variants, wherein the variants comprise the following combination of substitutions:
N222P+Q252A+Q256R+N368G+N393A+Q431E+
L432F+A492A,S+N610R+G624S+T631S+S632O+
N20G+Y28K+H80Y+Q187R+E310A+D311K+
Q387L+Q459G+D586S+E699R+S798R;
and further the variant comprises the following combinations of substitutions: Q29G+P30*+V31*+N32*+D57N+
D58P+A195G+N197T+A345P+M402S+F456W+I460V+
I514V+E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 79° C. relative to activity at 75° C.

In one particular embodiment the present invention relates to pullulanase variants, wherein the variants comprise the following combination of substitutions:
N222P+Q252A+Q256R+N368G+N393A+Q431E+
L432F+A492A, S+N610R+G624S+T631S+S632C+
N20G+Y28K+H80Y+Q187R+E310A+D311K+
Q387L+Q459G+D586S+E699R+S798R;
and further the variant comprises the following combinations of substitutions:
Q29G+P30*+V31*+N32*+D57N+D58P+A195G+A345P+
M402S+F456W+I460V+N479H+I514V+E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 79° C. relative to activity at 75° C.

In one particular embodiment the present invention relates to pullulanase variants, wherein the variants comprise the following combination of substitutions:
N222P+Q252A+Q256R+N368G+N393A+Q431E+
L432F+A492A, S+N610R+G624S+T631S+S632C+
N20G+Y28K+H80Y+Q187R+E310A+D311K+
Q387L+Q459G+D586S+E699R+S798R;
sand further the variant comprises the following combinations of substitutions:
Q29G+P30*+V31*+N32*+D57N+D58P+A195G+N197T+
N202K+A345P+M402S+F456W+I460V+I514V+
E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 79° C. relative to activity at 75° C.

In one particular embodiment the present invention relates to pullulanase variants, wherein the variants comprise the following combination of substitutions:
N222P+Q252A+Q256R+N368G+N393A+Q431E+
L432F+A492A, S+N610R+G624S+T631S+S632C+
N20G+Y28K+H80Y+Q187R+E310A+D311K+
Q387L+Q459G+D586S+E699R+S798R;
and further the variant comprises the following combinations of substitutions:
Q29G+P30*+V31*+N32*+D57N+D58P+A195G+N202K+
A345P+M402S+F456W+I460V+N479H+I514V+
E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 79° C. relative to activity at 75° C.

In one particular embodiment the present invention relates to pullulanase variants, wherein the variants comprise the following combination of substitutions:

N222P+Q252A+Q256R+N368G+N393A+Q431E+
L432F+A492A,S+N610R+G624S+T631S+S632C+
N20G+Y28K+H80Y+Q187R+E310A+D311K+
Q387L+Q459G+D586S+E699R+S798R;
and further the variant comprises the following combinations of substitutions:
Q29G+P30*+V31*+N32*+D57N+D58P+A195G+N
197T+N202K+A345P+M402S+F456W+I460V+
N479H+I514V+E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 79° C. relative to activity at 75° C.

Polynucleotides

The present invention also relates to polynucleotides encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* crylIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin or tetracycline resistance.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any Bacillus cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a Pseudomonas cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

Methods of Production

The present invention also relates to methods of producing a variant, comprising: (a) cultivating a host cell of the present invention under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art. For example, an enzyme assay may be used to determine the activity of the variant. See the Assay section for suitable pullulanase activity assays.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the variant is not recovered, but rather a host cell of the present invention expressing the variant is used as a source of the variant.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The present invention also relates to compositions comprising a pullulanase variant of the invention and a suitable stabilizer.

The compositions may comprise the pullulanase variant as the major enzymatic component, e.g., a mono-component composition. Alternatively, the compositions may comprise multiple enzymatic activities, such as one or more (e.g., several) enzymes selected from the group consisting of alpha-amylase, glucoamylase, beta-amylase, protease.

The compositions may be prepared in accordance with methods known in the art and may be in the form of a liquid or a dry composition. The compositions may be stabilized in accordance with methods known in the art.

Examples are given below of preferred uses of the compositions of the present invention. In a particular embodiment the composition further comprises an alpha-amylase.

The alpha-amylase is preferably a bacterial acid stable alpha-amylase. Particularly the alpha-amylase is from an *Exiguobacterium* sp. or a *Bacillus* sp. such as e.g., *Bacillus stearothermophilus* or *Bacillus licheniformis*.

In an embodiment the alpha-amylase is from the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 5 herein.

In an embodiment the *Bacillus stearothermophilus* alpha-amylase has a double deletion of two amino acids in the region from position 179 to 182, more particularly a double deletion at positions I181+G182, R179+G180, G180+I181, R179+I181, or G180+G182, preferably I181+G182, and optionally a N193F substitution, (using SEQ ID NO: 5 for numbering).

In an embodiment the *Bacillus stearothermophilus* alpha-amylase has a substitution at position S242, preferably S242Q substitution.

In an embodiment the *Bacillus stearothermophilus* alpha-amylase has a substitution at position E188, preferably E188P substitution.

In an embodiment the alpha-amylase is selected from the group of *Bacillus stearothermophilus* alpha-amylase variants with the following mutations in addition to a double deletion in the region from position 179 to 182, particularly I181*+G182* and optionally N193F:

V59A+Q89R+G112D+E129V+K177L+R179E+K220P+N224L+Q254S;
V59A+Q89R+E129V+K177L+R179E+H208Y+K220P+N224L+Q254S;
V59A+Q89R+E129V+K177L+R179E+K220P+N224L+Q254S+D269E+D281N;
V59A+Q89R+E129V+K177L+R179E+K220P+N224L+Q254S+I270L;
V59A+Q89R+E129V+K177L+R179E+K220P+N224L+Q254S+H274K;
V59A+Q89R+E129V+K177L+R179E+K220P+N224L+Q254S+Y276F;
V59A+E129V+R157Y+K177L+R179E+K220P+N224L+S242Q+Q254S;
V59A+E129V+K177L+R179E+H208Y+K220P+N224L+S242Q+Q254S;
V59A+E129V+K177L+R179E+K220P+N224L+S242Q+Q254S;
V59A+E129V+K177L+R179E+K220P+N224L+S242Q+Q254S+H274K;
V59A+E129V+K177L+R179E+K220P+N224L+S242Q+Q254S+Y276F;
V59A+E129V+K177L+R179E+K220P+N224L+S242Q+Q254S+D281N;
V59A+E129V+K177L+R179E+K220P+N224L+S242Q+Q254S+M284T;
V59A+E129V+K177L+R179E+K220P+N224L+S242Q+Q254S+G416V;
V59A+E129V+K177L+R179E+K220P+N224L+Q254S;
V59A+E129V+K177L+R179E+K220P+N224L+Q254S+M284T;
A91 L+M961+E129V+K177L+R179E+K220P+N224L+S242Q+Q254S;
E129V+K177L+R179E;
E129V+K177L+R179E+K220P+N224L+S242Q+Q254S;
E129V+K177L+R179E+K220P+N224L+S242Q+Q254S+Y276F+L427M;
E129V+K177L+R179E+K220P+N224L+S242Q+Q254S+M284T;
E129V+K177L+R179E+K220P+N224L+S242Q+Q254S+N376*+I377*;
E129V+K177L+R179E+K220P+N224L+Q254S;
E129V+K177L+R179E+K220P+N224L+Q254S+M284T;
E129V+K177L+R179E+S242Q;
E129V+K177L+R179V+K220P+N224L+S242Q+Q254S;
K220P+N224L+S242Q+Q254S;
M284V;
V59A Q89R+E129V+K177L+R179E+Q254S+M284V.

In an embodiment the alpha-amylase is selected from the group of *Bacillus stearothermophilus* alpha-amylase variants with the following mutations:

I181*+G182*+N193F+E129V+K177L+R179E;
I181*+G182*+N193F+V59A+Q89R+E129V+K177L+R179E+H208Y+K220P+N224L+Q254S;
I181*+G182*+N193F+V59A Q89R+E129V+K177L+R179E+Q254S+M284V; and
I181*+G182*+N193F+E129V+K177L+R179E+K220P+N224L+S242Q+Q254S (using SEQ ID NO: 5 for numbering).

In an embodiment the alpha-amylase variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 5.

It should be understood that when referring to *Bacillus stearothermophilus* alpha-amylase and variants thereof they are normally produced in truncated form. In particular, the truncation may be so that the *Bacillus stearothermophilus* alpha-amylase shown in SEQ ID NO: 3 in WO 99/19467 or SEQ ID NO: 5 herein, or variants thereof, are truncated in the C-terminal preferably to have around 490 amino acids, such as from 482-493 amino acids. Preferably the *Bacillus stearothermophilus* variant alpha-amylase is truncated, preferably after position 484 of SEQ ID NO: 5, particularly after position 485, particularly after position 486, particularly after position 487, particularly after position 488, particularly after position 489, particularly after position 490, particularly after position 491, particularly after position 492, more particularly after position 493.

Protease Present and/or Added During Liquefaction

In a preferred embodiment the enzyme composition of the invention, further comprises a protease.

According to the invention a thermostable protease may optionally be present and/or added during liquefaction together with a variant pullulanase of the invention and an alpha-amylase, such as a thermostable alpha-amylase.

Proteases are classified on the basis of their catalytic mechanism into the following groups: Serine proteases (S), Cysteine proteases (C), Aspartic proteases (A), Metallo proteases (M), and Unknown, or as yet unclassified, proteases (U), see Handbook of Proteolytic Enzymes, A. J. Barrett, N. D. Rawlings, J. F. Woessner (eds), Academic Press (1998), in particular the general introduction part.

In a preferred embodiment the thermostable protease used according to the invention is a "metallo protease" defined as a protease belonging to EC 3.4.24 (metalloendopeptidases); preferably EC 3.4.24.39 (acid metallo proteinases).

To determine whether a given protease is a metallo protease or not, reference is made to the above "Handbook of Proteolytic Enzymes" and the principles indicated therein. Such determination can be carried out for all types of proteases, be it naturally occurring or wild-type proteases; or genetically engineered or synthetic proteases.

Protease activity can be measured using any suitable assay, in which a substrate is employed, that includes peptide bonds relevant for the specificity of the protease in question. Assay-pH and assay-temperature are likewise to be adapted to the protease in question. Examples of assay-pH-values are pH 6, 7, 8, 9, 10, or 11. Examples of assay-temperatures are 30, 35, 37, 40, 45, 50, 55, 60, 65, 70 or 80° C.

Examples of protease substrates are casein, such as Azurine-Crosslinked Casein (AZCL-casein). Two protease assays are described below in the "Materials & Methods"-section, of which the so-called "AZCL-Casein Assay" is the preferred assay.

In an embodiment the thermostable protease has at least 20%, such as at least 30%, such as at least 40%, such as at least 50%, such as at least 60%, such as at least 70%, such as at least 80%, such as at least 90%, such as at least 95%, such as at least 100% of the protease activity of the Protease 196 variant or Protease Pfu determined by the AZCL-casein assay described in the "Materials & Methods" section.

There are no limitations on the origin of the protease used in a process of the invention as long as it fulfills the thermostability properties defined below.

The protease may be a variant of, e.g., a wild-type protease as long as the protease has the thermostability properties defined herein. In a preferred embodiment the thermostable protease is a variant of a metallo protease as defined above. In an embodiment the thermostable protease used in a process of the invention is of fungal origin, such as a fungal metallo protease, such as a fungal metallo protease derived from a strain of the genus *Thermoascus*, preferably a strain of *Thermoascus aurantiacus*, especially *Thermoascus aurantiacus* CGMCC No. 0670 (classified as EC 3.4.24.39).

In an embodiment the thermostable protease is a variant of the mature part of the metallo protease shown in SEQ ID NO: 2 disclosed in WO 2003/048353 or the mature part of SEQ ID NO: 1 in WO 2010/008841 and shown as SEQ ID NO: 6 herein further with mutations selected from below list:

S5*+D79L+S87P+A112P+D142L;
D79L+S87P+A112P+T124V+D142L;
S5*+N26R+D79L+S87P+A112P+D142L;
N26R+T46R+D79L+S87P+A112P+D142L;
T46R+D79L+S87P+T116V+D142L;
D79L+P81R+S87P+A112P+D142L;
A27K+D79L+S87P+A112P+T124V+D142L;
D79L+Y82F+S87P+A112P+T124V+D142L;
D79L+Y82F+S87P+A112P+T124V+D142L;
D79L+S87P+A112P+T124V+A126V+D142L;
D79L+S87P+A112P+D142L;
D79L+Y82F+S87P+A112P+D142L;
S38T+D79L+S87P+A112P+A126V+D142L;
D79L+Y82F+S87P+A112P+A126V+D142L;
A27K+D79L+S87P+A112P+A126V+D142L;
D79L+S87P+N98C+A112P+G135C+D142L;
D79L+S87P+A112P+D142L+T141C+M161C;
S36P+D79L+S87P+A112P+D142L;
A37P+D79L+S87P+A112P+D142L;
S49P+D79L+S87P+A112P+D142L;
S50P+D79L+S87P+A112P+D142L;
D79L+S87P+D104P+A112P+D142L;
D79L+Y82F+S87G+A112P+D142L;
S70V+D79L+Y82F+S87G+Y97W+A112P+D142L;
D79L+Y82F+S87G+Y97W+D104P+A112P+D142L;
S70V+D79L+Y82F+S87G+A112P+D142L;
D79L+Y82F+S87G+D104P+A112P+D142L;
D79L+Y82F+S87G+A112P+A126V+D142L;
Y82F+S87G+S70V+D79L+D104P+A112P+D142L;
Y82F+S87G+D79L+D104P+A112P+A126V+D142L;
A27K+D79L+Y82F+S87G+D104P+A112P+A126V+D142L;
A27K+Y82F+S87G+D104P+A112P+A126V+D142L;
A27K+D79L+Y82F+D104P+A112P+A126V+D142L;
A27K+Y82F+D104P+A112P+A126V+D142L;
A27K+D79L+S87P+A112P+D142L;
D79L+S87P+D142L.

In an preferred embodiment the thermostable protease is a variant of the metallo protease disclosed as the mature part of SEQ ID NO: 2 disclosed in WO 2003/048353 or the mature part of SEQ ID NO: 1 in WO 2010/008841 or SEQ ID NO: 6 herein with the following mutations:

D79L+S87P+A112P+D142L;
D79L+S87P+D142L; or
A27K+D79L+Y82F+S87G+D104P+A112P+A126V+D142L.

In an embodiment the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841 or SEQ ID NO: 6 herein.

The thermostable protease may also be derived from any bacterium as long as the protease has the thermo-stability properties defined according to the description.

In an embodiment the thermostable protease is derived from a strain of the bacterium *Pyrococcus*, such as a strain of *Pyrococcus furiosus* (pfu protease).

In an embodiment the protease is the one shown as SEQ ID NO: 1 in U.S. Pat. No. 6,358,726-B1 (Takara Shuzo Company) or SEQ ID NO: 7 herein.

In another embodiment the thermostable protease is one disclosed in SEQ ID NO: 7 herein or a protease having at least 80% identity, such as at least 85%, such as at least 90%, such as at least 95%, such as at least 96%, such as at least 97%, such as at least 98%, such as at least 99% identity to SEQ ID NO: 1 in U.S. Pat. No. 6,358,726-B1 or SEQ ID NO: 7 herein. The *Pyroccus furiosus* protease can be purchased from Takara Bio, Japan.

Thus in a particular embodiment of the invention the enzyme composition further comprises a protease selected from a *Pyrococcus* sp protease, e.g. a *Pyrococcus furiosus* protease (SEQ ID NO: 7), a *Thermococcus* sp. S8A protease (SEQ ID NO: 8), e.g. a *Thermococcus litoralis* 58A protease, or a *Thermoascus* sp protease, e.g., a *Thermoascus aurantiacus* protease, particularly a variant of a *Thermoascus aurantiacus* protease, shown as SEQ ID NO: 6, comprising one of the specific combinations of substitutions in the D79L+S87P+A112P+D142L;
D79L+S87P+D142L; or
A27K+D79L+Y82F+S87G+D104P+A112P+A126V+ D142L.

In an embodiment the composition of the invention comprises:
  i) a *Bacillus stearothermophilus* alpha-amylase, or a variant thereof;
  ii) a variant pullulanase of the invention;
  iii) optionally a protease; and
wherein the ratio between alpha-amylase and protease is in the range from 1:1 and 1:50 (micro gram alpha-amylase: micro gram protease).

In an embodiment the ratio between alpha-amylase and protease is in the range between 1:3 and 1:40, such as around 1:4 (micro gram alpha-amylase: micro gram protease).

In an embodiment the ratio between alpha-amylase and pullulanase is between 1:1 and 1:10, such as around 1:2.5 or 1:5 (micro gram alpha-amylase: micro gram pullulanase).

The pullulanase may according to the invention be added in an effective amount which include the preferred amount of about 2-100 micro gram enzyme protein per gram DS, preferably 5-50 micro gram enzyme protein per gram DS. Pullulanase activity may be determined as NPUN. An Assay for determination of NPUN is described in the assay section.

In a particular embodiment the variant pullulanase is selected from pullulanase variants, wherein the variants comprise the following combination of substitutions:
  N222P+Q252A+Q256R+N368G+N393A+Q431E+ L432F+A492A, S+N610R+G624S+T631S+S632C+ N20G+Y28K+H80Y+Q187R+E310A+D311K+ Q387L+Q459G+D586S+E699R+S798R;
and further the variant comprises at least one of the following combinations of substitutions:
  Q29G+P30*+V31*+N32*+D57N+D58P+A195G+ N202K+A345P+M402S+I460V+I514V+E560R;
  Q29G+P30*+V31*+N32*+D57N+D58P+A195G+ N202K+A345P+M402S+F456W+I460V+I514V+ E560R;
  Q29G+P30*+V31*+N32*+D57N+D58P+A195G+ N197T+A345P+M402S+F456W+I460V+I514V+ E560R;
  Q29G+P30*+V31*+N32*+D57N+D58P+A195G+ A345P+M402S+F456W+I460V+N479H+I514V+ E560R; and
wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 78° C. relative to activity at 75° C.

In a particular embodiment the variant pullulanase is selected from pullulanase variants, wherein the variants comprise the following combination of substitutions:
  N222P+Q252A+Q256R+N368G+N393A+Q431E+L432 F+A492A, S+N610R+G624S+T631S+S632C+N20G+ Y28K+H80Y+Q187R+E310A+D311K+Q387L+ Q459G+D586S+E699R+S798R;
and further the variant comprises the following combinations of substitutions:
  Q29G+P30*+V31*+N32*+D57N+D58P+A195G+N202K+ A345P+M402S+I460V+I514V+E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 78° C. relative to activity at 75° C.

In a particular embodiment the variant pullulanase is selected from pullulanase variants, wherein the variants comprise the following combination of substitutions:
  N222P+Q252A+Q256R+N368G+N393A+Q431E+ L432F+A492A, S+N610R+G624S+T631S+S632C+ N20G+Y28K+H80Y+Q187R+E310A+D311K+ Q387L+Q459G+D586S+E699R+S798R;
and further the variant comprises the following combinations of substitutions:
  Q29G+P30*+V31*+N32*+D57N+D58P+A195G+N202K+ A345P+M402S+F456W+I460V+I514V+E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 78° C. relative to activity at 75° C.

In a particular embodiment the variant pullulanase is selected from pullulanase variants, wherein the variants comprise the following combination of substitutions:
  N222P+Q252A+Q256R+N368G+N393A+Q431E+ L432F+A492A, S+N610R+G624S+T631S+S632C+ N20G+Y28K+H80Y+Q187R+E310A+D311K+ Q387L+Q459G+D586S+E699R+S798R;
and further the variant comprises the following combinations of substitutions:
  Q29G+P30*+V31*+N32*+D57N+D58P+A195G+N197T+ A345P+M402S+F456W+I460V+I514V+E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 79° C. relative to activity at 75° C.

In a particular embodiment the variant pullulanase is selected from pullulanase variants, wherein the variants comprise the following combination of substitutions:
  N222P+Q252A+Q256R+N368G+N393A+Q431E+ L432F+A492A, S+N610R+G624S+T631S+S632C+ N20G+Y28K+H80Y+Q187R+E310A+D311K+ Q387L+Q459G+D586S+E699R+S798R;
and further the variant comprises the following combinations of substitutions:
  Q29G+P30*+V31*+N32*+D57N+D58P+A195G+A345P+ M402S+F456W+I460V+N479H+I514V+E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 79° C. relative to activity at 75° C.

In a particular embodiment the variant pullulanase is selected from pullulanase variants, wherein the variants comprise the following combination of substitutions:

N222P+Q252A+Q256R+N368G+N393A+Q431E+ L432F+A492A, S+N610R+G624S+T631S+S632C+ N20G+Y28K+H80Y+Q187R+E310A+D311K+ Q387L+Q459G+D586S+E699R+S798R;

and further the variant comprises the following combinations of substitutions:

Q29G+P30*+V31*+N32*+D57N+D58P+A195G+N197T+ N202K+A345P+M402S+F456W+I460V+I514V+ E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 79° C. relative to activity at 75° C.

In a particular embodiment the variant pullulanase is selected from pullulanase variants, wherein the variants comprise the following combination of substitutions:

N222P+Q252A+Q256R+N368G+N393A+Q431E+ L432F+A492A, S+N610R+G624S+T631S+S632C+ N20G+Y28K+H80Y+Q187R+E310A+D311K+ Q387L+Q459G+D586S+E699R+S798R;

and further the variant comprises the following combinations of substitutions:

Q29G+P30*+V31*+N32*+D57N+D58P+A195G+N202K+ A345P+M402S+F456W+I460V+N479H+1514V+ E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 79° C. relative to activity at 75° C.

In a particular embodiment the variant pullulanase is selected from pullulanase variants, wherein the variants comprise the following combination of substitutions:

N222P+Q252A+Q256R+N368G+N393A+Q431E+ L432F+A492A,S+N610R+G624S+T631S+S632C+ N20G+Y28K+H80Y+Q187R+E310A+D311K+ Q387L+Q459G+D586S+E699R+S798R;

and further the variant comprises the following combinations of substitutions:

Q29G+P30*+V31*+N32*+D57N+D58P+A195G+N197T+ N202K+A345P+M402S+F456W+I460V+N479H+ 1514V+E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 79° C. relative to activity at 75° C.

Processes of the Invention

The present invention relates to processes for producing fermentation products from starch-containing material. In particular the product is an alcohol, more particularly ethanol.

The inventors have found that an increased ethanol yield can be obtained when a pullanase variant according to the invention, having increased thermo-activity, is present or added during liquefaction together with at least an alpha-amylase.

Process of Producing a Fermentation Product of the Invention

In a particular aspect the invention relates to a process for producing a syrup from starch-containing material comprising the steps of:
a) liquefying the starch-containing material at a temperature above the initial gelatinization temperature using an alpha-amylase and a variant pullulanase of the invention;
b) saccharifying using a glucoamylase.

In another particular aspect the invention relates to processes for producing fermentation products from starch-containing material comprising the steps of:
a) liquefying the starch-containing material at a temperature above the initial gelatinization temperature using:
an alpha-amylase and a variant pullulanase of the invention;
b) saccharifying using a glucoamylase;
c) fermenting using a fermenting organism.

In a preferred embodiment the fermentation product is recovered after fermentation, such as by distillation. In an embodiment the fermentation product is an alcohol, preferably ethanol, especially fuel ethanol, potable ethanol and/or industrial ethanol.

Alpha-Amylases Present and/or Added in Liquefaction

The alpha-amylase added during liquefaction step a) in a process of the invention may be any alpha-amylase. Preferred are bacterial alpha-amylases, which typically are stable at a temperature used in liquefaction.

In an embodiment the alpha-amylase is from a strain of the genus *Exiguobacterium* or *Bacillus*.

In a preferred embodiment the alpha-amylase is from a strain of *Bacillus stearothermophilus*, such as the sequence shown in SEQ ID NO: 3 in WO99/019467 or in SEQ ID NO: 5 herein. In an embodiment the alpha-amylase is the *Bacillus stearothermophilus* alpha-amylase shown in SEQ ID NO: 5 herein, such as one having at least 80%, such as at least 85%, such as at least 90%, such as at least 95%, such as at least 96%, such as at least 97%, such as at least 98%, such as at least 99% identity to SEQ ID NO: 5 herein.

In an embodiment the *Bacillus stearothermophilus* alpha-amylase or variant thereof is truncated, preferably at the C-terminal, preferably truncated to have around 491 amino acids, such as from 480-495 amino acids.

In an embodiment the *Bacillus stearothermophilus* alpha-amylase has a double deletion of two amino acids in the region from position 179 to 182, more particularly a double deletion at positions I181+G182, R179+G180, G180+I181, R179+I181, or G180+G182, preferably I181+G182, and optionally a N193F substitution, (using SEQ ID NO: 5 for numbering).

In an embodiment the *Bacillus stearothermophilus* alpha-amylase has a substitution at position S242, preferably S242Q substitution.

In an embodiment the *Bacillus stearothermophilus* alpha-amylase has a substitution at position E188, preferably E188P substitution.

In an embodiment the alpha-amylase is selected from the group of *Bacillus stearothermophilus* alpha-amylase variants with the following mutations in addition to a double deletion in the region from position 179 to 182, particularly I181*+G182*, and optionally N193F.

V59A+Q89R+G112D+E129V+K177L+R179E+K220P+ N224L+Q254S;

V59A+Q89R+E129V+K177L+R179E+H208Y+K220P+ N224L+Q254S;

V59A+Q89R+E129V+K177L+R179E+K220P+N224L+
    Q254S+D269E+D281N;
V59A+Q89R+E129V+K177L+R179E+K220P+N224L+
    Q254S+I270L;
V59A+Q89R+E129V+K177L+R179E+K220P+N224L+
    Q254S+H274K;
V59A+Q89R+E129V+K177L+R179E+K220P+N224L+
    Q254S+Y276F;
V59A+E129V+R157Y+K177L+R179E+K220P+
    N224L+S242Q+Q254S;
V59A+E129V+K177L+R179E+H208Y+K220P+
    N224L+S242Q+Q254S;
59A+E129V+K177L+R179E+K220P+N224L+S242Q+
    Q254S;
V59A+E129V+K177L+R179E+K220P+N224L+
    S242Q+Q254S+H274K;
V59A+E129V+K177L+R179E+K220P+N224L+
    S242Q+Q254S+Y276F;
V59A+E129V+K177L+R179E+K220P+N224L+
    S242Q+Q254S+D281N;
V59A+E129V+K177L+R179E+K220P+N224L+
    S242Q+Q254S+M284T;
V59A+E129V+K177L+R179E+K220P+N224L+
    S242Q+Q254S+G416V;
V59A+E129V+K177L+R179E+K220P+N224L+Q254S;
V59A+E129V+K177L+R179E+K220P+N224L+
    Q254S+M284T;
A91L+M961+E129V+K177L+R179E+K220P+N224L+
    S242Q+Q254S;
E129V+K177L+R179E;
E129V+K177L+R179E+K220P+N224L+S242Q+
    Q254S;
E129V+K177L+R179E+K220P+N224L+S242Q+
    Q254S+Y276F+L427M;
E129V+K177L+R179E+K220P+N224L+S242Q+
    Q254S+M284T;
E129V+K177L+R179E+K220P+N224L+S242Q+
    Q254S+N376*+I377*;
E129V+K177L+R179E+K220P+N224L+Q254S;
E129V+K177L+R179E+K220P+N224L+Q254S+
    M284T;
E129V+K177L+R179E+S242Q;
E129V+K177L+R179V+K220P+N224L+S242Q+
    Q254S;
K220P+N224L+S242Q+Q254S;
M284V;
V59A Q89R+E129V+K177L+R179E+Q254S+M284V.

In a preferred embodiment the alpha-amylase is selected from the group of *Bacillus stearothermophilus* alpha-amylase variants:
I181*+G182*+N193F+E129V+K177L+R179E;
I181*+G182*+N193F+V59A+Q89R+E129V+K177L+
    R179E+H208Y+K220P+N224L+Q254S;
I181*+G182*+N193F+V59A Q89R+E129V+K177L+
    R179E+Q254S+M284V; and
I181*+G182*+N193F+E129V+K177L+R179E+K220P+
    N224L+S242Q+Q254S (using SEQ ID NO: 5 for numbering).

According to the invention the alpha-amylase variant has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 5 herein.

The alpha-amylase may according to the invention be present and/or added in a concentration of 0.1-100 micro gram per gram DS, such as 0.5-50 micro gram per gram DS, such as 1-25 micro gram per gram DS, such as 1-10 micro gram per gram DS, such as 2-5 micro gram per gram DS.

In an embodiment the ratio between alpha-amylase and pullulanase is between 1:1 and 1:10, such as around 1:2.5 or 1:5 (micro gram alpha-amylase: micro gram pullulanase).

The pullulanase may according to the invention be added in an effective amount which include the preferred amount of about 2-100 micro gram enzyme protein per gram DS, preferably 5-50 micro gram enzyme protein per gram DS. Pullulanase activity may be determined as NPUN. An Assay for determination of NPUN is described in the assay section.

In a particular embodiment the variant pullulanase is selected from pullulanase variants, wherein the variants comprise the following combination of substitutions:
N222P+Q252A+Q256R+N368G+N393A+Q431E+
    L432F+A492A, S+N610R+G624S+T631S+S632C+
    N20G+Y28K+H80Y+Q187R+E310A+D311K+
    Q387L+Q459G+D586S+E699R+S798R;
and further the variant comprises at least one of the following combinations of substitutions:
Q29G+P30*+V31*+N32*+D57N+D58P+A195G+N202K+
    A345P+M402S+I460V+I514V+E560R;
Q29G+P30*+V31*+N32*+D57N+D58P+A195G+N202K+
    A345P+M402S+F456W+I460V+I514V+E560R;
Q29G+P30*+V31*+N32*+D57N+D58P+A195G+N197T+
    A345P+M402S+F456W+I460V+I514V+E560R;
Q29G+P30*+V31*+N32*+D57N+D58P+A195G+A345P+
    M402S+F456W+I460V+N479H+I514V+E560R; and
wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 78° C. relative to activity at 75° C.

In a particular embodiment the variant pullulanase is selected from pullulanase variants, wherein the variants comprise the following combination of substitutions:
N222P+Q252A+Q256R+N368G+N393A+Q431E+
    L432F+A492A, S+N610R+G624S+T631S+S632C+
    N20G+Y28K+H80Y+Q187R+E310A+D311K+
    Q387L+Q459G+D586S+E699R+S798R;
and further the variant comprises the following combinations of substitutions:
Q29G+P30*+V31*+N32*+D57N+D58P+A195G+N202K+
    A345P+M402S+I460V+I514V+E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 78° C. relative to activity at 75° C.

In a particular embodiment the variant pullulanase is selected from pullulanase variants, wherein the variants comprise the following combination of substitutions:
N222P+Q252A+Q256R+N368G+N393A+Q431E+
    L432F+A492A, S+N610R+G624S+T631S+S632C+
    N20G+Y28K+H80Y+Q187R+E310A+D311K+
    Q387L+Q459G+D586S+E699R+S798R;
and further the variant comprises the following combinations of substitutions:
Q29G+P30*+V31*+N32*+D57N+D58P+A195G+N202K+
    A345P+M402S+F456W+I460V+I514V+E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 78° C. relative to activity at 75° C.

In a particular embodiment the variant pullulanase is selected from pullulanase variants, wherein the variants comprise the following combination of substitutions:

N222P+Q252A+Q256R+N368G+N393A+Q431E+ L432F+A492A, S+N610R+G624S+T631S+S632C+ N20G+Y28K+H80Y+Q187R+E310A+D311K+ Q387L+Q459G+D586S+E699R+S798R;

and further the variant comprises the following combinations of substitutions:

Q29G+P30*+V31*+N32*+D57N+D58P+A195G+N197T+ A345P+M402S+F456W+I460V+I514V+E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 79° C. relative to activity at 75° C.

In a particular embodiment the variant pullulanase is selected from pullulanase variants, wherein the variants comprise the following combination of substitutions:

N222P+Q252A+Q256R+N368G+N393A+Q431E+ L432F+A492A, S+N610R+G624S+T631S+S632C+ N20G+Y28K+H80Y+Q187R+E310A+D311K+ Q387L+Q459G+D586S+E699R+S798R;

and further the variant comprises the following combinations of substitutions:

Q29G+P30*+V31*+N32*+D57N+D58P+A195G+A345P+ M402S+F456W+I460V+N479H+I514V+E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 79° C. relative to activity at 75° C.

In a particular embodiment the variant pullulanase is selected from pullulanase variants, wherein the variants comprise the following combination of substitutions:

N222P+Q252A+Q256R+N368G+N393A+Q431E+ L432F+A492A, S+N610R+G624S+T631S+S632C+ N20G+Y28K+H80Y+Q187R+E310A+D311K+ Q387L+Q459G+D586S+E699R+S798R;

and further the variant comprises the following combinations of substitutions:

Q29G+P30*+V31*+N32*+D57N+D58P+A195G+N197T+ N202K+A345P+M402S+F456W+I460V+I514V+ E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 79° C. relative to activity at 75° C.

In a particular embodiment the variant pullulanase is selected from pullulanase variants, wherein the variants comprise the following combination of substitutions:

N222P+Q252A+Q256R+N368G+N393A+Q431E+ L432F+A492A,S+N610R+G624S+T631S+S632C+ N20G+Y28K+H80Y+Q187R+E310A+D311K+ Q387L+Q459G+D586S+E699R+S798R;

and further the variant comprises the following combinations of substitutions:

Q29G+P30*+V31*+N32*+D57N+D58P+A195G+N202K+ A345P+M402S+F456W+I460V+N479H+I514V+ E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 79° C. relative to activity at 75° C.

In a particular embodiment the variant pullulanase is selected from pullulanase variants, wherein the variants comprise the following combination of substitutions:

N222P+Q252A+Q256R+N368G+N393A+Q431E+ L432F+A492A,S+N610R+G624S+T631S+S632C+ N20G+Y28K+H80Y+Q187R+E310A+D311K+ Q387L+Q459G+D586S+E699R+S798R;

and further the variant comprises the following combinations of substitutions:

Q29G+P30*+V31*+N32*+D57N+D58P+A195G+N197T+ N202K+A345P+M402S+F456W+I460V+N479H+ I514V+E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 79° C. relative to activity at 75° C.

Protease Present and/or Added During Liquefaction

In a preferred embodiment the processes of the invention, further comprises adding a protease in liquefaction.

According to the invention a thermostable protease may optionally be present and/or added during liquefaction together with a variant pullulanase of the invention and an alpha-amylase, such as a thermostable alpha-amylase.

For more details on suitable proteases see the composition section above.

In an preferred embodiment the thermostable protease is a variant of the metallo protease disclosed as the mature part of SEQ ID NO: 2 disclosed in WO 2003/048353 or the mature part of SEQ ID NO: 1 in WO 2010/008841 or SEQ ID NO: 6 herein with the following mutations:

D79L+S87P+A112P+D142L;
D79L+S87P+D142L; or
A27K+D79L+Y82F+S87G+D104P+A112P+A126V+ D142L.

In an embodiment the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841 or SEQ ID NO: 6 herein.

The thermostable protease may also be derived from any bacterium as long as the protease has the thermo-stability properties defined according to the description.

In an embodiment the thermostable protease is derived from a strain of the bacterium *Pyrococcus*, such as a strain of *Pyrococcus furiosus* (pfu protease).

In an embodiment the protease is the one shown as SEQ ID NO: 1 in U.S. Pat. No. 6,358,726-B1 (Takara Shuzo Company) or SEQ ID NO: 7 herein.

In another embodiment the thermostable protease is one disclosed in SEQ ID NO: 7 herein or a protease having at least 80% identity, such as at least 85%, such as at least 90%, such as at least 95%, such as at least 96%, such as at least 97%, such as at least 98%, such as at least 99% identity to SEQ ID NO: 1 in U.S. Pat. No. 6,358,726-B1 or SEQ ID NO: 7 herein. The *Pyroccus furiosus* protease can be purchased from Takara Bio, Japan.

Thus in a particular embodiment of the invention the enzyme composition further comprises a protease selected from a *Pyrococcus* sp protease, e.g. a *Pyrococcus furiosus* protease (SEQ ID NO: 7), a *Thermococcus* sp. S8A protease (SEQ ID NO: 8), e.g. a *Thermococcus litoralis* 58A protease, or a *Thermoascus* sp protease, e.g., a *Thermoascus aurantiacus* protease, particularly a variant of a *Thermoascus aurantiacus* protease, shown as SEQ ID NO: 6, comprising one of the specific combinations of substitutions in the D79L+S87P+A112P+D142L;
D79L+S87P+D142L; or
A27K+D79L+Y82F+S87G+D104P+A112P+A126V+D142L.

Glucoamylase Present and/or Added in Saccharification and/or Fermentation

A glucoamylase is present and/or added in saccharification and/or fermentation, preferably simultaneous saccharification and fermentation (SSF), in a process of the invention (i.e., oil recovery process and fermentation product production process).

In an embodiment the glucoamylase present and/or added in saccharification and/or fermentation is of fungal origin, preferably from a stain of *Aspergillus*, preferably *A. niger*, *A. awamori*, or *A. oryzae*; or a strain of *Trichoderma*, preferably *T. reesei*; or a strain of *Talaromyces*, preferably *T. emersonii* or a strain of *Trametes*, preferably *T. cingulata*, or a strain of *Pycnoporus*, or a strain of *Gloeophyllum*, such as *G. sepiarium* or *G. trabeum*, or a strain of the *Nigrofomes*.

In an embodiment the glucoamylase is derived from *Talaromyces*, such as a strain of *Talaromyces emersonii*, such as the one shown in SEQ ID NO: 9 herein, In an embodiment the glucoamylase is selected from the group consisting of:
(i) a glucoamylase comprising the polypeptide of SEQ ID NO: 9 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 9 herein.

In an embodiment the glucoamylase is derived from a strain of the genus *Pycnoporus*, in particular a strain of *Pycnoporus sanguineus* described in WO 2011/066576 (SEQ ID NOs 2, 4 or 6), such as the one shown as SEQ ID NO: 4 in WO 2011/066576 or SEQ ID NO: 10 herein.

In an embodiment the glucoamylase is derived from a strain of the genus *Gloeophyllum*, such as a strain of *Gloeophyllum sepiarium* or *Gloeophyllum trabeum*, in particular a strain of *Gloeophyllum* as described in WO 2011/068803 (SEQ ID NO: 2, 4, 6, 8, 10, 12, 14 or 16). In a preferred embodiment the glucoamylase is the *Gloeophyllum sepiarium* shown in SEQ ID NO: 2 in WO 2011/068803 or SEQ ID NO: 11 herein.

In a preferred embodiment the glucoamylase is derived from *Gloeophyllum sepiarium*, such as the one shown in SEQ ID NO: 11 herein. In an embodiment the glucoamylase is selected from the group consisting of:
(i) a glucoamylase comprising the polypeptide of SEQ ID NO: 11 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 11 herein.

In another embodiment the glucoamylase is derived from *Gloeophyllum trabeum* such as the one shown in SEQ ID NO: 12 herein. In an embodiment the glucoamylase is selected from the group consisting of:
(i) a glucoamylase comprising the polypeptide of SEQ ID NO: 12 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 12 herein.

In an embodiment the glucoamylase is derived from a strain of the genus *Trametes*, in particular a strain of *Trametes cingulata* disclosed in WO 2006/069289, and herein as SEQ ID NO: 13.

Glucoamylases may in an embodiment be added to the saccharification and/or fermentation in an amount of 0.0001-20 AGU/g DS, preferably 0.001-10 AGU/g DS, especially between 0.01-5 AGU/g DS, such as 0.1-2 AGU/g DS.

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U, SPIRIZYME™ ULTRA, SPIRIZYME™ EXCEL and AMG™ E (from Novozymes A/S); OPTIDEX™ 300, GC480, GC417 (from DuPont.); AMIGASE™ and AMIGASE™ PLUS (from DSM); G-ZYME™ G900, G-ZYME™ and G990 ZR (from DuPont).

According to a preferred embodiment of the invention the glucoamylase is present and/or added in saccharification and/or fermentation in combination with an alpha-amylase. Examples of suitable alpha-amylase are described below.

Alpha-Amylase Present and/or Added in Saccharification and/or Fermentation

In an embodiment an alpha-amylase is present and/or added in saccharification and/or fermentation in a process of the invention. In a preferred embodiment the alpha-amylase is of fungal or bacterial origin. In a preferred embodiment the alpha-amylase is a fungal acid stable alpha-amylase. A fungal acid stable alpha-amylase is an alpha-amylase that has activity in the pH range of 3.0 to 7.0 and preferably in the pH range from 3.5 to 6.5, including activity at a pH of about 4.0, 4.5, 5.0, 5.5, and 6.0.

In a preferred embodiment the alpha-amylase present and/or added in saccharification and/or fermentation is derived from a strain of the genus *Rhizomucor*, preferably a strain the *Rhizomucor pusillus*, such as one shown in SEQ ID NO: 3 in WO 2013/006756, such as a *Rhizomucor pusillus* alpha-amylase hybrid having an *Aspergillus niger* linker and starch-bonding domain, such as the one shown in SEQ ID NO: 14 herein, or a variant thereof.

In an embodiment the alpha-amylase present and/or added in saccharification and/or fermentation is selected from the group consisting of:
(i) an alpha-amylase comprising the polypeptide of SEQ ID NO: 14 herein;

(ii) an alpha-amylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 14 herein.

In a preferred embodiment the alpha-amylase is a variant of the alpha-amylase shown in SEQ ID NO: 14 having at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 11 for numbering).

In an embodiment the alpha-amylase is derived from a *Rhizomucor pusillus* with an *Aspergillus niger* glucoamylase linker and starch-binding domain (SBD), preferably disclosed as SEQ ID NO: 14 herein, preferably having one or more of the following substitutions: G128D, D143N, preferably G128D+D143N (using SEQ ID NO: 14 for numbering).

In an embodiment the alpha-amylase variant present and/or added in saccharification and/or fermentation has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 14 herein.

In a preferred embodiment the ratio between glucoamylase and alpha-amylase present and/or added during saccharification and/or fermentation may preferably be in the range from 500:1 to 1:1, such as from 250:1 to 1:1, such as from 100:1 to 1:1, such as from 100:2 to 100:50, such as from 100:3 to 100:70.

Further Aspects of Processes of the Invention

Prior to liquefaction step a), processes of the invention, including processes of extracting/recovering oil and processes for producing fermentation products, may comprise the steps of:
i) reducing the particle size of the starch-containing material, preferably by dry milling;
ii) forming a slurry comprising the starch-containing material and water.

In an embodiment at least 50%, preferably at least 70%, more preferably at least 80%, especially at least 90% of the starch-containing material fit through a sieve with #6 screen.

In an embodiment the pH during liquefaction is between above 4.5-6.5, such as 4.5-5.0, such as around 4.8, or a pH between 5.0-6.2, such as 5.0-6.0, such as between 5.0-5.5, such as around 5.2, such as around 5.4, such as around 5.6, such as around 5.8.

In an embodiment the temperature during liquefaction is above the initial gelatinization temperature, preferably in the range from 70-100° C., such as between 75-95° C., such as between 75-90° C., preferably between 80-90° C., especially around 85° C.

In an embodiment a jet-cooking step is carried out before liquefaction in step a). In an embodiment the jet-cooking is carried out at a temperature between 110-145° C., preferably 120-140° C., such as 125-135° C., preferably around 130° C. for about 1-15 minutes, preferably for about 3-10 minutes, especially around about 5 minutes.

In a preferred embodiment saccharification and fermentation is carried out sequentially or simultaneously.

In an embodiment saccharification is carried out at a temperature from 20-75° C., preferably from 40-70° C., such as around 60° C., and at a pH between 4 and 5.

In an embodiment fermentation or simultaneous saccharification and fermentation (SSF) is carried out carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours.

In a preferred embodiment the fermentation product is recovered after fermentation, such as by distillation.

In an embodiment the fermentation product is an alcohol, preferably ethanol, especially fuel ethanol, potable ethanol and/or industrial ethanol.

In an embodiment the starch-containing starting material is whole grains. In an embodiment the starch-containing material is selected from the group of corn, wheat, barley, rye, milo, sago, cassava, manioc, tapioca, sorghum, rice, and potatoes.

In an embodiment the fermenting organism is yeast, preferably a strain of *Saccharomyces*, especially a strain of *Saccharomyces cerevisae*.

In an embodiment the temperature in step (a) is above the initial gelatinization temperature, such as at a temperature between 80-90° C., such as around 85° C.

In an embodiment a process of the invention further comprises a pre-saccharification step, before saccharification step b), carried out for 40-90 minutes at a temperature between 30-65° C. In an embodiment saccharification is carried out at a temperature from 20-75° C., preferably from 40-70° C., such as around 60° C., and at a pH between 4 and 5. In an embodiment fermentation step c) or simultaneous saccharification and fermentation (SSF) (i.e., steps b) and c)) are carried out carried out at a temperature from 25° C. to 40° C., such as from 28° C. to 35° C., such as from 30° C. to 34° C., preferably around about 32° C. In an embodiment the fermentation step c) or simultaneous saccharification and fermentation (SSF) (i.e., steps b) and c)) are ongoing for 6 to 120 hours, in particular 24 to 96 hours.

In an embodiment separation in step e) is carried out by centrifugation, preferably a decanter centrifuge, filtration, preferably using a filter press, a screw press, a plate-and-frame press, a gravity thickener or decker.

In an embodiment the fermentation product is recovered by distillation.

Examples of Specific Process Embodiments of the Invention

Producing Fermentation Products:

In one embodiment the invention relates to processes for producing ethanol from starch-containing material comprising the steps of:
a) liquefying the starch-containing material at a temperature above the initial gelatinization temperature using:
an alpha-amylase derived from *Bacillus stearothermophilus* having a double deletion of two amino acids in the region from position 179 to 182, more particularly a double deletion at positions I181+G182, R179+G180, G180+I181, R179+I181, or G180+G182, preferably I181+G182, and optional substitution N193F; further one of the following set of substitutions:

E129V+K177L+R179E;
V59A+Q89R+E129V+K177L+R179E+H208Y+K220P+
N224L+Q254S;
V59A+Q89R+E129V+K177L+R179E+Q254S+M284V;
E129V+K177L+R179E+K220P+N224L+S242Q+Q254S
(using SEQ ID NO: 5 herein for numbering), and wherein the alpha-amylase has at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 5;
a variant pullulanase, wherein the variants comprise the following combination of substitutions:
N222P+Q252A+Q256R+N368G+N393A+Q431E+
L432F+A492A,S+N610R+G624S+T631S+S632C+
N20G+Y28K+H80Y+Q187R+E310A+D311K+
Q387L+Q459G+D586S+E699R+S798R;
and further the variant comprises the following combinations of substitutions:
Q29G+P30*+V31*+N32*+D57N+D58P+A195G+N202K+
A345P+M402S+I460V+I514V+E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 78° C. relative to activity at 75° C.;
b) saccharifying using a glucoamylase enzyme;
c) fermenting using *Saccharomyces cerevisiae*.

In another embodiment the invention relates to processes for producing ethanol from starch-containing material comprising the steps of:
a) liquefying the starch-containing material at a temperature above the initial gelatinization temperature using:
an alpha-amylase derived from *Bacillus stearothermophilus* having a double deletion of two amino acids in the region from position 179 to 182, more particularly a double deletion at positions I181+G182, R179+G180, G180+I181, R179+I181, or G180+G182, preferably I181+G182, and optional substitution N193F; further one of the following set of substitutions:
E129V+K177L+R179E;
V59A+Q89R+E129V+K177L+R179E+H208Y+K220P+
N224L+Q254S;
V59A+Q89R+E129V+K177L+R179E+Q254S+M284V;
E129V+K177L+R179E+K220P+N224L+S242Q+Q254S
(using SEQ ID NO: 5 herein for numbering), and wherein the alpha-amylase has at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 5;
a variant pullulanase, wherein the variants comprise the following combination of substitutions:
N222P+Q252A+Q256R+N368G+N393A+Q431E+
L432F+A492A, S+N610R+G624S+T631S+S632C+
N20G+Y28K+H80Y+Q187R+E310A+D311K+
Q387L+Q459G+D586S+E699R+S798R;
and further the variant comprises the following combinations of substitutions:
Q29G+P30*+V31*+N32*+D57N+D58P+A195G+N197T+
A345P+M402S+F456W+I460V+I514V+E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 79° C. relative to activity at 75° C.;
b) saccharifying using a glucoamylase enzyme;
c) fermenting using *Saccharomyces cerevisiae*.

In another embodiment the invention relates to processes for producing ethanol from starch-containing material comprising the steps of:
a) liquefying the starch-containing material at a temperature above the initial gelatinization temperature using:
an alpha-amylase derived from *Bacillus stearothermophilus* having a double deletion of two amino acids in the region from position 179 to 182, more particularly a double deletion at positions I181+G182, R179+G180, G180+I181, R179+I181, or G180+G182, preferably I181+G182, and optional substitution N193F; further one of the following set of substitutions:
E129V+K177L+R179E;
V59A+Q89R+E129V+K177L+R179E+H208Y+K220P+
N224L+Q254S;

V59A+Q89R+E129V+K177L+R179E+Q254S+M284V;
E129V+K177L+R179E+K220P+N224L+S242Q+Q254S
(using SEQ ID NO: 5 herein for numbering), and wherein the alpha-amylase has at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 5;
a variant pullulanase, wherein the variants comprise the following combination of substitutions:
N222P+Q252A+Q256R+N368G+N393A+Q431E+ L432F+A492A,S+N610R+G624S+T631S+S632C+ N20G+Y28K+H80Y+Q187R+E310A+D311K+ Q387L+Q459G+D586S+E699R+S798R;
and further the variant comprises the following combinations of substitutions:
Q29G+P30*+V31*+N32*+D57N+D58P+A195G+N197T+ A345P+M402S+F456W+I460V+I514V+E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 79° C. relative to activity at 75° C.;
b) saccharifying using a glucoamylase enzyme;
c) fermenting using *Saccharomyces cerevisiae*.
In another embodiment the invention relates to processes for producing ethanol from starch-containing material comprising the steps of:
a) liquefying the starch-containing material at a temperature above the initial gelatinization temperature using:
an alpha-amylase derived from *Bacillus stearothermophilus* having a double deletion of two amino acids in the region from position 179 to 182, more particularly a double deletion at positions I181+G182, R179+G180, G180+ I181, R179+I181, or G180+G182, preferably I181+G182, and optional substitution N193F; further one of the following set of substitutions:
E129V+K177L+R179E;
V59A+Q89R+E129V+K177L+R179E+H208Y+K220P+ N224L+Q254S;
V59A+Q89R+E129V+K177L+R179E+Q254S+M284V;
E129V+K177L+R179E+K220P+N224L+S242Q+Q254S
(using SEQ ID NO: 5 herein for numbering), and wherein the alpha-amylase has at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 5;
a variant pullulanase, wherein the variants comprise the following combination of substitutions:
N222P+Q252A+Q256R+N368G+N393A+Q431E+ L432F+A492A,S+N610R+G624S+T631S+S632C+ N20G+Y28K+H80Y+Q187R+E310A+D311K+ Q387L+Q459G+D586S+E699R+S798R;
and further the variant comprises the following combinations of substitutions: Q29G+P30*+V31*+N32*+D57N+ D58P+A195G+A345P+M402S+F456W+I460V+N479H+ I514V+E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 79° C. relative to activity at 75° C.;
b) saccharifying using a glucoamylase enzyme;
c) fermenting using *Saccharomyces cerevisiae*.
In another embodiment the invention relates to processes for producing ethanol from starch-containing material comprising the steps of:
a) liquefying the starch-containing material at a temperature above the initial gelatinization temperature using:
an alpha-amylase derived from *Bacillus stearothermophilus* having a double deletion of two amino acids in the region from position 179 to 182, more particularly a double deletion at positions I181+G182, R179+G180, G180+ I181, R179+I181, or G180+G182, preferably I181+G182, and optional substitution N193F; further one of the following set of substitutions:
E129V+K177L+R179E;
V59A+Q89R+E129V+K177L+R179E+H208Y+K220P+ N224L+Q254S;
V59A+Q89R+E129V+K177L+R179E+Q254S+M284V;
E129V+K177L+R179E+K220P+N224L+S242Q+Q254S
(using SEQ ID NO: 5 herein for numbering), and wherein the alpha-amylase has at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 5;
a variant pullulanase, wherein the variants comprise the following combination of substitutions:
N222P+Q252A+Q256R+N368G+N393A+Q431E+ L432F+A492A,S+N610R+G624S+T631S+S632C+ N20G+Y28K+H80Y+Q187R+E310A+D311K+ Q387L+Q459G+D586S+E699R+S798R;
and further the variant comprises the following combinations of substitutions:
Q29G+P30*+V31*+N32*+D57N+D58P+A195G+N197T+ N202K+A345P+M402S+F456W+I460V+I514V+ E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 79° C. relative to activity at 75° C.;
b) saccharifying using a glucoamylase enzyme;
c) fermenting using *Saccharomyces cerevisiae*.
In another embodiment the invention relates to processes for producing ethanol from starch-containing material comprising the steps of:
a) liquefying the starch-containing material at a temperature above the initial gelatinization temperature using:
an alpha-amylase derived from *Bacillus stearothermophilus* having a double deletion of two amino acids in the region from position 179 to 182, more particularly a double deletion at positions I181+G182, R179+G180, G180+ I181, R179+I181, or G180+G182, preferably I181+G182, and optional substitution N193F; further one of the following set of substitutions:
E129V+K177L+R179E;
V59A+Q89R+E129V+K177L+R179E+H208Y+K220P+ N224L+Q254S;
V59A+Q89R+E129V+K177L+R179E+Q254S+M284V;
E129V+K177L+R179E+K220P+N224L+S242Q+Q254S
(using SEQ ID NO: 5 herein for numbering), and wherein the alpha-amylase has at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 5;
a variant pullulanase, wherein the variants comprise the following combination of substitutions:
N222P+Q252A+Q256R+N368G+N393A+Q431E+ L432F+A492A,S+N610R+G624S+T631S+S632C+ N20G+Y28K+H80Y+Q187R+E310A+D311K+ Q387L+Q459G+D586S+E699R+S798R;
and further the variant comprises the following combinations of substitutions:
Q29G+P30*+V31*+N32*+D57N+D58P+A195G+N202K+ A345P+M402S+F456W+I460V+N479H+I514V+ E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 79° C. relative to activity at 75° C.;
b) saccharifying using a glucoamylase enzyme;
c) fermenting using *Saccharomyces cerevisiae*.

In another embodiment the invention relates to processes for producing ethanol from starch-containing material comprising the steps of:
a) liquefying the starch-containing material at a temperature above the initial gelatinization temperature using:
an alpha-amylase derived from *Bacillus stearothermophilus* having a double deletion of two amino acids in the region from position 179 to 182, more particularly a double deletion at positions I181+G182, R179+G180, G180+ I181, R179+I181, or G180+G182, preferably I181+G182, and optional substitution N193F; further one of the following set of substitutions:
E129V+K177L+R179E;
V59A+Q89R+E129V+K177L+R179E+H208Y+K220P+ N224L+Q254S;
V59A+Q89R+E129V+K177L+R179E+Q254S+M284V;
E129V+K177L+R179E+K220P+N224L+S242Q+Q254S (using SEQ ID NO: 5 herein for numbering), and wherein the alpha-amylase has at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 5;
a variant pullulanase, wherein the variants comprise the following combination of substitutions: N222P+Q252A+ Q256R+N368G+N393A+Q431E+L432F+A492A,S+ N610R+G624S+T631S+S632C+N20G+Y28K+H80Y+ Q187R+E310A+D311K+Q387L+Q459G+D586S+ E699R+S798R;
and further the variant comprises the following combinations of substitutions:
Q29G+P30*+V31*+N32*+D57N+D58P+A195G+N197T+ N202K+A345P+M402S+F456W+I460V+N479H+ I514V+E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 79° C. relative to activity at 75° C.;
b) saccharifying using a glucoamylase enzyme;
c) fermenting using *Saccharomyces cerevisiae*.

In a preferred embodiment saccharification in step b) is performed using a glucoamylase and an alpha-amylase selected as a *Rhizomucor pusillus* alpha-amylase with an *Aspergillus niger* glucoamylase linker and starch-binding domain (SBD), preferably disclosed as SEQ ID NO: 14 herein, preferably having one or more of the following substitutions: G128D, D143N, preferably G128D+D143N (using SEQ ID NO: 14 for numbering);
c) fermenting using a fermenting organism.

Fermentation Medium

The environment in which fermentation is carried out is often referred to as the "fermentation media" or "fermentation medium". The fermentation medium includes the fermentation substrate, that is, the carbohydrate source that is metabolized by the fermenting organism. According to the invention the fermentation medium may comprise nutrients and growth stimulator(s) for the fermenting organism(s). Nutrient and growth stimulators are widely used in the art of fermentation and include nitrogen sources, such as ammonia; urea, vitamins and minerals, or combinations thereof.

Fermenting Organisms

The term "fermenting organism" refers to any organism, including bacterial and fungal organisms, especially yeast, suitable for use in a fermentation process and capable of producing the desired fermentation product. Especially suitable fermenting organisms are able to ferment, i.e., convert, sugars, such as glucose or maltose, directly or indirectly into the desired fermentation product, such as ethanol. Examples of fermenting organisms include fungal organisms, such as yeast. Preferred yeast includes strains of *Saccharomyces* spp., in particular, *Saccharomyces cerevisiae*.

Suitable concentrations of the viable fermenting organism during fermentation, such as SSF, are well known in the art or can easily be determined by the skilled person in the art. In one embodiment the fermenting organism, such as ethanol fermenting yeast, (e.g., *Saccharomyces cerevisiae*) is added to the fermentation medium so that the viable fermenting organism, such as yeast, count per mL of fermentation medium is in the range from $10^5$ to $10^{12}$, preferably from $10^7$ to $10^{10}$, especially about $5 \times 10^7$. Examples of commercially available yeast includes, e.g., RED START™ and ETHANOL RED™ yeast (available from Fermentis/ Lesaffre, USA), FALI (available from Fleischmann's Yeast, USA), SUPERSTART and THERMOSACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

Starch-Containing Materials

Any suitable starch-containing material may be used according to the present invention. The starting material is generally selected based on the desired fermentation product. Examples of starch-containing materials, suitable for use in a process of the invention, include whole grains, corn, wheat, barley, rye, milo, sago, cassava, tapioca, sorghum, rice, peas, beans, or sweet potatoes, or mixtures thereof or starches derived therefrom, or cereals. Contemplated are also waxy and non-waxy types of corn and barley. In a preferred embodiment the starch-containing material, used for ethanol production according to the invention, is corn or wheat.

Fermentation Products

The term "fermentation product" means a product produced by a process including a fermentation step using a fermenting organism. Fermentation products contemplated according to the invention include alcohols (e.g., ethanol, methanol, butanol; polyols such as glycerol, sorbitol and inositol); organic acids (e.g., citric acid, acetic acid, itaconic acid, lactic acid, succinic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferably processes of the invention are used for producing an alcohol, such as ethanol. The fermentation product, such as ethanol, obtained according to the invention, may be used as fuel, which is typically blended with gasoline. However, in the case of ethanol it may also be used as potable ethanol.

Recovery of Fermentation Products

Subsequent to fermentation, or SSF, the fermentation product may be separated from the fermentation medium. The slurry may be distilled to extract the desired fermentation product (e.g., ethanol). Alternatively the desired fermentation product may be extracted from the fermentation medium by micro or membrane filtration techniques. The fermentation product may also be recovered by stripping or other method well known in the art.

The invention is further defined in the following numbered embodiments:

Embodiment 1. A variant pullulanase, wherein the pullulanase comprises at least the following combination of substitutions:
N368G+N393A+Q431E+L432F+A492A,S+N610R+G624S+T631S+S632C, and optionally further comprises N222P+Q252A+Q256R; wherein the variant has pullulanase activity, and wherein the variants have at least 85%, at least 90%, at least 95%, at least 96%, at least 97%, at least 98%, or at least 99%, but less than 100% sequence identity to the polypeptide of SEQ ID NO: 3.

Embodiment 2. The variant according to embodiment 1, wherein said variants have at least 30% relative activity when measured at 76° C. relative to activity at 65° C.

Embodiment 3. The variant according to embodiment 1, wherein the variant pullulanase further comprises N20G+Y28K+H80Y+Q187R+E310A+D311K+Q387L+Q459G+D586S+E699R+S798R;

Embodiment 4. The variant according to embodiments 1 and 3, wherein said variants have at least 50% relative activity when measured at 78° C. relative to activity at 65° C.

Embodiment 5. The variant according to embodiment 3, wherein the variant comprises the following combination of substitutions:
N222P+Q252A+Q256R+N368G+N393A+Q431E+L432F+A492A+N610R+G624S+T631S+S632C+N20G+Y28K+H80Y+Q187R+E310A+D311K+Q387L+Q459G+D586S+E699R+S798R;
and further the variant comprises one of the following combinations of deletions and substitutions:
P30*+V31*+N32*;
P30*+V31*+N32*+D57N+D58P;
Q29G+P30*+V31*+N32*+D57N+D58P;
P30*+V31*+N32*+D57N+D58P+A195G;
P30*+V31*+N32*+D57N+D58P+N197T;
P30*+V31*+N32*+D57N+D58P+N202K;
P30*+V31*+N32*+D57N+D58P+A345P;
P30*+V31*+N32*+D57N+D58P+M402S;
P30*+V31*+N32*+D57N+D58P+F456W;
P30*+V31*+N32*+D57N+D58P+I460V;
P30*+V31*+N32*+D57N+D58P+N479H;
P30*+V31*+N32*+D57N+D58P+I514V;
P30*+V31*+N32*+D57N+D58P+E560R;
P30*+V31*+N32*+D57N+D58P+D615E;
P30*+V31*+N32*+D57N+D58P+A345P+E560R;
P30*+V31*+N32*+D57N+D58P+A345P+I514V;
P30*+V31*+N32*+D57N+D58P+A345P+I460V+I514V;
P30*+V31*+N32*+D57N+D58P+A195G+A345P+I460V+I514V;
P30*+V31*+N32*+D57N+D58P+N202K+A345P+E560R;
P30*+V31*+N32*+D57N+D58P+A345P+M402S+E560R;
P30*+V31*+N32*+D57N+D58P+N202K+A345P+M402S+E560R;
P30*+V31*+N32*+D57N+D58P+A195G+N202K+A345P+M402S+I460V+I514V;
P30*+V31*+N32*+D57N+D58P+F456W;
Q29G+P30*+V31*+N32*+D57N+D58P+A195G+A345P+I460V+I514V;
Q29G+P30*+V31*+N32*+D57N+D58P+A195G+N202K+A345P+M402S+I460V+I514V;
Q29G+P30*+V31*+N32*+D57N+D58P+A195G+N202K+A345P+M402S+I460V+I514V+E560R;
Q29G+P30*+V31*+N32*+D57N+D58P+A195G+N202K+A345P+M402S+I460V+I514V+E560R+D615E;
P30*+V31*+N32*+D57N+D58P+A195G+A345P+M402S+I460V+I514V+E560R;
P30*+V31*+N32*+D57N+D58P+A195G+A345P+M402S+I514V;
P30*+V31*+N32*+D57N+D58P+A195G+A345P;
P30*+V31*+N32*+D57N+D58P+A195G+A345P+F456W;
Q29G+P30*+V31*+N32*+D57N+D58P+A195G+A345P+M402S+F456W+I460V+I514V;
P30*+V31*+N32*+D57N+D58P+N479H;
P30*+V31*+N32*+D57N+D58P+A195G+A345P+M402S+F456W+I460V+I514V+E560R;
P30*+V31*+N32*+D57N+D58P+A195G+A345P+M402S+I460V+N479H+I514V+E560R;
P30*+V31*+N32*+D57N+D58P+N197T+A345P+M402S+I460V+I514V+E560R;
Q29G+P30*+V31*+N32*+D57N+D58P+A195G+A252I+N202K+A345P+M402S+I460V+I514V+E560R;
Q29G+P30*+V31*+N32*+D57N+D58P+A195G+N197T+N202K+A345P+M402S+I460V+I514V+E560R;
Q29G+P30*+V31*+N32*+D57N+D58P+A195G+N202K+A345P+M402S+F456W+I460V+I514V+E560R;
Q29G+P30*+V31*+N32*+D57N+D58P+A195G+N197T+A345P+M402S+F456W+I460V+I514V+E560R;
Q29G+P30*+V31*+N32*+D57N+D58P+A195G+A345P+M402S+F456W+I460V+N479H+I514V+E560R;
Q29G+P30*+V31*+N32*+D57N+D58P+A195G+N197T+N202K+A345P+M402S+F456W+I460V+I514V+E560R;
Q29G+P30*+V31*+N32*+D57N+D58P+A195G+N202K+A345P+M402S+F456W+I460V+N479H+I514V+E560R;

Q29G+P30*+V31*+N32*+D57N+D58P+A195G+N197T+ N202K+A345P+M402S+F456W+I460V+N479H+ I514V+E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 50%, particularly at least 60%, more particularly at least 70%, even more particularly at least 80% relative activity when measured at 78° C. relative to activity at 65° C.

Embodiment 6. The variants according to embodiment 5, wherein the variant pullulanase is selected from pullulanase variants, wherein the variants comprise the following combination of substitutions:

N222P+Q252A+Q256R+N368G+N393A+Q431E+ L432F+A492A, S+N610R+G624S+T631S+S632C+ N20G+Y28K+H80Y+Q187R+E310A+D311K+ Q387L+Q459G+D586S+E699R+S798R;

and further the variant comprises the following combinations of substitutions:

Q29G+P30*+V31*+N32*+D57N+D58P+A195G+N202K+ A345P+M402S+I460V+I514V+E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 78° C. relative to activity at 75° C.

Embodiment 7. The variants according to embodiment 5, wherein the variant pullulanase is selected from pullulanase variants, wherein the variants comprise the following combination of substitutions:

N222P+Q252A+Q256R+N368G+N393A+Q431E+ L432F+A492A, S+N610R+G624S+T631S+S632C+ N20G+Y28K+H80Y+Q187R+E310A+D311K+ Q387L+Q459G+D586S+E699R+S798R;

and further the variant comprises the following combinations of substitutions:

Q29G+P30*+V31*+N32*+D57N+D58P+A195G+N202K+ A345P+M402S+F456W+I460V+I514V+E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 78° C. relative to activity at 75° C.

Embodiment 8. The variants according to embodiment 5, wherein the variant pullulanase is selected from pullulanase variants, wherein the variants comprise the following combination of substitutions:

N222P+Q252A+Q256R+N368G+N393A+Q431E+ L432F+A492A,S+N610R+G624S+T631S+S632O+ N20G+Y28K+H80Y+Q187R+E310A+D311K+ Q387L+Q459G+D586S+E699R+S798R;

and further the variant comprises the following combinations of substitutions:

Q29G+P30*+V31*+N32*+D57N+D58P+A195G+N197T+ A345P+M402S+F456W+I460V+I514V+E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 79° C. relative to activity at 75° C.

Embodiment 9. The variants according to embodiment 5, wherein the variant pullulanase is selected from pullulanase variants, wherein the variants comprise the following combination of substitutions:

N222P+Q252A+Q256R+N368G+N393A+Q431E+ L432F+A492A,S+N610R+G624S+T631S+S632C+ N20G+Y28K+H80Y+Q187R+E310A+D311K+ Q387L+Q459G+D586S+E699R+S798R;

and further the variant comprises the following combinations of substitutions:

Q29G+P30*+V31*+N32*+D57N+D58P+A195G+A345P+ M402S+F456W+I460V+N479H+I514V+E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 79° C. relative to activity at 75° C.

Embodiment 10. The variants according to embodiment 5, wherein the variant pullulanase is selected from pullulanase variants, wherein the variants comprise the following combination of substitutions:

N222P+Q252A+Q256R+N368G+N393A+Q431E+ L432F+A492A,S+N610R+G624S+T631S+S632C+ N20G+Y28K+H80Y+Q187R+E310A+D311K+ Q387L+Q459G+D586S+E699R+S798R;

and further the variant comprises the following combinations of substitutions:

Q29G+P30*+V31*+N32*+D57N+D58P+A195G+N197T+ N202K+A345P+M402S+F456W+I460V+I514V+ E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 79° C. relative to activity at 75° C.

Embodiment 11. The variants according to embodiment 5, wherein the variant pullulanase is selected from pullulanase variants, wherein the variants comprise the following combination of substitutions:

N222P+Q252A+Q256R+N368G+N393A+Q431E+ L432F+A492A,S+N610R+G624S+T631S+S632C+ N20G+Y28K+H80Y+Q187R+E310A+D311K+ Q387L+Q459G+D586S+E699R+S798R;

and further the variant comprises the following combinations of substitutions:

Q29G+P30*+V31*+N32*+D57N+D58P+A195G+N202K+ A345P+M402S+F456W+I460V+N479H+I514V+ E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 79° C. relative to activity at 75° C.

Embodiment 12. The variants according to embodiment 5, wherein the variant pullulanase is selected from pullulanase variants, wherein the variants comprise the following combination of substitutions:

N222P+Q252A+Q256R+N368G+N393A+Q431E+ L432F+A492A,S+N610R+G624S+T631S+S632C+

N20G+Y28K+H80Y+Q187R+E310A+D311K+ Q387L+Q459G+D586S+E699R+S798R;

and further the variant comprises the following combinations of substitutions:

Q29G+P30*+V31*+N32*+D57N+D58P+A195G+N197T+ N202K+A345P+M402S+F456W+I460V+N479H+ I514V+E560R; and wherein the variant has pullulanase activity, and the variants have at least 85%, at least 90%, at least 95%, at least 96%, at least 97%, at least 98%, or at least 99%, but less than 100% sequence identity to the polypeptide of SEQ ID NO: 3, and wherein said variants have at least 70% relative activity when measured at 79° C. relative to activity at 75° C.

Embodiment 13. A polynucleotide encoding the pullulanase of any of the embodiments 1-12.

Embodiment 14. A nucleic acid construct or expression vector comprising the polynucleotide of embodiment 13 operably linked to one or more control sequences that direct the production of the polypeptide in an expression host.

Embodiment 15. A recombinant host cell comprising the polynucleotide of embodiment 13 operably linked to one or more control sequences that direct the production of the polypeptide.

Embodiment 16. A whole broth formulation or cell culture composition comprising the polypeptide of any of embodiments 1-12.

Embodiment 17. A composition comprising the variant pullulanase of any of embodiments 1-12 and a stabilizer.

Embodiment 18. The composition according to embodiment 17, further comprising an alpha-amylase.

Embodiment 19. The composition according to embodiment 18, wherein the alpha-amylase is from the genus *Exiguobacterium* or Bacillus, such as a strain of *Bacillus stearothermophilus*, in particular a variant of a *Bacillus stearothermophilus* alpha-amylase, such as the one shown in SEQ ID NO: 5.

Embodiment 20. The composition of embodiment 16, wherein the *Bacillus stearothermophilus* alpha-amylase or variant thereof is truncated, preferably after position 484 of SEQ ID NO: 5, particularly after position 485, particularly after position 486, particularly after position 487, particularly after position 488, particularly after position 489, particularly after position 490, particularly after position 491, particularly after position 492, more particularly after position 493.

Embodiment 21. The composition of any of embodiments 19 or 1207, wherein the *Bacillus stearothermophilus* alpha-amylase has a double deletion at positions I181+G182, R179+G180, G180I+181, R179I+181, or G180+G182, preferably I181+G182, and optionally a N193F substitution, (using SEQ ID NO: 5 for numbering).

Embodiment 22. The composition of any of embodiments 19-21, wherein the *Bacillus stearothermophilus* alpha-amylase has a substitution at position S242, preferably S242Q substitution.

Embodiment 23. The composition of any of embodiments 19-22, wherein the *Bacillus stearothermophilus* alpha-amylase has a substitution at position E188, preferably E188P substitution.

Embodiment 24. The composition of any of embodiments 19-23, wherein the alpha-amylase is selected from the group of *Bacillus stearothermophilus* alpha-amylase variants:

I181*+G182*+N193F+E129V+K177L+R179E;
I181*+G182*+N193F+V59A+Q89R+E129V+K177L+ R179E+H208Y+K220P+N224L+Q254S;
I181*+G182*+N193F+V59A Q89R+E129V+K177L+ R179E+Q254S+M284V; and
I181*+G182*+N193F+E129V+K177L+R179E+K220P+ N224L+S242Q+Q254S (using SEQ ID NO: 5 for numbering), and wherein the alpha-amylase variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 5.

Embodiment 25. The composition according to any of embodiments 17-24, further comprising a protease, preferably a protease selected from a *Pyrococcus* sp protease, e.g. a *Pyrococcus furiosus* protease shown as SEQ ID NO: 7, a *Thermococcus* sp. 58A protease shown as SEQ ID NO: 8, e.g. a *Thermococcus litoralis* S8A protease, or a *Thermoascus* sp protease, e.g., a *Thermoascus aurantiacus* protease, particularly a variant of a *Thermoascus aurantiacus* protease, SEQ ID NO: 6, comprising one of the specific combinations of substitutions in the D79L+ S87P+A112P+D142L;
D79L+S87P+D142L; or
A27K+D79L+Y82F+S87G+D104P+A112P+A126V+ D142L.

Embodiment 26. A method of producing a polypeptide according to any of the embodiments 1-12, comprising cultivating the host cell of embodiment 15 under conditions conducive for production of the polypeptide.

Embodiment 27. A process for producing a syrup from starch-containing material comprising the steps of:
a) liquefying the starch-containing material at a temperature above the initial gelatinization temperature using an alpha-amylase and a variant pullulanase of any of the embodiments 1-12;
b) saccharifying using a glucoamylase.

Embodiment 28. A process for producing fermentation products from starch-containing material comprising the steps of:
a) liquefying the starch-containing material at a temperature above the initial gelatinization temperature using an alpha-amylase and a variant pullulanase of any of the embodiments 1-12;
b) saccharifying using a glucoamylase;
c) fermenting using a fermenting organism.

Embodiment 29. The process according to any of embodiments 27-28, wherein the alpha-amylase is from the genus *Exiguobacterium* or *Bacillus*, such as a strain of *Bacillus stearothermophilus*, in particular a variant of a *Bacillus stearothermophilus* alpha-amylase, such as the one shown in SEQ ID NO: 5.

Embodiment 30. The process of embodiment 29, wherein the *Bacillus stearothermophilus* alpha-amylase or variant thereof is truncated, preferably after position 484 of SEQ ID NO: 5, particularly after position 485, particularly after position 486, particularly after position 487, particularly after position 488, particularly after position 489, particularly after position 490, particularly after position 491, particularly after position 492, more particularly after position 493.

Embodiment 31. The process of any of embodiments 29-30, wherein the *Bacillus stearothermophilus* alpha-amylase has a double deletion at positions I181+G182, R179+ G180, G180+I181, R179+I181, or G180+G182, preferably I181+G182, and optionally a N193F substitution, (using SEQ ID NO: 5 for numbering).

Embodiment 32. The process of any of embodiments 29-31, wherein the *Bacillus stearothermophilus* alpha-amylase has a substitution at position S242, preferably S242Q substitution.

Embodiment 33. The process of any of embodiments 29-32, wherein the *Bacillus stearothermophilus* alpha-amylase has a substitution at position E188, preferably E188P substitution.

Embodiment 34. The process of any of embodiments 29-33, wherein the alpha-amylase is selected from the group of *Bacillus stearothermophilus* alpha-amylase variants:
I181*+G182*+N193F+E129V+K177L+R179E;
I181*+G182*+N193F+V59A+Q89R+E129V+K177L+R179E+H208Y+K220P+N224L+Q254S;
I181*+G182*+N193F+V59A  Q89R+E129V+K177L+R179E+Q254S+M284V; and
I181*+G182*+N193F+E129V+K177L+R179E+K220P+N224L+S242Q+Q254S (using SEQ ID NO: 5 for numbering), and wherein the alpha-amylase variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 5.

Embodiment 35. The process of any of embodiments 27-34, further comprising that a protease is present in step a), preferably a protease selected from a *Pyrococcus* sp protease, e.g. a *Pyrococcus furiosus* protease shown as SEQ ID NO: 7, a *Thermococcus* sp. 58A protease, shown as SEQ ID NO: 8, e.g. a *Thermococcus litoralis* 58A protease, or a *Thermoascus* sp protease, e.g., a *Thermoascus aurantiacus* protease, particularly a variant of a *Thermoascus aurantiacus* protease, SEQ ID NO: 6, comprising one of the specific combinations of substitutions in the D79L+S87P+A112P+D142L;
D79L+S87P+D142L; or
A27K+D79L+Y82F+S87G+D104P+A112P+A126V+D142L.

Embodiment 36. The process of any of embodiments 27-35, wherein the glucoamylase present and/or added in saccharification step b) and/or fermentation step c) is of fungal origin, preferably from a stain of *Aspergillus*, preferably *A. niger, A. awamori*, or *A. oryzae*; or a strain of *Trichoderma*, preferably *T. reesei*; or a strain of *Talaromyces*, preferably *T. emersonii*, or a strain of *Trametes*, preferably *T. cingulata*, or a strain of *Pycnoporus*, or a strain of *Gloeophyllum*, such as *G. sepiarium* or *G. trabeum*, or a strain of *Nigrofomes*.

Embodiment 37. The process of embodiment 36, wherein the glucoamylase is derived from *Talaromyces emersonii*, such as the one shown in SEQ ID NO: 9 herein.

Embodiment 38. The process of embodiment 37, wherein the glucoamylase is selected from the group consisting of:
(i) a glucoamylase comprising the polypeptide of SEQ ID NO: 9 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 9.

Embodiment 39. The process of embodiments 36, wherein the glucoamylase is derived from *Gloeophyllum sepiarium*, such as the one shown in SEQ ID NO: 11.

Embodiment 40. The process of embodiments 39, wherein the glucoamylase is selected from the group consisting of:
(i) a glucoamylase comprising the polypeptide of SEQ ID NO: 11;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 11.

Embodiment 41. The process of embodiments 36, wherein the glucoamylase is derived from *Gloeophyllum trabeum* such as the one shown in SEQ ID NO: 12.

Embodiment 42. The process of embodiment 41, wherein the glucoamylase is selected from the group consisting of:
(i) a glucoamylase comprising the polypeptide of SEQ ID NO: 12;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 12.

Embodiment 43. The process of any of embodiments 27-42, wherein a glucoamylase in combination with an alpha-amylase is present in saccharification and/or fermentation.

Embodiment 44. The process of embodiment 43, wherein the alpha-amylase present in saccharification and/or fermentation is of fungal or bacterial origin.

Embodiment 45. The process of embodiment 43 or 44, wherein the alpha-amylase present and/or added in saccharification and/or fermentation is derived from a strain of the genus *Rhizomucor*, preferably a strain the *Rhizomucor pusillus*, such as a *Rhizomucor pusillus* alpha-amylase hybrid having an *Aspergillus niger* linker and starch-bonding domain, such as the one shown in SEQ ID NO: 14.

Embodiment 46. The process of any of embodiments 43-45, wherein the alpha-amylase present in saccharification and/or fermentation is selected from the group consisting of:
(i) an alpha-amylase comprising the polypeptide of SEQ ID NO: 14;
(ii) an alpha-amylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 14.

Embodiment 47. The process of embodiment 46, wherein the alpha-amylase comprises one or more of the following substitutions: G128D, D143N, preferably G128D+D143N.

Embodiment 48. The process of any of embodiments 27-47, further comprising, prior to the liquefaction step a), the steps of:
i) reducing the particle size of the starch-containing material, preferably by dry milling;
ii) forming a slurry comprising the starch-containing material and water.

Embodiment 49. The process of any of embodiments 27-48, wherein at least 50%, preferably at least 70%, more preferably at least 80%, especially at least 90% of the starch-containing material fit through a sieve with #6 screen.

Embodiment 50. The process of any of embodiments 27-49, wherein the pH in liquefaction is between above 4.5-6.5, such as around 4.8, or a pH between 5.0-6.2, such as 5.0-6.0, such as between 5.0-5.5, such as around 5.2, such as around 5.4, such as around 5.6, such as around 5.8.

Embodiment 51. The process of any of embodiments 27-50, wherein the temperature in liquefaction is above the initial gelatinization temperature, such as in the range from 70-100° C., such as between 75-95° C., such as between 75-90° C., preferably between 80-90° C., especially around 85° C.

Embodiment 52. The process of any of embodiments 27-51, wherein a jet-cooking step is carried out before liquefaction in step a).

Embodiment 53. The process of embodiment 52, wherein the jet-cooking is carried out at a temperature between 110-145° C., preferably 120-140° C., such as 125-135° C., preferably around 130° C. for about 1-15 minutes, preferably for about 3-10 minutes, especially around about 5 minutes.

Embodiment 54. The process of any of embodiments 27-53, wherein saccharification is carried out at a temperature from 20-75° C., preferably from 40-70° C., such as around 60° C., and at a pH between 4 and 5.

Embodiment 55. The process of any of embodiments 28-54, wherein fermentation or simultaneous saccharification and fermentation (SSF) is carried out carried out at a temperature from 25° C. to 40° C., such as from 28° C. to 35° C., such as from 30° C. to 34° C., preferably around about 32° C.

Embodiment 56. The process of any of embodiments 28-55, wherein the fermentation product is recovered after fermentation, such as by distillation.

Embodiment 57. The process of any of embodiments 28-56, wherein the fermentation product is an alcohol, preferably ethanol, especially fuel ethanol, potable ethanol and/or industrial ethanol.

Embodiment 58. The process of any of embodiments 27-57, wherein the starch-containing starting material is whole grains.

Embodiment 59. The process of any of embodiments 27-58, wherein the starch-containing material is derived from corn, wheat, barley, rye, milo, sago, cassava, manioc, tapioca, sorghum, rice or potatoes.

Embodiment 60. The process of any of embodiments 28-59, wherein the fermenting organism is yeast, preferably a strain of *Saccharomyces*, especially a strain of *Saccharomyces cerevisiae*.

Embodiment 61. The recombinant host cell according to embodiment 15, wherein the host cell is a yeast host cell, particularly a strain of *Saccharomyces*, more particularly *Saccharomyces cerevisiae*.

Embodiment 62. A use of the host cell according to embodiment 61, in saccharification of starch.

Embodiment 63. A use of the variant pullulanase of any of the embodiments 1-12 in a brewing process.

Embodiment 64. A method of producing a brewer's wort comprising adding to a mash, a pullulanase of any of embodiments 1-12.

The present invention is further described by the following examples that should not be construed as limiting the scope of the invention.

EXAMPLES

Enzymes

Protease PfuS: Protease derived from *Pyrococcus furiosus* shown in SEQ ID NO: 7.

Alpha-Amylase BE369 (AA369): *Bacillus stearothermophilus* alpha-amylase disclosed herein as SEQ ID NO: 5, and further having the mutations: I181*+G182*+N193F+V59A+Q89R+E129V+K177L+R179E+Q254S+M284V truncated to 491 amino acids (using SEQ ID NO: 5 for numbering).

Alpha-amylase blend AA: Blend comprising Alpha-amylase AA369, and protease PfuS (dosing: 2.1 µg EP /g DS AA369, 3.0 µg EP/g DS PfuS, where EP is enzyme protein and DS is total dry solids).

Glucoamylase A: Blend comprising *Talaromyces emersonii* glucoamylase (Te AMG) disclosed as SEQ ID NO: 34 in WO99/28448, *Trametes cingulata* glucoamylase (Tc AMG) disclosed as SEQ ID NO: 2 in WO 06/69289, and *Rhizomucor pusillus* alpha-amylase with *Aspergillus niger* glucoamylase linker and starch binding domain (SBD) (Rp AA) disclosed in SEQ ID NO: 14 herein having the following substitutions G128D+D143N using SEQ ID NO: 14 for numbering (activity ratio in AGU:AGU:FAU-F is about 29:8:1).

Glucoamylase B: Same as glucoamylase blend A further having a cellulase composition containing a *Trichoderma reesei* cellulase preparation containing *Aspergillus fumigatus* cellobiohydrolase I (WO 2011/057140), *Aspergillus fumigatus* cellobiohydrolase II (WO 2011/057140), *Aspergillus fumigatus* beta-glucosidase variant (WO 2012/044915), and *Penicillium* sp. (emersonii) GH61 polypeptide (WO 2011/041397) (dosing: Te AMG 60 µg EP/gDS; Tc AMG 20 µg EP/gDS; Rp AA 11 µg EP/gDS; Cellulase composition 30 µg EP/gDS).

Yeast: ETHANOL RED™ from Fermentis, USA

Assays

Protease assays

1) Kinetic Suc-AAPF-pNA Assay:

pNA substrate: Suc-AAPF-pNA (Bachem L-1400).
Temperature: Room temperature (25° C.)
Assay buffers: 100 mM succinic acid, 100 mM HEPES, 100 mM CHES, 100 mM CABS, 1 mM $CaCl_2$, 150 mM KCl, 0.01% Triton X-100 adjusted to pH-values 2.0, 3.0, 4.0, 5.0, 6.0, 7.0, 8.0, 9.0, 10.0, and 11.0 with HCl or NaOH.

20 µl protease (diluted in 0.01% Triton X-100) was mixed with 100 µl assay buffer. The assay was started by adding 100 µl pNA substrate (50 mg dissolved in 1.0 ml DMSO and further diluted 45× with 0.01% Triton X-100). The increase in $OD_{405}$ was monitored as a measure of the protease activity.

2) Endpoint Suc-AAPF-pNA AK Assay:

pNA substrate: Suc-AAPF-pNA (Bachem L-1400).
Temperature: controlled (assay temperature).
Assay buffer: 100 mM succinic acid, 100 mM HEPES, 100 mM CHES, 100 mM CABS, 1 mM $CaCl_2$, 150 mM KCl, 0.01% Triton X-100, pH 7.0.

200 µl pNA substrate (50 mg dissolved in 1.0 ml DMSO and further diluted 45× with the Assay buffer) were pipetted in an Eppendorf tube and placed on ice. 20 µl protease sample (diluted in 0.01% Triton X-100) was added. The assay was initiated by transferring the Eppendorf tube to an Eppendorf thermomixer, which was set to the assay temperature. The tube was incubated for 15 minutes on the Eppendorf thermomixer at its highest shaking rate (1400 rpm.). The incubation was stopped by transferring the tube back to the ice bath and adding 600 µl 500 mM Succinic acid/NaOH, pH 3.5. After mixing the Eppendorf tube by vortexing 200 µl mixture was transferred to a microtiter plate. $OD_{405}$ was read as a measure of protease activity. A buffer blind was included in the assay (instead of enzyme).

Glucoamylase Activity (AGU)

Glucoamylase activity may be measured in Glucoamylase Units (AGU).

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
|---|---|
| Substrate: | maltose 23.2 mM |
| Buffer: | acetate 0.1M |
| pH: | 4.30 ± 0.05 |
| Incubation temperature: | 37° C. ± 1 |
| Reaction time: | 5 minutes |
| Enzyme working range: | 0.5-4.0 AGU/mL |

| Color reaction: | |
|---|---|
| GlucDH: | 430 U/L |
| Mutarotase: | 9 U/L |
| NAD: | 0.21 mM |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes A/S, Denmark, which folder is hereby included by reference.

Alpha-Amylase Activity

Acid Alpha-Amylase Activity (AFAU)

Acid alpha-amylase activity may be measured in AFAU (Acid Fungal Alpha-amylase Units), which are determined relative to an enzyme standard. 1 AFAU is defined as the amount of enzyme which degrades 5.260 mg starch dry matter per hour under the below mentioned standard conditions.

Acid alpha-amylase, an endo-alpha-amylase (1,4-alpha-D-glucan-glucanohydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

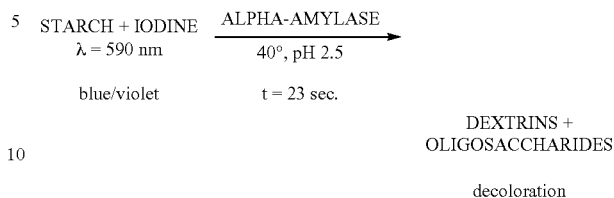

Standard conditions/reaction conditions:
Substrate: Soluble starch, approx. 0.17 g/L
Buffer: Citrate, approx. 0.03 M
Iodine (12): 0.03 g/L
$CaCl_2$: 1.85 mM
pH: 2.50±0.05
Incubation 40° C. temperature:
Reaction time: 23 seconds
Wavelength: 590 nm
Enzyme 0.025 AFAU/mL concentration:
Enzyme working 0.01-0.04 AFAU/mL range:

A folder EB-SM-0259.02/01 describing this analytical method in more detail is available upon request to Novozymes A/S, Denmark, which folder is hereby included by reference.

Determination of FAU-F

FAU-F Fungal Alpha-Amylase Units (Fungamyl) is measured relative to an enzyme standard of a declared strength.

| Reaction conditions | |
|---|---|
| Temperature | 37° C. |
| pH | 7.15 |
| Wavelength | 405 nm |
| Reaction time | 5 min |
| Measuring time | 2 min |

A folder (EB-SM-0216.02) describing this standard method in more detail is available on request from Novozymes A/S, Denmark, which folder is hereby included by reference.

Alpha-Amylase Activity (KNU)

The alpha-amylase activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C.+/−0.05; 0.0003 M $Ca^{2+}$; and pH 5.6) dextrinizes 5260 mg starch dry substance Merck Amylum solubile.

A folder EB-SM-0009.02/01 describing this analytical method in more detail is available upon request to Novozymes A/S, Denmark, which folder is hereby included by reference.

pNP-G7 Assay

The alpha-amylase activity may be determined by a method employing the G7-pNP substrate. G7-pNP which is an abbreviation for 4,6-ethylidene($G_7$)-p-nitrophenyl($G_1$)-

☐,D-maltoheptaoside, a blocked oligosaccharide which can be cleaved by an endo-amylase, such as an alpha-amylase. Following the cleavage, the alpha-Glucosidase included in the kit digest the hydrolysed substrate further to liberate a free PNP molecule which has a yellow color and thus can be measured by visible spectophometry at lambda=405 nm (400-420 nm.). Kits containing G7-pNP substrate and alpha-Glucosidase is manufactured by Roche/Hitachi (cat. No. 11876473).

Reagents:

The G7-pNP substrate from this kit contains 22 mM 4,6-ethylidene-G7-pNP and 52.4 mM HEPES (2-[4-(2-hydroxyethyl)-1-piperazinyl]-ethanesulfonic acid), pH 7.0).

The alpha-Glucosidase reagent contains 52.4 mM HEPES, 87 mM NaCl, 12.6 mM $MgCl_2$, 0.075 mM $CaCl_2$, ≥4 kU/L alpha-glucosidase).

The substrate working solution is made by mixing 1 mL of the alpha-Glucosidase reagent with 0.2 mL of the G7-pNP substrate. This substrate working solution is made immediately before use.

Dilution buffer: 50 mM MOPS, 0.05% (w/v) Triton X100 (polyethylene glycol p-(1,1,3,3-tetramethylbutyl)-phenyl ether $(C_{14}H_{22}O(C_2H_4O)_n$ (n=9-10))), 1 mM CaCl2, pH8.0.

Procedure:

The amylase sample to be analyzed is diluted in dilution buffer to ensure the pH in the diluted sample is 7. The assay is performed by transferring 20μl diluted enzyme samples to 96 well microtiter plate and adding 80 μl substrate working solution. The solution is mixed and pre-incubated 1 minute at room temperature and absorption is measured every 20 sec. over 5 minutes at OD 405 nm.

The slope (absorbance per minute) of the time dependent absorption-curve is directly proportional to the specific activity (activity per mg enzyme) of the alpha-amylase in question under the given set of conditions. The amylase sample should be diluted to a level where the slope is below 0.4 absorbance units per minute.

Phadebas Activity Assay:

The alpha-amylase activity may also be determined by a method using the Phadebas substrate (from for example Magle Life Sciences, Lund, Sweden). A Phadebas tablet includes interlinked starch polymers that are in the form of globular microspheres that are insoluble in water. A blue dye is covantly bound to these microspheres. The interlinked starch polymers in the microsphere are degraded at a speed that is proportional to the alpha-amylase activity. When the alpha-amylase degrades the starch polymers, the released blue dye is water soluble and concentration of dye can be determined by measuring absorbance at 620 nm. The concentration of blue is proportional to the alpha-amylase activity in the sample.

The amylase sample to be analysed is diluted in activity buffer with the desired pH. One substrate tablet is suspended in 5 mL activity buffer and mixed on magnetic stirrer. During mixing of substrate transfer 150 μl to microtiter plate (MTP) or PCR-MTP. Add 30 μl diluted amylase sample to 150 μl substrate and mix. Incubate for 15 minutes at 37° C. The reaction is stopped by adding 30 μl M NaOH and mix. Centrifuge MTP for 5 minutes at 4000×g. Transfer 100 μl to new MTP and measure absorbance at 620 nm.

The amylase sample should be diluted so that the absorbance at 620 nm is between 0 and 2.2, and is within the linear range of the activity assay.

Reducing Sugar Activity Assay:

The alpha-amylase activity may also be determined by reducing sugar assay with for example corn starch substrate. The number of reducing ends formed by the alpha-amylase hydrolysing the alpha-1,4-glycosidic linkages in starch is determined by reaction with p-Hydroxybenzoic acid hydrazide (PHBAH). After reaction with PHBAH the number of reducing ends can be measured by absorbance at 405 nm and the concentration of reducing ends is proportional to the alpha-amylase activity in the sample.

The corns starch substrate (3 mg/ml) is solubilised by cooking for 5 minutes in milliQ water and cooled down before assay. For the stop solution prepare a Ka-Na-tartrate/NaOH solution (K-Na-tartrate (Merck 8087) 50 g/l, NaOH 20 g/l) and prepare freshly the stop solution by adding p-Hydroxybenzoic acid hydrazide (PHBAH, Sigma H9882) to Ka-Na-tartrate/NaOH solution to 15 mg/ml.

In PCR-MTP 50 μl activity buffer is mixed with 50 μl substrate. Add 50 μl diluted enzyme and mix. Incubate at the desired temperature in PCR machine for 5 minutes. Reaction is stopped by adding 75 μl stop solution (Ka-Na-tartrate/NaOH/PHBAH). Incubate in PCR machine for 10 minutes at 95° C. Transfer 150 μl to new MTP and measure absorbance at 405 nm.

The amylase sample should be diluted so that the absorbance at 405 nm is between 0 and 2.2, and is within the linear range of the activity assay.

EnzChek® Assay:

For the determination of residual amylase activity an EnzChek® Ultra Amylase Assay Kit (E33651, Invitrogen, La Jolla, Calif., USA) may be used. The substrate is a corn starch derivative, DQ™ starch, which is corn starch labeled with BODIPY® FL dye to such a degree that fluorescence is quenched. One vial containing approx. 1 mg lyophilized substrate is dissolved in 100 microliters of 50 mM sodium acetate (pH 4.0). The vial is vortexed for 20 seconds and left at room temperature, in the dark, with occasional mixing until dissolved. Then 900 microliters of 100 mM acetate, 0.01% (w/v) TRITON® X100, 0.125 mM $CaCl_2$, pH 5.5 is added, vortexed thoroughly and stored at room temperature, in the dark until ready to use. The stock substrate working solution is prepared by diluting 10-fold in residual activity buffer (100 mM acetate, 0.01% (w/v) TRITON® X100, 0.125 mM $CaCl_2$, pH 5.5). Immediately after incubation the enzyme is diluted to a concentration of 10-20 ng enzyme protein/ml in 100 mM acetate, 0.01% (W/v) TRITON® X100, 0.125 mM $CaCl_2$, pH 5.5. For the assay, 25 microliters of the substrate working solution is mixed for 10 second with 25 microliters of the diluted enzyme in a black 384 well microtiter plate. The fluorescence intensity is measured (excitation: 485 nm, emission: 555 nm) once every minute for 15 minutes in each well at 25° C. and the $V_{max}$ is calculated as the slope of the plot of fluorescence intensity against time. The plot should be linear and the residual activity assay has been adjusted so that the diluted reference enzyme solution is within the linear range of the activity assay.

Pullulanase Assays

Pullulanase Activity (NPUN) Assay

Endo-pullulanase activity in NPUN is measured relative to a Novozymes pullulanase standard. One pullulanase unit (NPUN) is defined as the amount of enzyme that releases 1 micro mol glucose per minute under the standard conditions (0.7% red pullulan (Megazyme), pH 5, 40° C., 20 minutes). The activity is measured in NPUN/ml using red pullulan.

1 mL diluted sample or standard is incubated at 40° C. for 2 minutes. 0.5 mL 2% red pullulan, 0.5 M KCl, 50 mM citric acid, pH 5 are added and mixed. The tubes are incubated at 40° C. for 20 minutes and stopped by adding 2.5 ml 80% ethanol. The tubes are left standing at room temperature for 10-60 minutes followed by centrifugation 10 minutes at 4000 rpm. OD of the supernatants is then measured at 510 nm and the activity calculated using a standard curve.

Red-Pullulan Assay (Megazyme)
Substrate solution
0.1 g red-pullulan (megazyme S-RPUL)
0.75 ml 2M sodium acetate, pH5.5
14.25 ml H$_2$O
10 µl of enzyme samples were mixed with 80 µl of substrate solution and incubated at set temperatures (ex. 55, 60, 65° C.) for 20 min. 50 µl of ethanol was added to the reaction mixtures and centrifuge for 10 min. at 3500 rpm.

The supernatants were carefully taken out and the absorbance, A510 was determined.

PAHBAH-Pullulan Assay
Substrate solution
0.15 g BH4-pullulan
25 ml 50 mM Na acetate buffer, pH5.5
PAHBAH solution
0.0552 g Bismuth (III)-acetate
0.2 g PAHBAH
0.5 g Potassium sodium tartrate, tetrahydrate
10 ml 500 mM NaOH
10 µl of enzyme samples were mixed with 110 µl of substrate solution and incubated at set temperatures (e.g., 55, 60, 65° C.) for 20 min. 40 µl of PAHBAH solution was added to the reaction mixtures, incubated for another 20 min at 50° C. and the absorbance, A405 was determined.

Lintner Soluble Waxy Starch Assay
Substrate solution
0.2 g Lintner's waxy corn starch
2.5 ml 2M sodium acetate
97.5 ml H$_2$O
5 µl of enzyme samples were mixed with 100 µl of substrate solution and incubated at set temperatures (e.g., 55, 60, 65, 70, 75° C.) for 20 min. 100 µl of 0.15% I$_2$/1.5% KI solution was added to the reaction mixtures and the absorbance, A610 was determined.

PHADEBAS Assay (Used for Determining Relative Activity)
Substrate solution:
1 tablet of PHADEBAS alpha-amylase tablet
5 ml 50 mM Na acetate buffer, pH5
40 sec. microwave oven up to boiling
Stop solution:
18% acetic acid
Assay method:
Enzyme reaction in 96 well PCR tube
10 ul of enzyme samples were mixed with 100 ul of substrate solution and incubated at set temperatures (e.g., 55, 60, 65° C.) for 20 min. 50 ul of stop solution was added to the reaction mixtures and centrifuge for 10 minutes at 3500 rpm. The supernatants were carefully taken out and the absorbance at A600 was read.

EXAMPLE 1

Construction of Pullulanase Variants P380 and P507 from a Hybrid Parent Pullulanase A hybrid pullulanase was constructed by fusing the N-terminal amino acids 1-451 from a natural pullullulanase (SEQ ID NO: 1) isolated from *Bacillus acidopullulyticus* with the C-terminal amino acids 452-828 from a natural pullulanase (SEQ ID NO: 2) isolated from *Bacillus deramificans* This hybrid pullulanase, disclosed as SEQ ID NO: 3 herein, was used as the parent pullulanase for constructing variant pullulanases P380 (and P380-2) and P507 (and P507-2). The substitutions introduced into the hybrid parent enzyme are disclosed in table 1 below.

TABLE 1

Variant pullulanases P380 and P507

| Variant | Substitution using SEQ ID NO: 3 for numbering |
|---|---|
| P380 | N368G + N393A + Q431E + L432F + A492A + N610R + G624S + T631S + S632C |
| P507 | N368G + N393A + Q431E + L432F + A492A + N610R + G624S + T631S + S632C + N20G + Y28K + H80Y + Q187R + E310A + D311K + Q387L + Q459G + D586S + E699R + S798R |
| P380-2 | N222P + Q252A + Q256R + N368G + N393A + Q431E + L432F + A492A + N610R + G624S + T631S + S632C |
| P507-2 | N222P + Q252A + Q256R + N368G + N393A + Q431E + L432F + A492A + N610R + G624S + T631S + S632C + N20G + Y28K + H80Y + Q187R + E310A + D311K + Q387L + Q459G + D586S + E699R + S798R |

EXAMPLE 2

Relative Activity Measurements of Pullulanase Variants, P380-2 and P507-2

Relative activity measurements of selected pullulanase variants was carried out in the range of 65-79° C., pH 5.0 by the PHADEBAS assay described in the pullulanase assay section. The results are shown in the table 2 below.

TABLE 2

| | Relative activity | | |
|---|---|---|---|
| Variant | 76° C./65° C. | 78° C./65° C. | 79° C./65° C. |
| P380-2 | 32% | 7% | |
| P507-2 | 88% | 74% | 38% |

EXAMPLE 3

Construction of Pullulanase Libraries

Genomic DNAs from *Bacillus subtilis* strains harboring pullulanase genes of pullulanase variants P380-2 (SEQ ID NO: 15/16) or P507-2 (SEQ ID NO: 17/18) described in Example 1 above were isolated using NucleoSpin® Tissue kit [MACHEREY-NAGEL] according to its procedure. Pullulanase libraries were constructed as follows.

A reverse or forward primer having NNK or desired mutation(s) at target site(s) with 15 bp overlaps each other were designed and two PCRs were carried out using Primer1F or 2F and the reverse primer and the forward primer and Primer 1R or 2R using appropriate template genomic DNAsunder the following conditions. The resultant PCR fragments were purified by NucleoSpin® Gel and PCR Clean-up kit [MACHEREY-NAGEL] and ligated to vectors by In fusion cloning (Clontech). The in fusion mixture was then introduced into *E.coli* DH5α, Jet Competent *E. coli* Cell, BDL.

Primer F1
(SEQ ID NO: 19)
atgtattatggagctctataaaaatgaggagggaaccgaatgtccctaat acgttctag -continued

```
Primer R1
                                      (SEQ ID NO: 20)
TTATTGATTAACGCGTTTAATTTTGATCAATGACATC Primer F2
                                      (SEQ ID NO: 21)
atgtattatggagctctataaaaatgaggagggaaccgaatggctaaaaaa
ctaatttatg Primer R2
                                      (SEQ ID NO: 22)
TTATTGATTAACGCGTTTACTTTTTACCGTGGTCTG
```

Phusion polymerase (thermo scientific)
Total 20 µl
1.0 µl Template (100 ng/µl)
4.8 µl H$_2$O
4 µl Phusion HF Buffer
1.6 µl dNTP (2.5 mM)
0.2 µl Reverse primer (20 µM)
0.4 µl Phusion (2 U/µl)
8.0 µl Forward mutation primer(1 µM)
PCR-program:
98° C./30 sec
30×(98° C./10 sec, 60° C./20 sec, 72° C./3 min)
72° C./5 min
4° C./∞

EXAMPLE 4

Screening for Thermoactivity

*Bacillus* libraries constructed as in Example 3 were fermented in 96 well MTPs containing TB-gly medium (13.3 g/L Bacto™ Tryptone, 26.6 g/L Bacto™ Yeast extract D, 4.4 g/L Glycerol) with 6 mg/L chloramphenicol at 220 rpm, 37° C. and pullulanase activities were measured at several temperatures by Lintner soluble starch assay and/or Phadebas assay described in the pullulanase assay section.

TABLE 3a

Lists the relative activity of pullulanase variants, showing higher thermoactivity than their parental pullulanases.

|  | Relative activity of 78° C./65° C. (%) | Relative activity of 79° C./65° C. (%) |
|---|---|---|
| P380-2 | 8% | 2% |
| P507-2 | 68% | 30% |
| P523 | 64% | 34% |
| P530 | 60% | 45% |
| P564 | 78% | 52% |

TABLE 3b

Lists the relative activity of pullulanase variants, showing higher thermoactivity than their parental pullulanases.

|  | Relative activity of 78° C./75° C. (%) | Relative activity of 79.5° C./75° C. (%) |
|---|---|---|
| P530 | 71% | 43% |
| P576 | 88% | 55% |
| P578 | 80% | 65% |
| P558 | 80% | 62% |
| P591 | 99% | 67% |

TABLE 3c

Lists the relative activity of pullulanase variants, showing higher thermoactivity than their parental pullulanases.

|  | Relative activity of 78° C./75° C. (%) | Relative activity of 79.5° C./75° C. (%) |
|---|---|---|
| P530 | 71% | 43% |
| P544 | 92% |  |
| P546 | 86% |  |
| P547 | 76% |  |
| P548 | 96% |  |
| P549 | 87% |  |
| P579 | 106% | 82% |
| P592 | 92% | 63% |
| P530 | 72% | 47% |
| P576 | 81% | 56% |
| P588 | 79% | 56% |
| P590 | 84% | 68% |
| P585 | 83% | 69% |
| P585 | 82% | 75% |
| P594 | 88% | 70% |
| P595 | 83% | 62% |
| P583 | 80% | 77% |

|  | Relative activity of 78.5° C./75° C. (%) | Relative activity of 80° C./75° C. (%) |
|---|---|---|
| P530 | 88% | 53% |
| P554 | 84% | 65% |
| P555 | 95% | 59% |
| P556 | 86% | 70% |
| P567 | 89% | 64% |
| P571 | 85% | 59% |
| P572 | 86% | 62% |
| P573 | 82% | 68% |
| P574 | 91% | 64% |
| P581 | 88% | 72% |
| P582 | 86% | 78% |
| P584 | 86% | 76% |
| P586 | 90% | 73% |
| P587 | 86% | 60% |
| P593 | 79% | 71% |
| P596 | 87% | 68% |
| P597 | 88% | 77% |
| P598 | 91% | 68% |

|  | Relative activity of 79° C./75° C. (%) | Relative activity of 81.5° C./75° C. (%) |
|---|---|---|
| P380 | 2% | 2% |
| P507 | 38% | 6% |
| P530 | 65% | 12% |
| P599 | 88% | 49% |
| P600 | 84% | 44% |

TABLE 4

Substitutions of thermo-stabilized variants of P507-2

| Variant | Substitutions starting from variant P507-2 (position numbering is according to SEQ ID NO: 3) |
|---|---|
| P523 | P30* + V31* + N32* |
| P530 | P30* + V31* + N32* + D57N + D58P |
| P578 | Q29G + P30* + V31* + N32* + D57N + D58P |
| P558 | P30* + V31* + N32* + D57N + D58P + A195G |
| P591 | P30* + V31* + N32* + D57N + D58P + N197T |
| P564 | P30* + V31* + N32* + D57N + D58P + N202K |
| P544 | P30* + V31* + N32* + D57N + D58P + A345P |
| P546 | P30* + V31* + N32* + D57N + D58P + M402S |
| P576 | P30* + V31* + N32* + D57N + D58P + F456W |
| P548 | P30* + V31* + N32* + D57N + D58P + I460V |
| P592 | P30* + V31* + N32* + D57N + D58P + N479H |
| P547 | P30* + V31* + N32* + D57N + D58P + I514V |
| P549 | P30* + V31* + N32* + D57N + D58P + E560R |
| P579 | P30* + V31* + N32* + D57N + D58P + D615E |
| P556 | P30* + V31* + N32* + D57N + D58P + A345P + E560R |
| P554 | P30* + V31* + N32* + D57N + D58P + A345P + I514V |
| P555 | P30* + V31* + N32* + D57N + D58P + A345P + I460V + I514V |
| P567 | P30* + V31* + N32* + D57N + D58P + A195G + A345P + I460V + I514V |
| P571 | P30* + V31* + N32* + D57N + D58P + N202K + A345P + E560R |
| P572 | P30* + V31* + N32* + D57N + D58P + A345P + M402S + E560R |
| P573 | P30* + V31* + N32* + D57N + D58P + N202K + A345P + M402S + E560R |
| P574 | P30* + V31* + N32* + D57N + D58P + A195G + N202K + A345P + M402S + I460V + I514V |
| P576 | P30* + V31* + N32* + D57N + D58P + F456W |
| P581 | Q29G + P30* + V31* + N32* + D57N + D58P + A195G + A345P + I460V + I514V |
| P582 | Q29G + P30* + V31* + N32* + D57N + D58P + A195G + N202K + A345P + M402S + I460V + I514V |
| P583 | Q29G + P30* + V31* + N32* + D57N + D58P + A195G + N202K + A345P + M402S + I460V + I514V + E560R |
| P584 | Q29G + P30* + V31* + N32* + D57N + D58P + A195G + N202K + A345P + M402S + I460V + I514V + E560R + D615E |
| P585 | P30* + V31* + N32* + D57N + D58P + A195G + A345P + M402S + I460V + I514V + E560R |
| P586 | P30* + V31* + N32* + D57N + D58P + A195G + A345P + M402S + I514V |
| P587 | P30* + V31* + N32* + D57N + D58P + A195G + A345P |
| P588 | P30* + V31* + N32* + D57N + D58P + A195G + A345P + F456W |
| P590 | Q29G + P30* + V31* + N32* + D57N + D58P + A195G + A345P + M402S + F456W + I460V + I514V |
| P592 | P30* + V31* + N32* + D57N + D58P + N479H |
| P593 | P30* + V31* + N32* + D57N + D58P + A195G + A345P + M402S + F456W + I460V + I514V + E560R |
| P594 | P30* + V31* + N32* + D57N + D58P + A195G + A345P + M402S + I460V + N479H + I514V + E560R |
| P595 | P30* + V31* + N32* + D57N + D58P + N197T + A345P + M402S + I460V + I514V + E560R |
| P596 | Q29G + P30* + V31* + N32* + D57N + D58P + A195G + A252I + N202K + A345P + M402S + I460V + I514V + E560R |
| P597 | Q29G + P30* + V31* + N32* + D57N + D58P + A195G + N197T + N202K + A345P + M402S + I460V + I514V + E560R |
| P598 | Q29G + P30* + V31* + N32* + D57N + D58P + A195G + N202K + A345P + M402S + F456W + I460V + I514V + E560R |
| P599 | Q29G + P30* + V31* + N32* + D57N + D58P + A195G + N197T + A345P + M402S + F456W + I460V + I514V + E560R |
| P600 | Q29G + P30* + V31* + N32* + D57N + D58P + A195G + A345P + M402S + F456W + I460V + N479H + I514V + E560R |
| P602 | Q29G + P30* + V31* + N32* + D57N + D58P + A195G + N197T + N202K + A345P + M402S + F456W + I460V + I514V + E560R |
| P603 | Q29G + P30* + V31* + N32* + D57N + D58P + A195G + N202K + A345P + M402S + F456W + I460V + N479H + I514V + E560R |
| P604 | Q29G + P30* + V31* + N32* + D57N + D58P + A195G + N197T + N202K + A345P + M402S + F456W + I460V + N479H + I514V + E560R |

EXAMPLE 5

Fermentation of the *Bacillus* Strains

*B. subtilis* strains expressing the variants were fermented on a rotary shaking table in 500 ml baffled flasks containing 100 ml TB-gly with 6 mg/L chloramphenicol at 220 rpm, 37° C. The cultures was centrifuged (20000×g, 20 min) and the supernatants were carefully decanted from the precipitates. The supernatants were filtered through a 0.45 um filter unit to remove the rest of the *Bacillus* host cells.

EXAMPLE 6

Purification of Pullulanases

Purification of pullulanases was carried out by β-cyclodextrin affinity column and followed by anion exchange column chromatography. After purification, pullulanases were dialyzed against 20 mM sodium acetate buffer (pH 5.5) and concentrated.

EXAMPLE 7

Enzyme Thermostability Measurement

Purified enzyme was diluted with 50 mM sodium acetate pH 5.0 or 4.3 to 0.5 mg/ml and mixed with the equal volume of SYPRO Orange (Invitrogen) diluted with Milli-Q water. Thirty microliters of mixture solution was transfer to LightCycler 480 Multiwell Plate 96 (Roche Diagnostics) and the plate was sealed.

Equipment parameters of TSA:
- Apparatus: LightCycler 480 Real-Time PCR System (Roche Applied Science)
- Scan rate: 0.02° C./sec
- Scan range: 37-96° C.
- Scan rate: 1.26° C./min
- Integration time: 0.5 sec
- Excitation wave length 465 nm
- Emission wave length 580 nm The obtained fluorescence signal was normalized into a range of 0 and 1. The Melting temperature (Tm) was defined as the temperature where the normalized value is closest to 0.5.

| | TSA Tm (° C.) | |
|---|---|---|
| | pH 4.3 | pH 5.0 |
| P380-2 | 75.5 | 76.7 |
| P507-2 | 80.4 | 80.7 |
| P530 | 80 | 80.4 |
| P558 | 79.9 | 80.5 |
| P567 | 79.6 | 80.4 |
| P574 | 80.6 | 80.8 |
| P576 | 78 | 78.6 |
| P578 | 78.1 | 78.2 |
| P583 | 80 | 80.5 |
| P598 | 80.6 | 81.3 |
| P599 | — | — |

EXAMPLE 8

Liquefaction and Fermentation Testing of Pullulanase Variant P380-2

The thermostabilized pullulanase variant, P380-2, was application tested in lab scale liquefaction and fermentation assays. Ground corn and backset were obtained from industrial ethanol plants. A corn slurry was made to 30.5% dry solids (% DS) with a backset inclusion rate of 30%. The slurries were made in the stainless steel Labomat canisters. The Labomat is the machine used to make lab scale liquefacts as it uses sealed canisters thus eliminating water evaporation, provides constant mixing and can operate at the elevated temperatures needed for corn liquefaction. The slurries were equilibrated for 15-30 minutes before pH measurement and adjustment. The pH was adjusted to between 4.95 and 5.05 for all slurries. The amylase used in this experiment was BE369 dosed at 2.1 µg/g DS. The P380-2 pullulanase was tested at 4 different doses (5, 10, 20 and 50 micrograms enzyme protein per gram dry solids). The control was BE369 amylase alone. After the slurry pH was adjusted, the enzymes were added at the appropriate doses. The canisters were sealed and mixed prior to insertion in the Labomat. The Labomat settings were: ramp to 80° C., hold at 80° C. for 120 minutes total and mixing for 30 seconds clockwise then 30 seconds counterclockwise. After the liquefaction, the canisters were removed and incubated in an ice and water bath for 10-20 minutes to aid in rapid cooling to room temperature. The liquefacts had urea added to a final concentration of 1000 ppm and penicillin added to a final concentration of 3 ppm. The pH was checked and re-adjusted if needed to be between 4.95 and 5.05. Approximately 5 grams of each liquefact was aliquoted into a pre-weighed, drilled 15 mL flip top centrifuge tube. For each liquefact, there were 5 replicate tubes created. After the liquefacts were aliquoted, the filled tubes were weighed again. The glucoamylase used in this experiment was a Glucoamylase A blend dosed at 0.5 AGU per gram dry solids. The yeast used was Ethanol Red. It was rehydrated by adding 5.5 grams of active dry yeast to 100 milliliters of warm tap water and incubating at 32° C. for 30 minutes with occasional mixing by hand. To start the fermentations, each tube was dosed with Glucoamylase A, water and rehydrated yeast. The fermentations were incubated in a 32° C. water bath for 54 hours with mixing twice a day by hand. The fermentations were stopped with the addition of 10 microliters per gram of mash of 40% sulfuric acid. The tubes were then vortexed to mix and centrifuged at 3000 RPM for 10 minutes to remove the solids. The liquid samples were filtered through a 0.45 micron syringe filter into HPLC vials. The HPLC (using the standard fuel program) was used to quantify ethanol, residual dextrins (DP1-4+, fructose), organic acids (acetate and lactate) and glycerol. Statistical analysis was done using SAS JMP software (version 11).

The result, as seen in FIG. 1, shows a clear increase in ethanol yield when the thermostable pullulanase variant, P380-2, was added to the liquefaction mix.

EXAMPLE 9

Liquefaction and Fermentation Testing of Pullulanase Variant P380-2

A second experiment was done where corn slurries with an amylase added were heated in an 80° C. water bath for 30 minutes prior to the addition of the P380-2 pullulanase. The corn slurries were made in the same way as described above (in a capped Nalgene bottle rather than the stainless steel Labomat canister). The BE369 amylase was dosed at 2.1 µg/g DS, the slurries capped and incubated in the 80° C. water bath with manual shaking every 2-3 minutes for the first 30 minutes. The P380-2 pullulanase was dosed at 0, 5 or 10 micrograms per gram dry solids. The liquefactions were continued for another 90 minutes with occasional mixing by hand. After liquefaction, the mashes were cooled to room temperature and urea added to 1000 ppm and penicillin added to 3 ppm as before. Small scale fermentations were done as described above with Glucoamylase A dosed at 0.5 AGU per gram dry solids.

Figure 2:
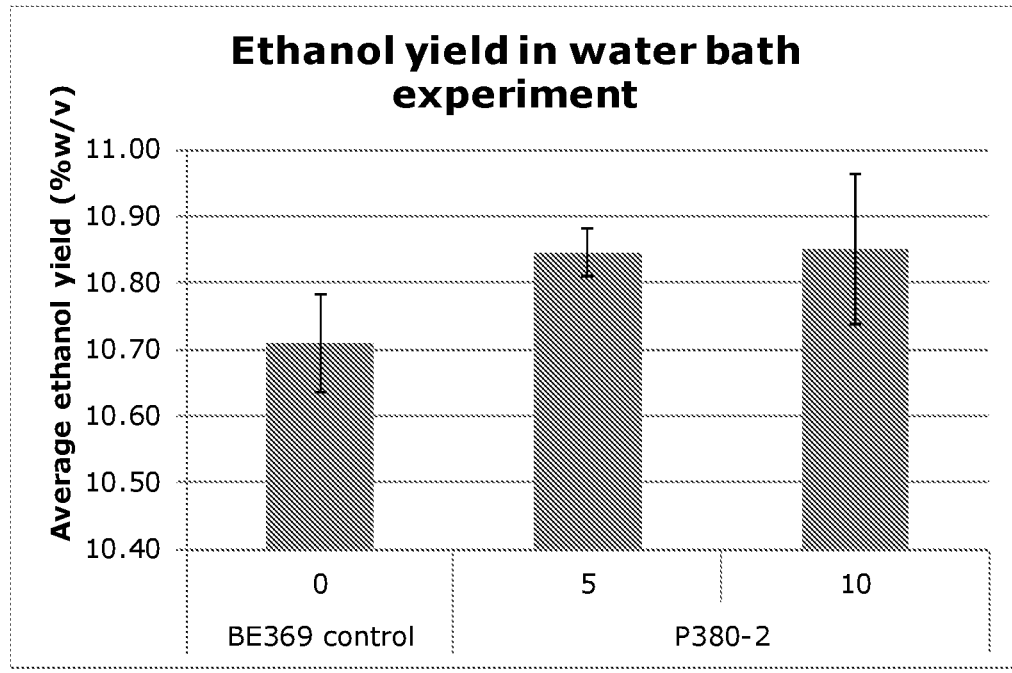
FIG. 2 shows ethanol yields from experiment testing addition of P380-2 to an 80° C. slurry after 30 minutes of liquefaction with amylase alone. With removal of several outliers, JMP statistical analysis shows the two doses of P380-2 are higher in ethanol yield than amylase control.
Figure 3:
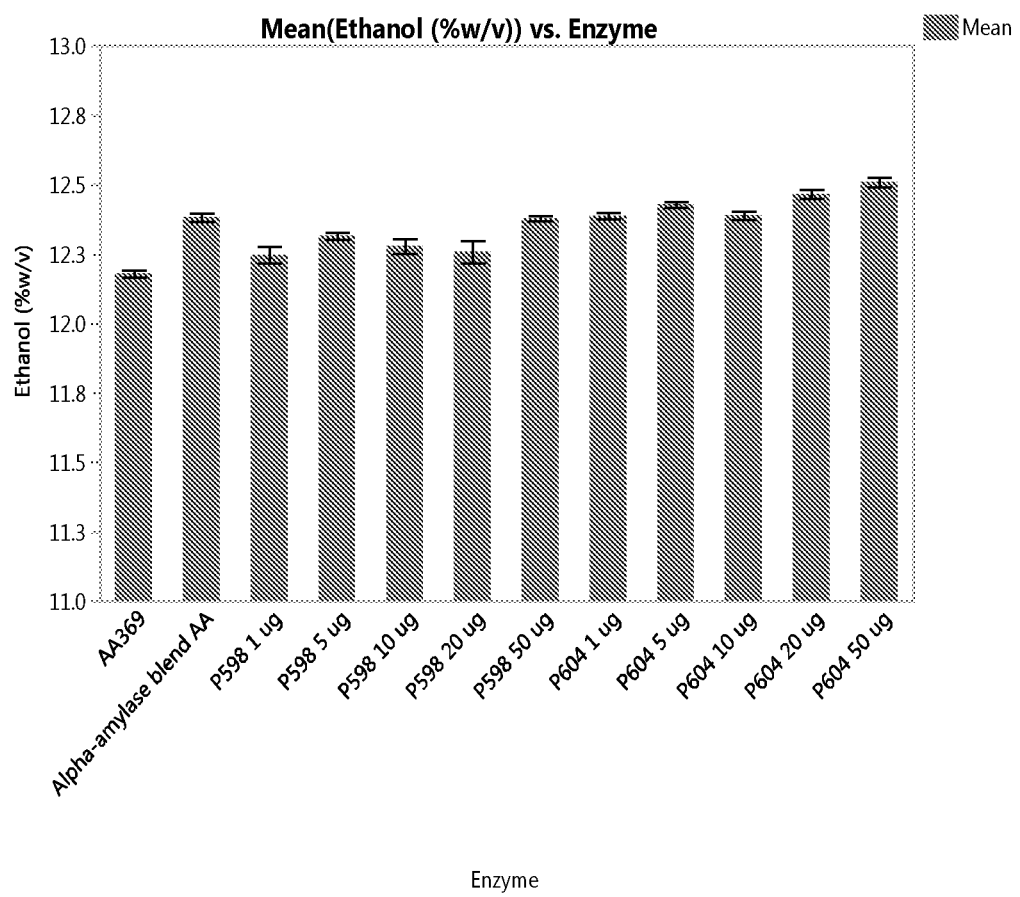
FIG. 3 shows average ethanol yields (in % w/v) for the two amylase controls (Alpha-amylase BE369 (AA369) and Alpha-amylase blend AA) and the five doses of either P598 or P604 after an 80° C. liquefaction and standard lab scale fermentation assays. The 50 microgram enzyme protein per gram dry solids dose of P604 produced statistically more ethanol than the Alpha-amylase blend AA control as determined by the ANOVA and Tukey-Kramer tests in SAS JMP software. All of the P604 doses produced statistically more ethanol than the AA369 control. The 5 and 50 micrograms enzyme protein per gram dry solids of P598 produced statistically more ethanol than the AA369 control.
Figure 4:
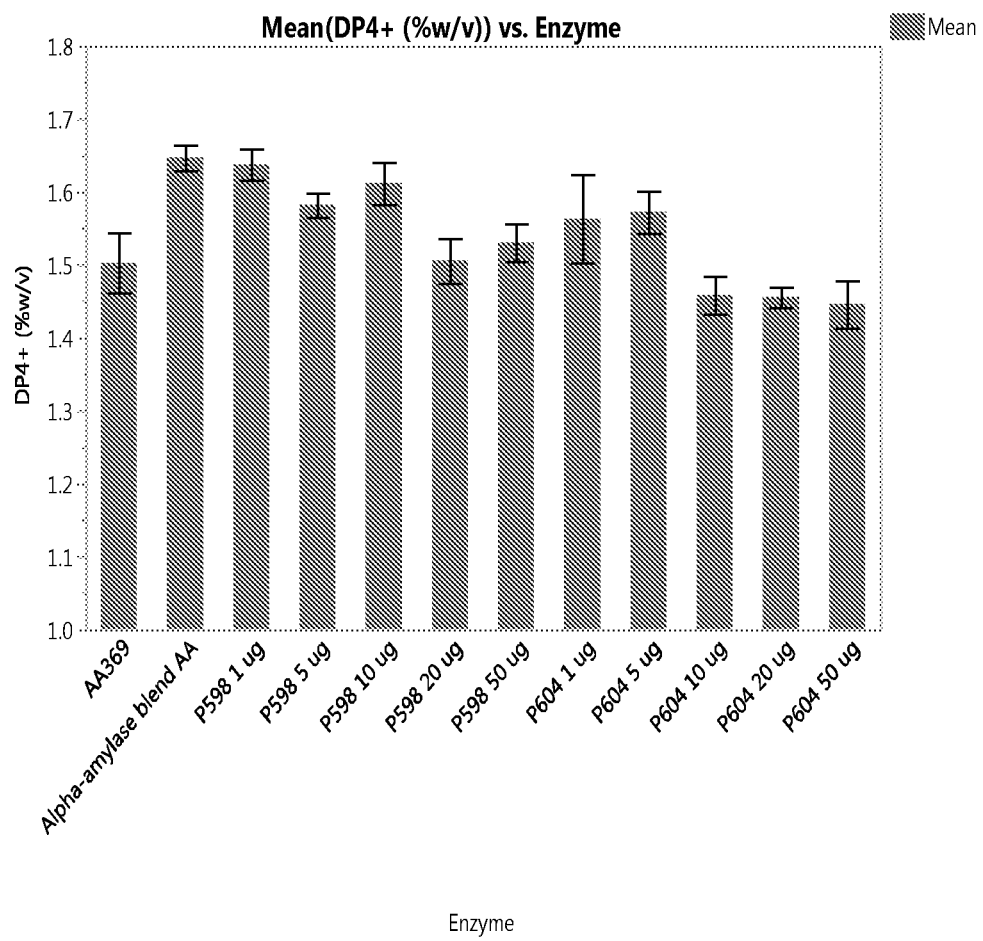
FIG. 4 shows average residual DP4+ concentrations for the two controls (AA369 and Alpha-amylase blend AA) and the five doses of P598 and P604 after the 80° C. liquefaction and 54 hour fermentation assays. The DP4+ concentrations for the 10, 20 and 50 microgram enzyme protein per gram dry solids doses of P604 were statistically lower than the Alpha-amylase blend AA control after 54 hours of fermentation.
Figure 5:
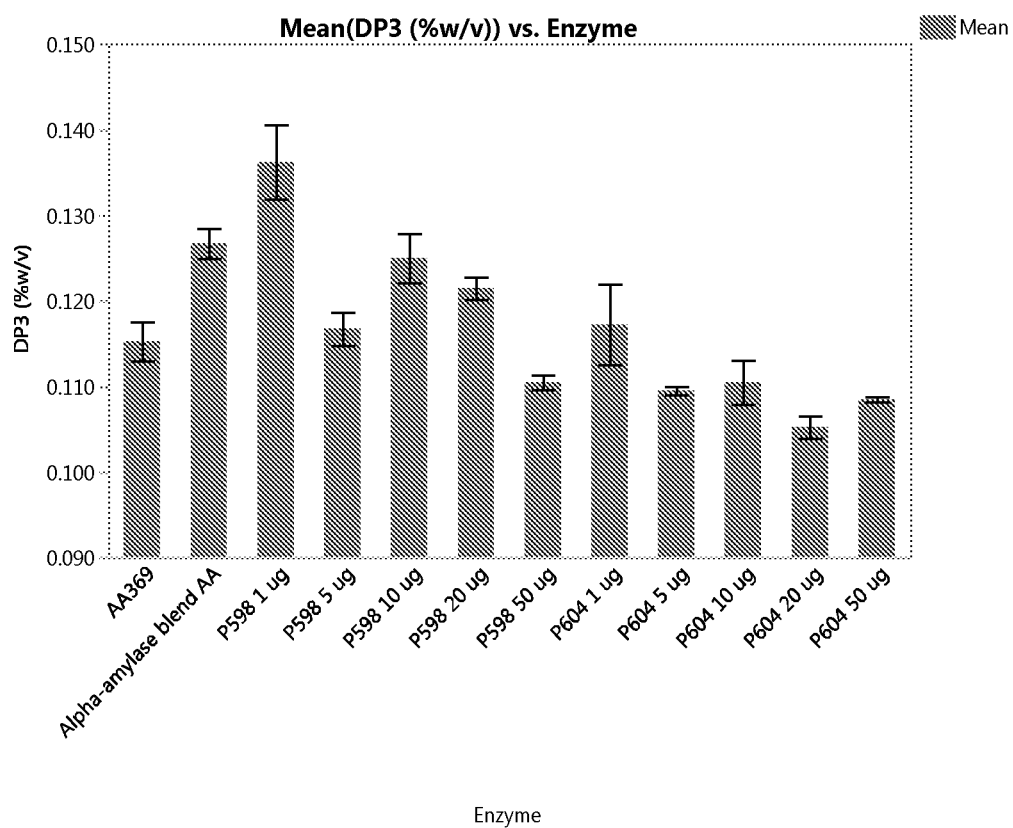
FIG. 5 shows average residual DP3 concentrations for the two controls (AA369 and Alpha-amylase blend AA) and the five doses of P598 and P604 after the 80° C. liquefaction and 54 hour fermentation assays. The 50 microgram enzyme protein per gram dry solids dose of P598 and the 5, 10, 20 and 50 micrograms enzyme protein per gram dry solids doses of P604 had statistically lower residual DP3 concentrations than the Alpha-amylase blend AA control.
Figure 6:
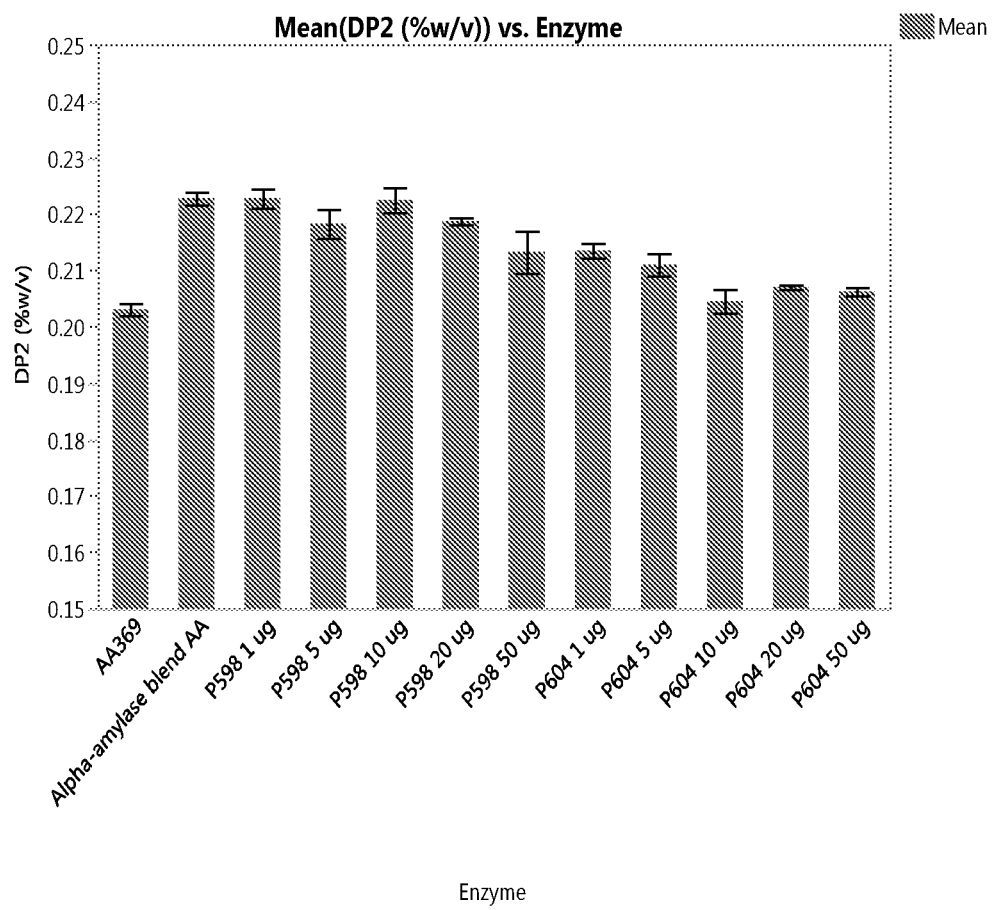
FIG. 6 shows average residual DP2 concentrations for the two controls (AA369 and Alpha-amylase blend AA) and the five doses of P598 and P604 after the 80° C. liquefaction and 54 hour fermentation assays. All doses of P604 had statistically significantly less DP2 remaining at the end of fermentation than the Alpha-amylase blend AA control. The 50 micrograms enzyme protein per gram dry solids dose of P598 had statistically lower DP2 than the Alpha-amylase blend AA control.

The result, shown in FIG. 2, clearly indicates an increase in ethanol yield also when the thermostable pullulanase variant, P380-2, is added after the mash has reached 80° C.

EXAMPLE 10

Liquefaction and Fermentation Test of Pullulanase Variants P598 and P604

The thermo-stabilized pullulanase variants, P598 and P604, were application tested in lab scale liquefaction and fermentation assays. Ground corn was obtained from an industrial ethanol plant. A corn slurry was made to 32% dry solids (% DS). The slurries were made in the stainless steel Labomat canisters. The Labomat is the machine used to make lab scale liquefacts as it uses sealed canisters thus eliminating water evaporation, provides constant mixing and can operate at the elevated temperatures needed for corn liquefaction. The slurries were equilibrated for 15-30 minutes before pH measurement and adjustment. The pH was adjusted to between 5.0 and 5.2 for all slurries. The amylase product used in this experiment (for all pullulanase treatments) was Alpha-amylase blend AA dosed at 0.021% weight enzyme product per weight of ground corn. The P598 and P604 pullulanases were tested at 5 different doses (1, 5, 10, 20 and 50 micrograms enzyme protein per gram dry solids). The controls were AA369 product alone dosed at 0.0857 KNU(AH) per gram dry solids or Alpha-amylase blend AA alone dosed at 0.021% weight of product per weight of corn. After the slurry pH was adjusted, the enzymes were added at the appropriate doses. The canisters were sealed and mixed prior to insertion in the Labomat. The Labomat settings were: ramp to 80° C., hold at 80° C. for 120 minutes total and mixing for 30 seconds clockwise then 30 seconds counterclockwise. After the liquefaction, the canisters were removed and incubated in an ice and water bath for 10-20 minutes to aid in rapid cooling to room temperature. The liquefacts had urea added to a final concentration of 250 ppm for all Alpha-amylase blend AA containing mashes including the pullulanase treatments or 1000 ppm for the AA369 control. Penicillin was added to a final concentration of 3 ppm. The pH was checked but not re-adjusted. Approximately 5 grams of each liquefact was aliquoted into a pre-weighed, drilled 15 mL flip top centrifuge tube. For each liquefact, there were 4 replicate tubes created. After the liquefacts were aliquoted, the filled tubes were weighed again. The glucoamylase used in this experiment was Glucoamylase blend B dosed at 0.6 AGU per gram dry solids. The yeast used was Fermentis Ethanol Red. It was rehydrated by adding 2.75 grams of active dry yeast to 50 milliliters of warm tap water and incubating at 32° C. for 30 minutes with occasional mixing by hand. To start the fermentations, each tube was dosed with Glucoamylase blend B, water and rehydrated yeast (added 100 microliters of rehydrated yeast to each tube). The fermentations were incubated in a 32° C. water bath for 54 hours with mixing twice a day by hand. The fermentations were stopped with the addition of 10 microliters per gram of mash of 40% sulfuric acid. The tubes were vortexed to mix and centrifuged at 3000 RPM for 10 minutes to remove the solids. The liquid samples were filtered through a 0.45 micron syringe filter into HPLC vials. The HPLC (using the standard fuel program) was used to quantify ethanol, residual dextrins (DP1-4+, fructose), organic acids (acetate and lactate) and glycerol. Statistical analysis was done using SAS JMP software (version 11).

---

The invention claimed is:

1. A variant pullulanase that comprises substitutions at positions corresponding to positions in the polypeptide of SEQ ID NO: 3, wherein the variant comprises the combination of substitutions that correspond to substitutions N368G+N393A+Q431E+L432F+N610R+G624S+T631S+S632C in the polypeptide of SEQ ID NO: 3, wherein the variant comprises an alanine or a serine at the position corresponding to position 492 of the polypeptide of SEQ ID NO: 3, and wherein the variant optionally further comprises the combination of substitutions that correspond to substitutions N222P+Q252A+Q256R in the polypeptide of SEQ ID NO: 3, wherein the variant has pullulanase activity, and wherein the variant has at least 95%, but less than 100% sequence identity to the polypeptide of SEQ ID NO: 3.

2. The variant according to claim 1, wherein said variant has at least 30% relative enzymatic activity when measured at 76° C. relative to enzymatic activity at 65° C. under the same conditions.

3. The variant according to claim 1, wherein the variant pullulanase further comprises the combination of substitutions that correspond to substitutions N20G+Y28K+H80Y+Q187R+E310A+D311K+Q387L+Q459G+D586S+E699R+S798R in the polypeptide of SEQ ID NO: 3, wherein the substitutions are present at positions corresponding to positions in the polypeptide of SEQ ID NO: 3.

4. The variant according to claim 1, wherein said variant has at least 50% relative enzymatic activity when measured at 78° C. relative to enzymatic activity at 65° C. under the same conditions.

5. The variant according to claim 3, wherein the variant comprises the combination of substitutions that correspond to substitutions:

N222P+Q252A+Q256R+N368G+N393A+Q431E+L432F+492A+N610R+G624S+T631S+S632C+N20G+Y28K+H80Y+Q187R+E310A+D311K+Q387L+Q459G+D586S+E699R+S798R in the polypeptide of SEQ ID NO: 3;

and wherein the variant further comprises one of the following combinations of deletions and substitutions:

P30*+V31*+N32*;
P30*+V31*+N32*+D57N+D58P;
Q29G+P30*+V31*+N32*+D57N+D58P;
P30*+V31*+N32*+D57N+D58P+A195G;
P30*+V31*+N32*+D57N+D58P+N197T;
P30*+V31*+N32*+D57N+D58P+N202K;
P30*+V31*+N32*+D57N+D58P+A345P;
P30*+V31*+N32*+D57N+D58P+M402S;
P30*+V31*+N32*+D57N+D58P+F456W;
P30*+V31*+N32*+D57N+D58P+I460V;
P30*+V31*+N32*+D57N+D58P+N479H;
P30*+V31*+N32*+D57N+D58P+I514V;
P30*+V31*+N32*+D57N+D58P+E560R;
P30*+V31*+N32*+D57N+D58P+D615E;
P30*+V31*+N32*+D57N+D58P+A345P+E560R;
P30*+V31*+N32*+D57N+D58P+A345P+I514V;
P30*+V31*+N32*+D57N+D58P+A345P+I460V+I514V;
P30*+V31*+N32*+D57N+D58P+A195G+A345P+I460V+I514V;
P30*+V31*+N32*+D57N+D58P+N202K+A345P+E560R;
P30*+V31*+N32*+D57N+D58P+A345P+M402S+E560R;
P30*+V31*+N32*+D57N+D58P+N202K+A345P+M402S+E560R;
P30*+V31*+N32*+D57N+D58P+A195G+N202K+A345P+M402S+I460V+I514V;
P30*+V31*+N32*+D57N+D58P+F456W;
Q29G+P30*+V31*+N32*+D57N+D58P+A195G+A345P+I460V+I514V;
Q29G+P30*+V31*+N32*+D57N+D58P+A195G+N202K+A345P+M402S+I460V+I514V;
Q29G+P30*+V31*+N32*+D57N+D58P+A195G+N202K+A345P+M402S+I460V+I514V+E560R;
Q29G+P30*+V31*+N32*+D57N+D58P+A195G+N202K+A345P+M402S+I460V+I514V+E560R+D615E;
P30*+V31*+N32*+D57N+D58P+A195G+A345P+M402S+I460V+I514V+E560R;

P30*+V31*+N32*+D57N+D58P+A195G+A345P+
M402S+1514V;
P30*+V31*+N32*+D57N+D58P+A195G+A345P;
P30*+V31*+N32*+D57N+D58P+A195G+A345P+
F456W;
Q29G+P30*+V31*+N32*+D57N+D58P+A195G+
A345P+M402S+F456W+1460V+1514V;
P30*+V31*+N32*+D57N+D58P+N479H;
P30*+V31*+N32*+D57N+D58P+A195G+A345P+
M402S+F456W+1460V+1514V+E560R;
P30*+V31*+N32*+D57N+D58P+A195G+A345P+
M402S+1460V+N479H+1514V+E560R;
P30*+V31*+N32*+D57N+D58P+N197T+A345P+
M402S+1460V+1514V+E560R;
Q29G+P30*+V31*+N32*+D57N+D58P+A195G+
A252I+N202K+A345P+M402S+1460V+1514V+
E560R;
Q29G+P30*+V31*+N32*+D57N+D58P+A195G+
N197T+N202K+A345P+M402S+1460V+1514V+
E560R;
Q29G+P30*+V31*+N32*+D57N+D58P+A195G+
N202K+A345P+M402S+F456W+1460V+1514V+
E560R;
Q29G+P30*+V31*+N32*+D57N+D58P+A195G+
N197T+A345P+M402S+F456W+1460V+1514V+
E560R;
Q29G+P30*+V31*+N32*+D57N+D58P+A195G+
A345P+M402S+F456W+1460V+N479H+1514V+
E560R;
Q29G+P30*+V31*+N32*+D57N+D58P+A195G+
N197T+N202K+A345P+M402S+F456W+1460V+
1514V+E560R;
Q29G+P30*+V31*+N32*+D57N+D58P+A195G+
N202K+A345P+M402S+F456W+1460V+N479H+
1514V+E560R;
Q29G+P30*+V31*+N32*+D57N+D58P+A195G+
N197T+N202K+A345P+M402S+F456W+1460V+
N479H+1514V+E560R; and
wherein the variant has pullulanase activity, and the variants have at least 95%, but less than 100% sequence identity to the polypeptide of SEQ ID NO: 3, wherein the deletions and substitutions correspond to deletions and substitutions in the polypeptide of SEQ ID NO: 3, wherein the deletions and substitutions are present at positions corresponding to positions in the polypeptide of SEQ ID NO: 3, and wherein said variant has at least 50% relative enzymatic activity when measured at 78° C. relative to enzymatic activity at 65° C. under the same conditions.

6. A composition comprising the variant pullulanase of claim 1 and a stabilizer.

7. The variant of claim 1, wherein the variant has at least 96%, but less than 100%, sequence identity to the polypeptide of SEQ ID NO: 3.

8. The variant of claim 1, wherein the variant has at least 97%, but less than 100%, sequence identity to the polypeptide of SEQ ID NO: 3.

9. The variant of claim 1, wherein the variant has at least 98%, but less than 100%, sequence identity to the polypeptide of SEQ ID NO: 3.

10. The variant of claim 1, wherein the variant has at least 99%, but less than 100% sequence identity to the polypeptide of SEQ ID NO: 3.

11. A process for producing a syrup from starch-containing material comprising the steps of:
   a) liquefying the starch-containing material at a temperature above the initial gelatinization temperature using an alpha-amylase and the variant pullulanase of claim 1; and
   b) saccharifying using a glucoamylase.

12. A process for producing fermentation products from starch-containing material comprising the steps of:
   a) liquefying the starch-containing material at a temperature above the initial gelatinization temperature using an alpha-amylase and the variant pullulanase of claim 1;
   b) saccharifying using a glucoamylase; and
   c) fermenting using a fermenting organism.

13. A method of producing a brewer's wort comprising adding to a mash, the variant pullulanase of claim 1.

* * * * *